(12) United States Patent
Sekiya et al.

(10) Patent No.: US 8,252,521 B2
(45) Date of Patent: Aug. 28, 2012

(54) METHOD OF SCREENING SUBSTANCE USEFUL IN TREATING DISEASE WITH THE USE OF GPR40 AND PHOSPHOLIPASE

(75) Inventors: Tomoko Sekiya, Ibaraki-Ken (JP);
Norimasa Miyamoto, Ibaraki-Ken (JP);
Hirokazu Tanaka, Chiba-Ken (JP);
Kenichi Morita, Ibaraki-Ken (JP);
Naoko Massaki, Ibaraki-Ken (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 497 days.

(21) Appl. No.: 12/084,697

(22) PCT Filed: Oct. 17, 2006

(86) PCT No.: PCT/JP2006/320611
§ 371 (c)(1),
(2), (4) Date: Aug. 10, 2009

(87) PCT Pub. No.: WO2007/052466
PCT Pub. Date: May 10, 2007

(65) Prior Publication Data
US 2010/0227350 A1    Sep. 9, 2010

(30) Foreign Application Priority Data

Nov. 4, 2005   (JP) ................................. 2005-321108

(51) Int. Cl.
*C12Q 1/02*    (2006.01)
*C12Q 1/68*    (2006.01)
(52) U.S. Cl. ............................................... 435/4; 435/6
(58) Field of Classification Search ........................ None
See application file for complete search history.

(56) References Cited

FOREIGN PATENT DOCUMENTS

WO    02/057783 A2    7/2002
WO    WO-2004/072650 A1    8/2004

OTHER PUBLICATIONS

Balazy M and Nigam S., Aging, lipid modifications and phospholipases-new concepts. Aging Research Reviews (2003) 2, 191-209.*
Briscoe C. P. et al., The Orphan G Protein-coupled Receptor GPR40 is Activate by Medium and Long Chain fatty Acids. J Biological Chemistry (2003) 278, 11301-11311.*
Ramanadham et al., Type IB secretory phospholipase A2 is contained in insulin secretory granules of pancreatic islet beta-cells and is co-secreted with insulin from glucose-stimulated islets.Biochim. Biophys. Acta 1390(3):301-312, 1998.*
Shapiro et al., "Role of GPR40 in Fatty acid action on the β cell line INS-1E", Biochemical and Biophysical Research Communication, vol. 335, Issue 1, pp. 97-104, Sep. 16, 2005.
Fujiwara et al., "Oleic acid interacts with GPR40 to induce $Ca^{2+}$ signaling in rat islet β-cells: mediation by PLC and L-type $Ca^{2+}$ channel and link to insulin release", American Journal of Physiology, vol. 289, No. 4, E670-E677, Oct. 2005.
Hardy et al., "Oleate Promotes he Proliferation of Breast Cancer Cells via the G Protein-coupled Receptor GPR40", Journal of Biological Chemistry, vol. 280, No. 14, pp. 13285-13291, Apr. 2005.
Sun, et al., Phospholipase $A_2$ in Astrocytes: Responses to Oxidative Street, Inflammation, and G Protein-Coupled Receptor Agonists, Molecular Neurobiology, vol. 31, Issue 1-3, pp. 27-42, Feb. 2005.
Supplementary European Search Report, EP 06811866, dated May 15, 2009.
Anonymous: "Phospholipase A2"Internet Article, [Online] May 14, 2009, pp. 1-3, XP002528076 Retrieved from the Internet: URL:http://en.wikipedia.org/wiki/Phosphol i paseA2> [retrieved on May 14, 2009] the whole document.
Amendment from Japanese Patent Application No. 2007-542317, filed Jan. 31, 2012. Translation enclosed.
Argument from Japanese Patent Application No. 2007-542317, filed Jan. 31, 2012. Translation enclosed.
Communication pursuant to Article 94(3) EPC from European Patent Application No. 06811866.0, dated Sep. 22, 2009.
Notification of Reason for Rejection from Japanese Patent Application No. 2007-542317, dated Dec. 2, 2011. Translation enclosed.
Response to Communication pursuant to Article 94(3) EPC from European Patent Application No. 06811866.0 dated Sep. 22, 2009, filed Apr. 1, 2010.

* cited by examiner

*Primary Examiner* — Ruixiang Li
(74) *Attorney, Agent, or Firm* — Clark & Elbing LLP

(57) ABSTRACT

The present invention relates to a screening method for determining whether a substance of interest is a substance which alters GPR40-mediated cell stimulating activities, comprising using a substance of interest, a biomembrane containing GPR40, or cells containing said biomembrane, and phospholipase or salts thereof. According to the present invention, substances involved in insulin secretion can be screened. In addition, according to the present invention, substance useful for the prevention or treatment of diabetes, diabetic complications and degenerative diseases, hyperglycemia, polyuria, ketonemia, acidosis, insulin resistance, impaired glucose tolerance, neurodegenerative diseases, insulinoma, cancers, hyperinsulinemia, hyperglyceridemia, fatty liver, hypoglycemia due to insulin hypersecretion, arteriosclerosis, hyperlipidemia, cerebral stroke, obesity, various diseases induced by diabetes or obesity, and the like.

7 Claims, 12 Drawing Sheets

METHOD OF SCREENING SUBSTANCE USEFUL IN TREATING DISEASE WITH THE USE OF GPR40 AND PHOSPHOLIPASE

CROSS REFERENCE TO RELATED APPLICATIONS

The present application is a national phase entry under 35 U.S.C. §371 of International Application No. PCT/JP2006/320611, filed Oct. 17, 2006, published in Japanese, which claims benefit of Japanese Patent Application No. 2005-321108, filed Nov. 4, 2005. The disclosures of all of said applications are incorporated by reference herein.

BACKGROUND OF THE INVENTION

1. Field of the Invention

The present invention relates to a method for screening a substance that alters cell-stimulating activity using GPR40, a G protein-coupled receptor protein and a phospholipase or a salt thereof, and a screening kit to be used for such screening.

2. Background Art

Many physiologically active substances such as hormones and neurotransmitters regulate biological functions through their specific receptor proteins expressed on cell surface membranes. Many of these receptors share a 7-transmembrane structure which couples with trimeric G protein (guanine nucleotide-binding protein) intracellularly and are accordingly called G-protein coupled receptors (GPCRs).

GPCR is expressed on the cell surface of a variety of functional cells, organs, and organ parts and activates or suppresses cellular functions by transmitting a signal intracellularly via binding to its regulatory molecule. Accordingly, GPCRs play important roles in a variety of organs and organ parts. It is important to clarify interactions between GPCRs and these physiologically active substances for better understanding of biological functions and for the development of drugs that are closely related thereto. The development of these therapeutic drugs requires efficient screening for GPCR agonists and antagonists, functional analyses of a receptor protein expressed in a living body, and expression systems of the gene in appropriate cells.

In recent years, the presence of a number of novel genes have been revealed by a random analysis of cDNA sequences shown in EST database and the like, or a comprehensive analysis of genome DNA. GPCRs share a 7-transmembrane domain and also a number of other common sequences. Because of this, novel members of GPCR have been found among a number of those newly discovered genes. Ligands for these novel GPCRs thus discovered are usually unidentified. Identification of ligands and functional analysis for orphan GPCRs whose ligands are not yet identified are believed to be significantly important because these may provide an opportunity for the development of new therapeutic drugs.

In most cases, it is difficult to predict a ligand for each of orphan GPCRs. Ligands for GPCRs include a wide variety of substances such as biological amines, amino acids, nucleic acids and its metabolites, peptides, proteins (for example, hormones, and chemokines), and lipids. Purification of a ligand from extracts requires an extraction method specific to each type of ligand substances. Also, in general, a type of signal transduction system activated by orphan GPCR after responding to a ligand is not easily predictable and studies are required in miscellaneous expression systems. Since prediction of a tissue in which a ligand is present is not easy, a number of different tissue extracts are required. Thus, the ligand identification for orphan GPCRs faces a great deal of difficulty. Discovery of a novel ligand for GPCR and its direct application, or screening for a new drug using the novel ligand is expected to provide an opportunity to develop new drugs of which action mechanism is novel and entirely different from that of currently available drugs.

GPR40 has been known as one of GPCRs (Biochemical and Biophysiological Research Communications, Vol. 239, pp 543-547, (1997)). Although ligands for GPR40 have not been completely elucidated, fatty acids have been reported as one of the ligands (WO2002/057783 and WO2003/068959).

GPR40 has been known to be expressed in pancreatic cells, Langerhans' islet β cells. GPR40 has been known to be involved in glucose-dependent insulin secretion in a mouse pancreas-derived cell strain MIN6 (WO2003/068959). In addition, GPR40 has been reported to be involved in insulin secretion in primary cultured islet cells (Ito Y et al., Nature, 422 (6928): 173-6, 2003). Further, involvement of GPR40 in proliferation of breast cancer has been reported (Hardy S et al., Journal of Biological Chemistry, 280 (14): 13285-91, 2005). In addition, it has been reported that hyperinsulinemia, fatty liver, hyperglyceridemia and the like induced by obesity are ameliorated in mice with reduced GPR40 expression (Steneberg P et al., Cell Metabolism, 1 (4): 245-58, 2005). Based on these findings, application of GPR40 agonists and antagonists is expected to the treatment of type I diabetes (insulin dependent diabetes), type II diabetes (non-insulin dependent diabetes), diabetic complications and degenerative diseases (for example, diabetic neuropathy, diabetic nephropathy, diabetic retinopathy, and the like), hyperglycemia, polyuria, ketonemia, acidosis, insulin resistance, impaired glucose tolerance, neurodegenerative diseases, insulinoma, cancers, hyperinsulinemia, hyperglyceridemia, fatty liver, hypoglycemia due to insulin hypersecretion, arteriosclerosis, hyperlipidemia, cerebral stroke, obesity, various diseases induced by diabetes or obesity, and the like.

As described above, fatty acids have been reported as ligands for GPR40. However, it is often difficult to prepare a ligand solution with fatty acids since fatty acids are barely soluble in an aqueous solvent system. Also, fatty acids are easily adsorbed to plastics or glass used for screening and unsaturated fatty acids are easily oxidized. Moreover, fatty acids are known to bind to albumin easily. Under physiological conditions, most of fatty acids are bound to blood albumin and only a small part of fatty acids (about 1%) exist as free fatty acids. For that reason, an inhibitory effect of bovine serum albumin (BSA) on GPR40 activity stimulated by fatty add have been observed in the screening of a GPR40 using a fatty acid, and the necessity of screening in the absence of serum or albumin is reported (for example, Ito Y et al., Nature, 422 (6928): 173-6, 2003). On the other hand, generally, the screening for a drug using cells and proteins is often carried out in the presence of serum or albumin (BSA and the like) since conditions closer to physiological conditions are required. If the screening is carried out in the absence of serum, a long time culture is usually difficult because of cellular damages in the serum free condition. It is therefore necessary that cells are cultured in a serum containing medium in advance and the medium must be replaced by a serum free medium at the time of the screening, which makes the process more complicated.

Accordingly, it has been expected for a new screening system not using fatty acid directly to screen for GPR40 agonists or antagonists.

Phospholipase is a family of enzymes that hydrolyze an ester linkage of glycerophospholipids, and is classified into phospholipases A1, A2, B, C, and D depending on the position of the ester linkage to be hydrolyzed. Phospholipase A2 (PLA2) is further classified into secretory (sPLA2), cytoplasmic (cPLA2) and calcium independent (iPLA2) forms. Among them, there are 10 enzymes known for sPLA2.

At the same time, it has been reported that phosphatidylcholine (1-palmitoyl-2-linolenoyl) that has been hydrolyzed by phospholipase A2 and oxidized induces calcium influx in cells expressing G2A, one of GPCRs, and that G2A is activated by an oxidized free fatty acid produced by oxidation and hydrolysis of phosphatidylcholine or cholesteryl linoleate (J. Biol. Chem., Vol. 280, Issue 49, 40676-40683, Dec. 9, 2005).

SUMMARY OF THE INVENTION

The present inventors have now found that, surprisingly, a phospholipase, in particular, secretory phospholipases A2 (sPLA2), honey bee venom phospholipase A2 and snake venom phospholipase A2, can activate GPR40-mediated cell stimulating activity, GPR40 being a G-protein coupled receptor. The present invention is based on these findings.

Accordingly, an objective of the present invention is to provide a screening method for a substance that alters GPR40 mediated cell stimulating activity using a phospholipase and a screening kit to be used for such method, and the like.

According to the present invention, the invention provides a screening method for determining whether a substance of interest is a substance which alters GPR40-mediated cell stimulating activities, comprising using a substance of interest, a biomembrane containing GPR40, or cells containing said biomembrane, and phospholipase or salts thereof. The term "biomembrane" used herein includes cell membranes, membranes such as organelles constructing cell membranes and cells, and lipid bilayer membranes. In addition, reconstructed membranes such as liposome are also included herein. In the present invention, a biomembrane containing GPR40, preferably, may be referred to as a cell membrane containing GPR40.

An aspect of the present invention provides a screening method for a substance that alters GPR40 mediated cell stimulating activity, which is characterized by using GPR40, a cell membrane containing GPR40 or a cell containing the cell membrane, and a phospholipase or a salt thereof.

According to a preferred aspect of the present invention, a method of the invention includes the following steps: contacting biomembranes containing GPR40 or cell containing those with phospholipase or salts thereof in the presence and absence of a substance to be screened, and measuring cell stimulating activity to compare between a result measured in the presence of the substance to be screened and a result measured in the absence of the substance.

Furthermore, the present invention provides a screening kit comprising at least a biomembrane containing GPR40 or a cell containing the biomembrane, and a phospholipase or a salt thereof. Also, the present invention provides use of a biomembranes containing GPR40 or a cell containing the biomembrane and a phospholipase or a salt thereof to screen a substance that alters GPR40 mediated cell stimulating activity.

According to the screening method of the present invention, substances involved in insulin secretion can be screened. Accordingly, GPR40 can screen substances involved in proliferation of cancer. According to the present invention, substances useful for prevention or treatment of type I diabetes (insulin dependent diabetes), type II diabetes (non-insulin dependent diabetes), diabetic complications and degenerative diseases (for example, diabetic neuropathy, diabetic nephropathy, diabetic retinopathy, and the like), hyperglycemia, polyuria, ketonemia, acidosis, insulin resistance, impaired glucose tolerance, neurodegenerative diseases, insulinoma, cancers, hyperinsulinemia, hyperglyceridemia, fatty liver, hypoglycemia due to insulin hypersecretion, arteriosclerosis, hyperlipidemia, cerebral stroke, obesity, various diseases induced by diabetes or obesity, and the like can be screened.

BRIEF DESCRIPTION OF DRAWINGS

FIG. 6A shows the result obtained using hGX-sPLA2-His.

FIG. 6B shows the result obtained using mGX-sPLA2-His.

DETAILED DESCRIPTION OF THE INVENTION

Phospholipase

Figure 1:
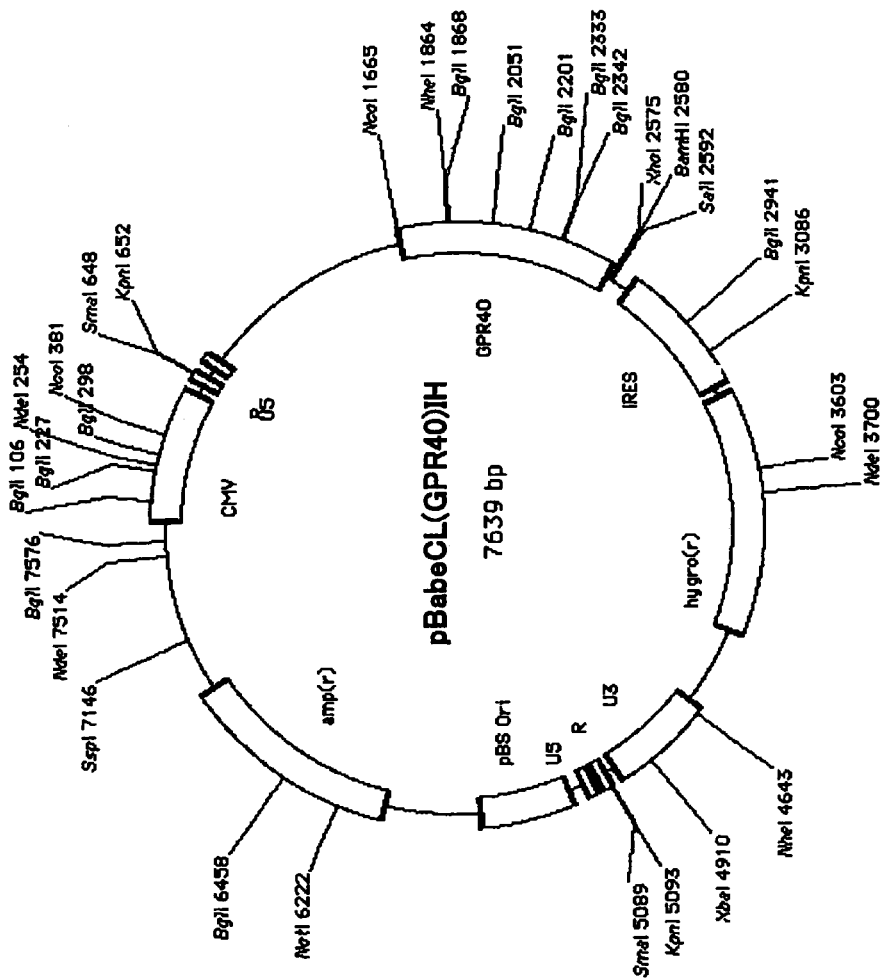
FIG. 1 shows the construction of pBabeCL(GPR40)IH.

The screening method according to the present invention uses a phospholipase. Phospholipases include phospholipases A1, A2, B, C, and D, and phospholipase A1 and phospholipase A2 are preferred and phospholipase A2 is more preferred in the present invention. Phospholipase A2 can be classified into secretory (sPLA2), cytoplasmic (cPLA2), and calcium independent (iPLA2) forms by nature. PLA2 contained in snake venom or honey bee venom is classified into secretory PLA2. The secretory phospholipase is preferred in the present invention. Also, phospholipases A2 derived from venoms such as honey bee venom and snake venom can be used. According to the present invention, secretory phospholipase A2, honey bee venom phospholipase A2, and snake venom phospholipase A2 are even more preferred as the phospholipase.

Secretory phospholipase A2 (sPLA2) can be classified into 10 groups, IB, IIA, IIC, IID, IIE, IIF, III, V, X, and XIIA, and in the present invention, groups IB, IIA, V, and X are preferred, and groups IB and X are more preferred, and group X is further preferred.

Phospholipases are well known enzymes and they are easily available for a person skilled in the art. For example, a phospholipase can be prepared from organisms comprising a desired phospholipase through extraction and purification processes using conventional methods. Moreover, commercially available phospholipases can be used. Furthermore, signal sequences, prepro-sequences, and sequences of a mature form are easily known from the database comprising these sequences and published references. Thus, it is possible to obtain a polynucleotide capable of expressing a desired phospholipase, prepare cells and the like in which the polynucleotide is introduced so as to express using genetic engineering methods, and use the cells.

Amino acid sequences of phospholipases and DNA sequences encoding the same have been reported. For example, for secretory phospholipase A2, Swiss Prot accession numbers: P04054 (human group IB), Q9Z0Y2 (mouse group IB), P04055 (rat group IB), P00592 (porcine group IB), P14555 (human group IIA), P31482 (mouse group IIA), P48076 (mouse group IIC), Q9UNK4 (human group IID), Q9NZK7 (human group IIE), Q9BZM2 (human group IIF), Q9NZ20 (human group III), P39877 (human group V), P97391 (mouse group V), O15496 (human group X), Q9QXX3 (mouse group GX), Q9QZT3 (rat group GX), and GenBank accession number: NM_030821 (human group IIA), and the like have been reported. In addition, for honey bee venom phospholipase A2, Swiss Prot accession number: P00630 and the like have been reported. Moreover, for snake venom phospholipase A2, Swiss Prot accession numbers: SP62022, P00602, and the like have been reported. For phospholipases used in the present invention, the amino acid sequence and the DNAs encoding the same can be specifically identified based on such published information.

Moreover, some of phospholipases become an active form through processing of their precursor phospholipases (for example, secretory phospholipase A2 and honey bee venom phospholipase A2). In addition, some of phospholipases become an active form when a prepro-sequence is further removed from a prepro-form in which a signal sequence is removed from a precursor (for example, Group IB secretory phospholipases A2, Group X secretory phospholipases A2, and honey bee venom phospholipase A2). The phospholipase used in the present invention can be any of precursor phospholipases, prepro-phospholipases and active form phospholipases; however, active form phospholipases are preferred. When used in experiments, active form phospholipases are optionally referred simply to as phospholipase. For these precursors, prepro-forms and active form phospholipases used in the present invention, the amino acid sequences and DNA encoding the same can be specifically identified based on the published information.

Specifically, the phospholipase of the present invention comprises polypeptides selected from a group consisting of (A) to (E):

(A) a polypeptide comprising any of the amino acid sequences identified by the accession numbers described above (preferably, any of the amino acid sequences of SEQ ID NOs: 7 to 12);

(B) a polypeptide comprising the amino acid sequences of (A) in which one or several (preferably one or a few) amino acids are substituted, deleted, inserted and/or added, and having substantially the same activity as the phospholipase;

(C) a polypeptide consisting of the amino acid sequences of (A) having 80% or higher identity to amino acid sequences of (A);

(D) a polypeptide encoded by a polynucleotide which can hybridize with a polynucleotide comprising a nucleotide sequence encoding the amino acid sequence of (A) above under stringent conditions, and having substantially the same activity as the phospholipase; and (E) a polypeptide encoded by a polynucleotide consisting of a base sequence having 80% or higher (preferably 85% or higher, more preferably 90% or higher, even more preferably 95% or higher, even further preferably 98% or higher, particularly preferably 99% or higher) identity to a base sequence encoding the amino acid sequence of (A), and having substantially the same activity as the phospholipase.

The phospholipase used in the present invention is preferably a "polypeptide comprising any of the amino acid sequences identified by the accession". The polypeptide includes salts thereof, polypeptides with or without a disulfide bond, phosphorylated or unphosphorylated polypeptides, and further polypeptides with or without a sugar chain. The phospholipase used in the present invention can be specifically identified by the amino acid sequence or DNA encoding the amino acid sequence based on the published information.

The "polypeptides with a disulfide bond" refers to polypeptides in which one amino acid (for example, cysteine) at a specific site is crosslinked with another amino acid (for example, cysteine) at another specific site by a —S—S— bond.

Herein, "any of the amino acid sequences identified by the accession numbers described above" refers to amino acid sequences identified by the accession numbers described above by the predetermined publicly-known database, and any of the amino acid sequences of SEQ ID NOs: 7 to 12 is preferable and the amino acid sequence of SEQ ID NO: 7 is more preferable.

Herein, polypeptides "having substantially the same activity as the phospholipase" refers to the polypeptides having activation effects directly or indirectly on GPR40, and GPR40 mediated signal transduction effects, in more detail, having cell stimulating activity on GPR40 expressing cells (for example, activity measured by the reporter assay system that can detect changes in translation and transcription of reporter genes due to production of signaling substances, intracellular $Ca^{2+}$ release, activation of adenylate cyclase, intracellular cAMP production, intracellular cGMP production, release of arachidonic acid, release of acetylcholine, production of inositol phosphate, changes in cell membrane potential, phosphorylation or activation of intracellular proteins, pH changing activity, phosphorylation or activation of MAP kinase, activation of c-fos, glycerol production activity, lipolysis activity, insulin secretion activity, and cell proliferation activity). And substantially the same means that the activity is qualitatively the same. In other words, in order to have "substantially the same activity as the phospholipase", preferably, the activity is equivalent (for example, about 0.01 to 100 folds, preferably 0.05 to 20 folds, more preferably 0.5 to 2 folds) to the activity of a phospholipase. These activities can be measured by conventional methods, for example, using the methods described in Examples below.

In one preferred aspect of the present invention, the polypeptide of (B) above (optionally referred to as "modified polypeptide" hereinafter) is a polypeptide containing any of the amino acid sequences identified by the accession numbers described above (preferably, any of the amino acid sequence of SEQ ID NOs: 7 to 12) which amino acid sequences have one or several (preferably one or a few) conservative substitutions, and still having substantially the same activity as the phospholipase.

"Conservative substitution" used herein refers to substitutions of one or several (preferably a few) amino acid residues with other chemically similar amino acid residue without substantially altering peptide activity. For example, there can be mentioned a case that a hydrophobic residue is substituted by another hydrophobic residue, or a polar residue is substituted by another polar residue with the same charge. Functionally similar amino acids with which such substitution can be made are well known for each amino acid in the art. Specific examples include alanine, valine, isoleucine, leucine, proline, tryptophan, phenylalanine, methionine, and the like as non-polar (hydrophobic) amino acids. Examples for polar (neutral) amino acids are glycine, serine, threonine, tyrosine, glutamine, asparagine, cysteine, and the like. Examples for positively charged (basic) amino acids are arginine, histidine, lysine, and the like. In addition, examples for negatively charged (acidic) amino acids are aspartic acid, glutamic acid, and the like.

Here, the number of amino acids which can be deleted, substituted, inserted and/or added is, for example, 1 to 30, preferably 1 to 20, more preferably 1 to 10, even more preferably 1 to 5, particularly preferably 1 to 2. In addition, the modified polypeptides include salts thereof, polypeptides with or without a disulfide bond, phosphorylated or unphospholyrated polypeptides, and polypeptides with or without a sugar chain. Thus, the source of the modified polypeptides is not limited to human so far as these conditions are satisfied.

These modified polypeptides may further include polypeptides with modification or alteration at the N-terminal (amino terminal) and the C-terminal (carboxyl terminal). For example, the C-terminal carboxyl group can be carboxylate (—COO—), amide (—CONH$_2$) or ester (—COOR). Here, the R may be, for example, a linear, branched or cyclic C1-6 alkyl group, a C6-12 aryl group, or the like. In addition, the modified polypeptides also may include polypeptides with an N-terminal amino group protected by a common protective group.

Examples of the polypeptides of (B) described above include phospholipases or variants thereof derived from human, rat, mouse, pig, honey bee, and snake, and specific examples also include phospholipases or variants thereof derived from organisms other than these organisms [for example, non-human mammals (for example, mouse, rat, hamster, pig, dog, and the like), birds, reptiles, amphibians, fishes, insects and the like].

The polypeptides of (C) described above (optionally referred to as "homologous polypeptides" hereinafter) are not limited so far as the polypeptides have 80% or higher identity with respect to the amino acid sequence represented by a phospholipase, but preferably 85% or higher, more preferably 90% or higher, even more preferably 95% or higher, further more preferably 98% or higher, particularly preferably 99% or higher identity to the amino acid sequence represented by a phospholipase, and have substantially the same activity as the phospholipase.

Any of values for "identity" used herein can be values calculated using a homology search program well known to a person skilled in the art, and for example, values can be calculated by the homology algorithm BLAST (Basic local alignment search tool) http://www.ncbi.nlm.nih.gov/BLAST/provided by National Center for Biotechnology Information (NCBI) using default (initially set) parameters. In addition, the homologous polypeptides include salts thereof, polypeptides with or without a disulfide bond, phosphorylated or unphosphorylated polypeptides, and, further, polypeptides with or without a sugar chain. Thus, the source of the homologous polypeptides is not limited to human so far as the polypeptides meet these conditions. For example, the homologous polypeptides include phospholipases and variants thereof derived from organisms other than human [for example, mammals other than human (for example, mouse, rat, hamster, pig, dog and the like), birds, reptiles, amphibians, fishes, insects, and the like].

For example, when the polypeptide of (A) described above contains the amino acid sequence of SEQ ID NO: 7, the homologous polypeptide of (C) described above may be a polypeptide comprising any of the amino acid sequences of SEQ ID NOs: 8 to 12. Specifically, the homologous polypeptides of (C) described above are peptides of, for example, Swiss Prot accession numbers: P04054 (human-derived group IB), Q9Z0Y2 (mouse-derived group IB), P04055 (rat-derived Group IB), and P00602 (snake-derived).

The term "variant" used herein refers to "variation", namely, individual variations of the same polypeptide within the same species, or variations of homologous polypeptides between several species.

Moreover, partial polypeptides of the phospholipase of the present invention (namely, phospholipases, modified polypeptides thereof and homologous polypeptides thereof) can be also used so far as the polypeptides have substantially the same activity as the phospholipase. In this case, the number of amino acids composing partial polypeptides is 90%, 80%, 70%, 60%, 50%, 40%, 30%, 20%, 10% or 5% of the number of amino acids of the phospholipase.

Method for Preparing Phospholipase

These phospholipases (namely, phospholipases, modified polypeptides thereof, and homologous polypeptides thereof) and their partial polypeptides of the present invention can be prepared by various publicly known methods, such as genetic engineering methods, and synthetic methods. Specifically, when a genetic engineering method is applied, a desired polypeptide can be prepared by inserting a polynucleotide encoding a phospholipase or its partial peptide into appropriate host cells, culturing the transformants under conditions which enable expression of the gene, and carrying out isolation and purification of the desired polypeptide from the culture using conventional methods for isolation and purification of expressed protein. As the methods for isolation and purification, there can be mentioned salting out with ammonium sulfate, ion-exchange column chromatography using ion-exchange cellulose, molecular sieve column chromatography using molecular sieve gels, affinity column chromatography using protein A-bound polysaccharides, dialysis, lyophilization and the like. In addition, when a synthetic method is applied, conventional methods of synthesis such as a liquid phase method or a solid phase method can be used, and usually an automatic synthesizer can be used. Synthesis of chemically modified compounds can be carried out using conventional methods. Moreover, a desired partial polypeptide can be prepared by enzymatic cleavage using appropriate proteases.

Among the methods for preparation of the phospholipase used in the present invention, genetic engineering methods are described in detail below, and these methods can also be applied for partial polypeptides thereof with no particular limitation so far as the partial polypeptides can be used for the screening which will be described later.

Polynucleotide Encoding Phospholipase

The polynucleotides encoding the phospholipase used in the present invention (namely, phospholipases, modified polypeptides thereof, and homologous polypeptides thereof) are not specifically limited so far as the polynucleotides encode the phospholipases, the modified polypeptides, or the homologous polypeptides.

In addition, the term "polynucleotide" used herein refers to both DNA and RNA. The polynucleotide encoding the phospholipase used in the present invention is specifically selected from the group consisting of (I) to (VI) listed below:

(I) a polynucleotide comprising any of the base sequences identified by the accession numbers described above (preferably any of the base sequences of SEQ ID NOs: 13 to 18);

(II) a polynucleotide encoding the "polypeptide comprising any of the amino acid sequences identified by the accession numbers described above (preferably any of the amino acid sequences of SEQ ID NOs: 7 to 12)";

(III) a polynucleotide encoding the "polypeptide comprising any of the amino acid sequences identified by the accession numbers described above (preferably any of the amino acid sequences of SEQ ID NOs: 7 to 12) and having substantially the same activity as the phospholipase";

(IV) a polynucleotide encoding the "polypeptide comprising any of the amino acid sequences identified by the accession numbers described above (preferably any of the amino acid sequences of SEQ ID NOs: 7 to 12) in which one or several (preferably one or a few) amino acids are deleted, substituted, inserted and/or added at one or several sites (preferably one or a few), and yet having substantially the same activity as the phospholipase";

(V) a polynucleotide that can hybridize with the polynucleotide comprising any of base sequences identified by the accession numbers described above (preferably, any of the base sequences of SEQ ID NOs: 13 to 18) under stringent conditions, and encodes a polypeptide having substantially the same activity as the phospholipase; and (VI) a polynucleotide that has 80% or higher, preferably 85% or higher, more preferably 90% or higher, even more preferably 95% or higher, even further preferably 98% or higher and particularly preferably 99% or higher identity to any of the base sequences identified by the accession numbers described above (preferably any of the base sequences of SEQ ID NOs: 13 to 18) and encodes polypeptides having substantially the same activity as the phospholipase.

Herein, "any of the base sequences identified by the accession numbers described above" refers to the base sequences which are identified by the predetermined publicly-known database based on the accession numbers described above (or the base sequence encoding the amino acid sequence thereby specified), preferably any of the base sequences of SEQ ID NOs: 13 to 18, and more preferably the base sequence of SEQ ID NO: 13.

In an aspect of the present invention, the polynucleotide encoding the phospholipase used in the present invention is a polynucleotide encoding the "polypeptide comprising any of the amino acid sequences identified by the accession numbers described above (preferably any of the amino acid sequences of SEQ ID NOs: 7 to 12) in which one or several (preferably one or a few) amino acids are deleted, substituted, inserted and/or added at one or several sites (preferably one or a few), and yet having substantially the same activity as the phospholipase". Here, the number of amino acids which may be deleted, substituted, inserted and/or added is, for example, 1 to 30, preferably 1 to 20, more preferably 1 to 10, even more preferably 1 to 5, and particularly preferably 1 to 2.

Variants obtained by adding, deleting and/or substituting amino acids can be, for example, prepared by conducting site-specific mutagenesis of DNA encoding the polypeptide using a publicly known method (for example, see Nucleic Acid Research, Vol. 10, No. 20, p. 6487-6500, 1982). The expression "one or several amino acids" used herein refers to a certain number of amino acids that can be added, deleted, inserted and/or substituted by site-specific mutagenesis.

Site-specific mutagenesis can be carried out, for example, using a synthetic oligonucleotide primer that is complementary to a single stranded phage DNA to be mutated, except for a particular inconsistency which is a desired mutation. Namely, a complementary DNA strand is synthesized using the synthetic oligonucleotide as a primer using phage, and host cells are transformed by introducing the obtained double stranded DNA. Cultured transformed bacteria are plated on agar to allow plaque formation from a single cell containing the phage. By this treatment, theoretically, 50% of new colonies contain the phage having the mutated single strand and the remaining 50% contains the original sequence. The plaques thus obtained are hybridized with synthetic probes labeled by kinase treatment at the temperature at which the probe can hybridize with DNA completely having a desired mutation but cannot hybridize with DNA having the original strand. Then, the plaques hybridized with the probe are collected and cultured to recover the DNA.

Moreover, in addition to the above-mentioned site-specific mutagenesis, there are other methods to substitute, delete, insert, and/or add one or several amino acids on amino acid sequences of bioactive peptides of a phospholipase without losing activity thereof, such as a method to treat genes with a mutagen and a method to cleave genes selectively and delete, add, insert and/or substitute selected nucleotides, and then perform ligation.

In this specification, "deletion" includes deletion of terminal amino acid residues of the amino acid sequence, and deletion of amino acid residues in the middle of the amino acid sequence.

The term "addition" includes addition of amino acid residues at a terminal of the amino acid sequence and deletion of amino acid residues in the middle of the amino acid residues.

There are multiple codons encoding one amino acid. Therefore, any DNA encoding any of the amino acid sequences identified by the accession numbers described above (preferably the amino acid sequences of SEQ ID NOs: 7 to 12), or any DNA encoding the domain having enzyme activity thereof are included within the range of the present invention.

In another aspect of the present invention, a polynucleotide encoding the phospholipase used in the invention can hybridize with a polynucleotide comprising any of the base sequences identified by the accession numbers described above (preferably any of the base sequences of SEQ ID NOs: 7 to 12) under stringent conditions and encodes a polypeptide having substantially the same activity as the phospholipase. Specifically, it refers to a polynucleotides comprising a sequence other than any of the base sequences identified by the accession numbers described above and is identified by any of SEQ ID NOs: 13 to 18 (derived from human, mouse, rat, pig, bee, and the like).

The expression "polynucleotide which can hybridize under stringent conditions" herein used refers to specifically, for example, polynucleotides having at least 70% or higher, preferably 80% or higher, more preferably 85% or higher, even more preferably 90% or higher and even further preferably 95% or higher and particularly preferably 98% or higher and most preferably 99% or higher identity to the base sequences of SEQ ID NOs: 13 to 18 when calculated by homology search software such as FASTA, BLAST, Smith-Waterman [Meth. Enzym., 164, 765 (1988)] using default (initially set) parameters. Moreover, as "stringent hybridization conditions", there can be mentioned, for example, "2×SSC, 0.1% SDS, 50° C.", "2×SSC, 0.1% SDS, 42° C.", and "1×SSC, 0.1% SDS, 37° C." and as more stringent conditions, there can be mentioned, for example, "2×SSC, 0.1% SDS, 65° C.", "0.5×SSC, 0.1% SDS, 42° C.", and "0.2×SSC, 0.1% SDS, 65° C.". In more detail, as a method using Rapid-hyb buffer (Amersham Life Science Inc.), it can be considered to carry out pre-hybridizing at 68° C. for 30 min or more, then adding probes, and hybridizing at 68° C. for one hour or more followed by washing three times in 2×SSC and 0.1% SDS at room temperature for 20 min, three times in 1×SSC, 0.1% SDS at 37° C. for 20 min, and finally twice in 1×SSC, 0.1% SDS at 50° C. for 20 min. Alternatively, for example, pre-hybridization can be carried out in Expresshyb Hybridization Solution (Clontech Company) at 55° C. for 30 min or more, then adding labeled probes, incubating at 37 to 55° C. for 1 hour or more, and washing three times in 2×SSC, 0.1% SDS, at room temperature for 20 min, and once in 1×SSC, 0.1% SDS, at 37° C. for 20 min. Here, conditions can be made more stringent by raising temperature for pre-hybridization, hybridization, and the second washing. For example, temperature for pre-hybridization or hybridization can be 60° C., or 68° C. for even more stringent conditions. A person skilled in the art can set a condition to obtain isoforms and allelic variants of a phospholipase, and corresponding genes derived from other species by taking into account other conditions such as probe concentration, probe length, and incubation time in addition to conditions such as salt concentration of buffer and temperature.

Detailed procedures of a hybridization method can be found in "Molecular Cloning, A Laboratory Manual 2nd ed." (Cold Spring Harbor Press (1989); in particular, Section 9.47-9.58), "Current Protocols in Molecular Biology" (John Wiley & Sons (1987-1997); in particular, Section 6.3-6.4, and "DNA Cloning 1: Core Techniques, A Practical Approach 2nd Ed." (Oxford University (1995); in particular, Section 2.10 for experimental conditions). As polynucleotides to be hybridized, there can be mentioned polynucleotides comprising the base sequences having at least 50% or higher, preferably 70% or higher, more preferably 80% or higher, even more preferably 90% or higher (for example, 95% or higher or even 99% or higher) identity to the base sequences comprising the bases of SEQ ID NOs: 13 to 18. The degree of identity can be determined by BLAST algorithm (Altschul (1990) Proc. Natl. Acad. Sci. USA 87: 2264-8; Karlin and Altschul (1993) Proc. Natl. Acad. Sci. USA 90: 5873-7) in the same way as determination of homology as described above. Other than the above-mentioned BLASTN program for base sequence described above, other programs to determine identity of amino acid sequence based on this algorithm, such as BLASTIX (Altschul et al. (1990) J. Mol. Biol. 215: 403-10), have been developed and available.

In addition, by polymerase chain reaction (PCR) (Current Protocols in Molecular Biology, John Wiley & Sons (1987) Section 6.1-6.4), isoforms and allelic variants of a phospholipase, and the like can be obtained from cDNA libraries and genome libraries of human, mouse, rat, rabbit, hamster, chicken, pig, bovine, goat, sheep, snake, honey bee, and the like, using primers designed based on the base sequences of SEQ ID NOs: 13 to 18.

The base sequence of a polynucleotide can be confirmed by determining the sequence using a conventional method. For example, confirmation can be made using a method such as the dideoxynucleotide chain termination method (Sanger et al. (1977) Proc. Natl. Acad. Sci. USA 74: 5463). Moreover, the sequence can be also analyzed using an appropriate DNA sequencer.

The polynucleotide encoding the phospholipase used in the present invention can be, for example, naturally occurring or completely synthetic. Furthermore, the polynucleotide can be synthesized from a part of a naturally occurring nucleotide. As typical methods to acquire the polynucleotide encoding the phospholipase used in the present invention, there can be mentioned, for example, a method to screen from commercially available libraries or cDNA libraries using conventionally used genetic engineering techniques, such as using an appropriate DNA probe prepared based on the information of the sequence represented by a partial polynucleotide.

The polynucleotide encoding the phospholipase used in the present invention is preferably a "polynucleotide comprising any of the base sequences identified by the accession numbers described above (for example, the base sequence of SEQ ID NO: 13). The base sequence of SEQ ID NO: 13 has an open reading frame that starts with ATG at positions 441 to 443 and ends with TAA at positions 936 to 938. In addition, polynucleotides comprising the base sequences of SEQ ID NOs: 14 to 18 can be mentioned.

Plasmids

As a method to incorporate the DNA fragment of the present invention into plasmids, there can be mentioned, for example, a method described by Sambrook, et al. in Molecular Cloning, A Laboratory Manual, second edition, Cold Spring Harbor Laboratory, 1.53 (1989). Conveniently, commercially available ligation kits (for example, products by Takara Shuzo Co., Ltd. and the like) can also be used. Recombinant plasmids thus prepared are introduced into host cells (for example, *E. coli* TBI, LE392, XL-1Bluc or the like). Plasmids used for transformation are not specifically limited to any particular plasmid so far as the polynucleotides encoding the phospholipases are contained, and plasmids prepared by inserting those polynucleotides into publicly known vectors selected appropriately according to host cells to be used can be mentioned. For example, a phospholipase alone, or a fusion protein of a phospholipase and a protein tag (for example, histidine tag, FLAG tag, glutathione-S-transferase (GST), maltose binding protein (MBP)) can be incorporated into expression vectors.

Vectors can be conveniently prepared by a conventional method by linking a desired gene into a vector for recombination (plasmid DNA) available in the art. Examples of the vector used herein are specifically but not limited to *Escherichia coli* derived plasmids such as pBluescript, pUC18, pUC19, and pBR322.

Expression vectors are particularly useful for the production of desired proteins. Expression vectors which can express a desired gene and produce a desired protein in a variety of host cells including prokaryotic cells and/or eukaryotic cells can be employed without any restriction. However, for example, preferred expression vectors for *Escherichia coli* include pQE-30, pQE-60, pMAL-C2, pMAL-p2, and pSE420, and preferred expression vectors for yeast include pYES2 (the genus of *Saccharomyces*), pPIC3.5K, pPIC9K, pAO815 (these four are the genus of *Pichia*), pBacPAK8/9, pBK283, pVL1392, pBlueBac4.5.

Transformants

The transformant can be prepared by introducing the desired expression vector into host cells. Host cells used are not specifically limited so far as cells are compatible with the expression vectors of the present invention and able to be transformed, and a variety of cells conventionally used in the art of the present invention including natural cells or artificially established recombinant cells can be used. For example, bacterial cells (the genus of *Escherichia* and *Bacillus*), yeast cells (the genus of *Saccharomyces, Pichia*, and the like), animal cells, insect cells, and plant cells can be mentioned.

In particular, *Escherichia coli*, yeast or insect cells are preferred. Specifically, *Escherichia coli* (M15, JM109, and the like), yeast (INVSc1 (the genus of *Saccharomyces*), GS115, KM71 (these two are the genus of *Pichia*), and the like), insect cells (BmN4, silkworm larva and the like) are illustrated. In addition, as animal cells, cells derived from mouse, rat, hamster, monkey or human or cultured cell lines established are illustrated. Further, plant cells are not specifically limited so far as they can be cultured, and for example, cells derived from tobacco, plants of the genus of *Arabidopsis*, rice, corn and wheat are illustrated.

For the vector of the present invention, a methionine codon (ATG) is illustrated as a suitable initiation codon and a common termination codon (for example, TAA, TAG, TGA and the like) is illustrated as a termination codon.

The expression vector can be prepared by linking at least a promoter, an initiation codon, a desired gene, a termination codon and a terminator region continuously and circularly to an appropriate unit capable of replication. Herein, if desired, appropriate DNA fragments (for example, linker or other restriction sites, and the like) can be employed by conventional methods such as digestion by a restriction enzyme or ligation using T4DNA ligase.

Introduction of the expression vector used in the present invention into host cells [transformation (transduction)] can be achieved using publicly known conventional methods. For example, bacterial cells (*E. coli, Bacillus subtilis*, or the like) can be transformed using the method by Cohen et al. [Proc. Natl. Acad. Sci. USA, 69, 2110 (1972)], the protoplast method [Mol. Gen. Genet., 168, 111 (1979)], or the competent method [J. Mol. Biol., 56, 209 (1971)]. Saccharomyces cerevisiae can be transformed, for example, using the method by Hinnen et al. [Proc. Natl. Acad. Sci. USA, 75, 1927 (1978)] or the lithium method [J. Bacteriol., 153, 163 (1983)]. Animal cells can be transformed, for example, using the method by Graham [Virology, 52, 456 (1973)], and insect cells can be transformed, using, for example, the method by Summers et al. [Mol. Cell. Biol., 3, 2156-2165, (1983)], respectively. Plant cells can be transformed by the method using Agrobacterium bacteria (Horsch et al., Science, 227, 129 (1985), Hiei et al., Plant J., 6, 271-282 (1994)), the electroporation method (Fromm et al., Nature, 319, 791 (1986)), the PEG method (Paszkowski et al., EMBO J., 3, 2717 (1984)), the microinjection method (Crossway et al., Mol. Gen. Genet., 202, 179 (1986)), or the particle acceleration method (McCabe et al., Bio/Technology, 6, 923 (1988)).

In the present invention, a phospholipase can be expressed (produced), for example, by culturing the transformed cells comprising the expression vector prepared as described above in a nutrient medium. Preferably, the nutrient medium contains carbon sources and inorganic nitrogen sources or organic nitrogen sources required for the growth of host cells (transformants). Examples of the carbon sources are glucose, dextran, soluble starch, sucrose, and methanol. Examples of the inorganic or organic nitrogen sources are ammonium salts, nitrates, amino acids, corn steep liquor, peptone, casein, meat extracts, soybean waste, and potato extracts. In addition, if desired, the medium may contain other nutrients (for example, inorganic salts (for example, sodium chloride, calcium chloride, sodium dihydrogenphosphate, and magnesium chloride), vitamins, antibiotics (for example, tetracycline, neomycin, ampicillin, and kanamycin). Culture is carried out using a well known method in the art. Culture conditions such as temperature, medium pH, and culture time are appropriately selected to enable cells to produce a large amount of proteins of the present invention.

Specific culture media and culture conditions used for host cells are illustrated below, but not limited to those illustrated. When bacteria, Actinomyces, yeasts, or filamentous bacteria are used as host cells, for example, liquid media comprising the nutrient sources described above are suitable. Preferably, examples of the media at pH 5 to 8 are LB medium and M9 medium (Miller et al., Exp. Mol. Genet., Cold Spring Harbor Laboratory, p. 431, 1972). Using these media, cell culture can be carried out usually at 14 to 43° C. for about 3 to 24 hours under aeration and stirring, as required. When bacteria of genus *Bacillus* are used as host cells, the cells are usually cultured at 30 to 40° C. for about 16 to 96 hours under aeration and stirring, if necessary.

When yeast cells are used as host cells, culture media such as Burkholder minimum medium (Bostian, Proc. Natl. Acad. Sci. USA., Vol. 77, p. 4505, 1980) can be used desirably at pH 5 to 8. Cell culture is usually carried out at about 20 to 35° C. for about 14 to 144 hours and aeration and stirring can also be applied as needed. When animal cells are used as host cells, for example, MEM medium (Science, Vol. 122, p. 501, 1952), DMEM medium (Virology, Vol. 8, p. 396, 1959), PRMI1640 medium (J. Am. Med. Assoc., Vol. 199, p. 519, 1967), and 199 medium (Proc. Soc. Exp. Biol. Med., Vol. 73, p. 1, 1959) and the like comprising about 5 to 20% of fetal bovine serum can be used. Medium pH of about 6 to 8 is preferred. Culture is usually carried out at 30 to 40° C. for about 15 to 72 hours, and aeration and stirring can also be applied as needed.

When insect cells are used as host cells, for example, Grace's medium (Proc. Natl. Acad. Sci. USA., Vol. 82, p. 8404, 1985) comprising fetal bovine serum can be mentioned and the medium pH of about 5 to 8 is preferred. Culture is usually carried out at 20 to 40° C. for about 15 to 100 hours, and aeration and stirring can also be applied as needed.

Methods for expression and purification of a phospholipase are found in a number of publicly known literatures (for example, Kohji Hanasaki, et al., The Journal of Biological Chemistry 274 (48), 34203-34211, 1999, and the like).

Methods for purification of a desired polypeptide from a culture (expressing cells or culture supernatant) of transformants are, for example, salting out with ammonium sulfate, ion-exchange column chromatography using a ion-exchange cellulose, molecular sieve column chromatography using molecular sieve gel, affinity column chromatography using protein A-linked polysaccharides, dialysis, lyophilization, or the like. In addition, for synthetic methods, conventional methods such as liquid phase synthesis or solid phase synthesis can be applied, and usually an automatic synthesizer can be used. Synthesis of chemically modified products can be carried out using conventional methods. Moreover, a desired partial polypeptide can be prepared by enzymatic cleavage using appropriate proteases.

The phospholipase used in the present invention may be a salt thereof. Herein, "salt" refers to pharmaceutically acceptable salts which are not specifically limited so far as they are pharmaceutically acceptable salts with phospholipase. Specific examples include hydrohalide salts (for example, hydrofluoride, hydrochloride, hydrobromide, and hydroiodide), inorganic acid salts (for example, sulfates, nitrates, perchlorates, phosphates, carbonates, and bicarbonates), organic carboxylates (for example, acetates, oxalates, maleates, tartrates, fumarates, and citrates), organic sulfonates (for example, methanesulfonates, trifluoromethanesulfonates, ethanesulfonates, benzenesulfonates, toluenesulfonates, and camphorsulfonates), amino acid salts (for example, aspartates and glutamates), quaternary amines, alkaline metal salts (for example, sodium salts, potassium salts),and alkaline earth metal salts (for example, magnesium salts, calcium salts).

The phospholipase used in the present invention has a stimulating activity of GPR40, and a fragment of the phospholipase can be used so far as the fragment has substantially the same activity as the phospholipase.

The expression that the above described fragment "having substantially the same activity as the phospholipase" used herein means that the fragment has a signal transduction activity mediated by GPR40, in more detail, the fragment has a cell stimulating activity on cells expressing GPR40 (for example, activity measured by the reporter assay system that can detect changes in translation and transcription of reporter genes due to production of signaling substances, intracellular $Ca^{2+}$ release, activation of adenylate cyclase, intracellular cAMP production, intracellular cGMP production, release of arachidonic acid, release of acetylcholine, production of inositol phosphate, changes in cell membrane potential, phosphorylation or activation of intracellular proteins, pH changing activity, phosphorylation or activation of MAP kinase, activation of c-fos, glycerol production activity, lipolysis activity, insulin secretion activity, and cell proliferation activity). "Substantially the same" means that the activity is qualitatively the same. In other words, in order to have "substantially the same activity as the phospholipase", the activity is preferably equivalent (for example, about 0.01 to 100 folds, preferably 0.05 to 20 folds, more preferably 0.5 to 2 folds). These activities can be measured by conventional methods, for example, using the methods described in Examples below.
GPR40

GPR40 used for screening in the present invention is not particularly limited in terms of source thereof so far as it has an activation effect in response to a phospholipase (for example, sPLA2) and a cell stimulating activity of cells expressing GPR40 (for example, activity measured by the reporter assay system that can detect changes in translation and transcription of reporter genes due to production of signaling substances, intracellular $Ca^{2+}$ release, activation of adenylate cyclase, intracellular cAMP production, intracellular cGMP production, release of arachidonic acid, release of acetylcholine, production of inositol phosphate, changes in cell membrane potential, phosphorylation or activation of intracellular proteins, pH changing activity, phosphorylation or activation of MAP kinase, activation of c-fos, glycerol production activity, lipolysis activity, insulin secretion activity, and cell proliferation activity), and for example, it includes GPR40 derived from natural sources such as GPR40 expressing organs, tissues and cells, and artificially prepared GPR40 using well known genetic engineering methods or synthetic methods. In addition, a partial polypeptide of GPR40 is not specifically limited so far as it can be used for screening as described below, for example, a partial polypeptide which has a cell stimulating activity of a phospholipase and a polypeptide comprising the amino acid sequence corresponding to the extracellular region can be used.

Specifically, GPR40 used for screening of the present invention is one of the G-protein coupled receptor proteins and is polypeptides whose amino acid sequences (derived from human, mouse and rat) and encoding DNA sequences have been reported [for example, GenBank accession number NP_005294 (human), NP_918946 (mouse), and XP_695216 (rat)]. Specifically, GPR40 is a polypeptide selected from the group consisting of:

(a) a polypeptide comprising the amino acid sequence of SEQ ID NO: 2;

(b) a polypeptide comprising the amino acid sequence of SEQ ID NO: 2 in which one or several (preferably one or a few) amino acids are substituted, deleted, inserted and/or added, and having substantially the same activity as GPR40;

(c) a polypeptide comprising the amino acid sequence having 80% or higher identity to the amino acid sequence of SEQ ID NO: 2;

(d) a polypeptide encoded by a polynucleotide which can hybridize with a polynucleotide comprising the base sequence of SEQ ID NO: 1 under stringent conditions and having substantially the same activity as GPR40;

(e) a polypeptide encoded by a polynucleotide consisting of the base sequences having 80% or higher (preferably 85% or higher, more preferably 90% or higher, even more preferably 95% or higher, further more preferably 98% or higher, particularly preferably 99% or higher) identity to the base sequence of SEQ ID NO: 1 and having substantially the same activity as GPR40.

For GPR40 used in the present invention, a "polypeptide comprising the amino acid sequence of SEQ ID NO: 2" is preferred. In addition, the polypeptide includes salts thereof, polypeptides with or without a disulfide bond, phosphorylated or unphosphorylated polypeptides, and further polypeptides with or without a sugar chain.

The polypeptide "having substantially the same activity as GPR40" used herein refers to a polypeptides having an activation effect in response to a phospholipase (for example, sPLA2) and having GPR40 mediated signal transduction effects, in more detail, cell stimulating activity on GPR40 expressing cells (for example, activity measured by the reporter assay system that can detect changes in translation and transcription of reporter genes due to production of signaling substances, intracellular $Ca^{2+}$ release, activation of adenylate cyclase, intracellular cAMP production, intracellular cGMP production, release of arachidonic acid, release of acetylcholine, production of inositol phosphate, changes in cell membrane potential, phosphorylation or activation of intracellular proteins, pH changing activity, phosphorylation or activation of MAP kinase, activation of c-fos, glycerol production activity, lipolysis activity, insulin secretion activity, and cell proliferation activity). In addition, "substantially the same" means that the activity is qualitatively the same. In other words, in order to "have substantially the same activity as GPR40", the activity is preferably equivalent (for example, about 0.01 to 100 folds, preferably 0.05 to 20 folds, more preferably 0.5 to 2 folds) to the activity of GPR40. These activities can be measured using conventional methods, for example, using the methods described in Examples below.

In a preferred aspect of the present invention, the polypeptide of (b) (optionally referred to as "modified polypeptide" hereinafter) can be polypeptides containing the amino acid sequence of SEQ ID NO: 2 in which the amino acid sequence has one or several (preferably one or a few) conservative substitutions and yet having substantially the same activity as GPR40.

"Conservative substitution" used herein means that one or several (preferably a few) amino acid residues are substituted with other chemically similar amino acid residues without substantially altering peptide activity. For example, there can be mentioned a case where a hydrophobic residue is substituted by another hydrophobic residue, or a case where a polar residue is substituted by another polar residue having the same charges. Functionally similar amino acids with which such substitution can be made are publicly known for each amino acid in the art. Specific examples of non-polar (hydrophobic) amino acids are alanine, valine, isoleucine, leucine, proline, tryptophan, phenylalanine, and methionine. Examples of polar (neutral) amino acid include glycine, serine, threonine, tyrosine, glutamine, asparagine, and cysteine. Examples of positively charged (basic) amino acid include arginine, histidine, and lysine. In addition, examples of negatively charged (acidic) amino acid include aspartic acid and glutamic acid.

Here, the number of amino acids which can be deleted, substituted, inserted and/or added is, for example, 1 to 30, preferably 1 to 20, more preferably 1 to 10, even more preferably 1 to 5, and particularly preferably 1 to 2. In addition, the modified polypeptide includes salts thereof, polypeptides with or without a disulfide bond, phosphorylated or unphosphorylated polypeptides, and, further polypeptides with or without a sugar chain. Accordingly, sources of the modified polypeptide is not limited to human so far as these conditions are satisfied.

The modified polypeptide may further include polypeptides with modification or alteration at the N-terminal (amino terminal) and the C-terminal (carboxyl terminal). For example, the C-terminal carboxyl group can be carboxylate (—COO−), amide (—CONH$_2$), or ester (—COOR). Here, the R may be, for example, a linear, branched, or cyclic C1-6 alkyl group and a C6-12 aryl group. In addition, the modified polypeptide may include polypeptides with an N-terminal amino group protected by a common protective group.

Examples of the polypeptide of (b) include GPR40 or variants thereof derived from organisms other than human [for example, mammals other than human (for example, mouse, rat, hamster, pig, dog, and the like), birds, reptiles, amphibians, fishes, insects, and the like]. Specifically, polypeptides comprising the amino acid sequence of SEQ ID NOs: 4 and 6 (derived from mouse and rat) are included.

The polypeptide of (c) (optionally referred to as "homologous polypeptide" hereinafter) is not limited so far as it comprises an amino acid sequence homologous to the amino acid sequence of GPR40 with 80% or higher, preferably 85% or higher, more preferably 90% or higher, even more preferably 95% or higher, even further preferably 98% or higher identity, particularly preferably 99% or higher homology and yet has substantially the same activity as GPR40.

Any of values for "identity" used herein can be values calculated using a homology search program known to a person skilled in the art, and for example, values can be calculated by the homology algorithm BLAST (Basic local alignment search tool) provided by National Center for Biotechnology Information (NCBI) using default (initially set) parameters. In addition, the homologous polypeptide includes salts thereof, polypeptides with or without a disulfide bond, phosphorylated or unphosphorylated polypeptides, and further polypeptides with or without a sugar chain. Accordingly, sources of the homologous polypeptide are not limited to human so far as the polypeptide meets these conditions. For example, GPR40 or variants thereof derived from organisms other than human [for example, mammals other than human (for example, mouse, rat, hamster, pig, dog and the like), birds, reptiles, amphibians, fishes, insects and the like] is included. Specifically, polypeptides comprising the amino acid sequence of SEQ ID NOs: 4 and 6 (derived from mouse and rat) are included.

Furthermore, a partial polypeptide of GPR40 used in the present invention (namely, GPR40, modified polypeptides thereof, or homologous polypeptides thereof) has an effect of activation by a phospholipase (for example, sPLA2) and GPR40 mediated signal transduction effect, in more detail, activity substantially the same as cell stimulating activity on GPR40 expressing cells. Here, active cell stimulating activity means activity measured by the reporter assay system that can detect changes in translation and transcription of reporter genes due to production of signaling substances, intracellular $Ca^{2+}$ release, activation of adenylate cyclase, intracellular cAMP production, intracellular cGMP production, release of arachidonic acid, release of acetylcholine, production of inositol phosphate, changes in cell membrane potential, phosphorylation or activation of intracellular proteins, pH changing activity, phosphorylation or activation of MAP kinase, activation of c-fos, glycerol production activity, lipolysis activity, insulin secretion activity, cell proliferation activity, and the like and partial peptides having these activities are included in the present invention. And substantially the same means that activity is qualitatively the same. In other words, in order to have "substantially the same activity as the GPR40", preferably, the activity is equivalent (for example, about 0.01-100 folds, preferably 0.05-20 folds, more preferably 0.5-2 folds) to the activity of a phospholipase. These activities can be measured by a conventional method, for example, using the method described in Examples below.

Preparation Methods for GPR40

The GPR40 (namely, GPR40, modified polypeptides, and homologous polypeptides) and partial polypeptides thereof used in the present invention can be prepared by various publicly known methods, for example, genetic engineering methods, and synthetic methods. Specifically, when a genetic engineering method is applied, the polypeptides can be prepared by inserting the polynucleotide encoding GPR40 or its partial peptide into appropriate host cells, culturing the obtained transformants under conditions which enable expression of the gene, and carrying out isolation and purification of the desired polypeptide from the culture using conventional methods for isolation and purification of expressed proteins. The methods for isolation and purification include, for example, salting out with ammonium sulfate, ion-exchange column chromatography using ion-exchange cellulose, molecular sieve column chromatography using molecular sieve gels, affinity column chromatography using protein A-bound polysaccharides, dialysis, lyophilization, and the like. In addition, when synthetic methods are applied, conventional methods of synthesis such as a liquid phase method or a solid phase method can be used, and usually an automatic synthesizer can be used. Synthesis of chemically modified compounds can be carried out using conventional methods. Moreover, a desired partial polypeptide can be prepared by enzymatic cleavage using appropriate proteases.

Among the methods for preparation of GPR40 used in the present invention, genetic engineering methods are described in detail below. These methods can be applied to prepare partial polypeptides thereof with no particular limitation so far as partial polypeptides can be used for the screening which will be described later.

Polynucleotides Encoding GPR40

The polynucleotides encoding GPR40 used in the present invention (namely, GPR40, modified polypeptides, and homologous polypeptides) are not specifically limited so far as the polynucleotides encode the GPR40, the modified polypeptides, or the homologous polypeptides.

In addition, the term "polynucleotide" used herein includes both DNA and RNA. A polynucleotide encoding GPR40 used in the present invention is specifically selected from the group consisting of (i) to (vi) listed below:

(i) a polynucleotide comprising the base sequence of SEQ ID NO: 1;

(ii) a polynucleotide encoding the "polypeptide comprising the amino acid sequence of SEQ ID NO: 2";

(iii) a polynucleotide encoding the "polypeptide comprising the amino acid sequence of SEQ ID NO: 2 and yet having substantially the same activity as the GPR40";

(iv) a polynucleotide encoding the "polypeptide comprising the amino acid sequence of SEQ ID NO: 2 in which one or several (preferably one or a few) amino acids are deleted, substituted, inserted and/or added at one or several sites (preferably one or a few), and yet having substantially the same activity as GPR40";

(v) a polynucleotide which can hybridize with the polynucleotide comprising the base sequence of SEQ ID NO: 1 under stringent conditions and encodes a polypeptide having substantially the same activity as GPR40; and (vi) a polynucleotide having 80% or higher, preferably 85% or higher, more preferably 90% or higher, even more preferably 95% or higher, even further preferably 98% or higher and particularly preferably 99% or higher identity to the base sequence of SEQ ID NO: 1 and encoding a polypeptide having substantially the same activity as the GPR40.

In an aspect of the present invention, the polynucleotide encoding GPR40 used in the present invention is a polynucleotide encoding the "polypeptide comprising the amino acid sequence of SEQ ID NO: 2 in which one or several (preferably one or a few) amino acids are deleted, substituted, inserted and/or added at one or several sites (preferably one or a few) and still having substantially the same activity as the GPR40". Here, the number of amino acids which may be deleted, substituted, inserted and/or added is, for example, 1 to 30, preferably 1 to 20, more preferably 1 to 10, even more preferably 1 to 5, and particularly preferably 1 to 2.

Variants obtained by adding, deleting and/or substituting amino acids can be prepared, for example, by conducting site-specific mutagenesis of the DNA encoding the polypeptides, a conventionally known method (for example, see Nucleic Acid Research, Vol. 10, No. 20, p. 6487-6500, 1982). The expression "one or several amino acids" used herein refers to a certain number of amino acids which can be added, deleted, inserted and/or substituted by site-specific mutagenesis.

Site-specific mutagenesis can be carried out, for example, using a synthetic oligonucleotide primer that is complementary to a single stranded phage DNA to be mutated, except for a particular inconsistency which is a desired mutation. Namely, a complementary DNA strand is synthesized by phage using the synthetic oligonucleotide as a primer, and host cells are transformed by introducing the obtained double stranded DNA. Cultured transformed bacteria are plated on agar to allow plaque formation from a single cell comprising the phage. By this treatment, theoretically, 50% of new colonies contain phage having the mutated single strand and another 50% contains the original sequence. The plaques thus obtained are hybridized with a synthetic probe labeled by kinase treatment at the temperature at which the probe can hybridize with DNA completely having a desired mutation but cannot hybridize with DNA having the original strand. Then, the plaques hybridized with the probe are collected and cultured to recover DNA.

Moreover, in addition to the above described site-specific mutagenesis, methods for substituting, deleting, inserting and/or adding one or several amino acids in the amino acid sequence of GPR40 without losing its activity include a method to treat a gene with a mutagen and a method to cleave a gene selectively, and delete, add, insert and/or substitute a selected nucleotide, and then perform ligation.

The term "deletion" includes deletion of amino acid residues at the terminal of the amino acid sequence and deletion of amino acid residues in the middle of the amino acid sequence.

The term "addition" also includes addition of amino acid residues at a terminal of the amino acid sequence and deletion of amino acid residues in the middle of the amino acid residues. There are multiple codons encoding a single amino acid. Accordingly, any DNA encoding of the amino acid sequence of SEQ ID NO: 2, 4, or 6 or the active region thereof is included within the range of the present invention.

According to another aspect of the present invention, the polynucleotide encoding GPR40 used in the present invention encodes a "polynucleotide which can hybridize with the polynucleotide comprising the base sequence of SEQ ID NO: 1 under stringent conditions and encodes a polypeptide having substantially the same activity as the GPR40". Specifically, polynucleotides comprising the base sequence of SEQ ID NOs: 3 and 5 (derived from mouse and rat) are included.

In this specification, a polynucleotide which can hybridize under stringent conditions refers to, specifically, a polynucleotide with at least 70% or higher, preferably 80% or higher, more preferably 85% or higher, even more preferably 90% or higher, further more preferably 95% or higher, particularly preferably 98% or higher, and most preferably 99% or higher identity to the base sequence of SEQ ID NO: 1 when identity is calculated by homology search software such as FASTA, BLAT, Smith-Waterman [Meth. Enzym., 164, 765 (1988)] using default (initially set) parameters. The "stringent" hybridization conditions may be similar to the conditions described above for phospholipase. The section of the phospholipase can be referred for detailed procedure of the hybridization.

In addition, by polymerase chain reaction (PCR) (Current Protocols in Molecular Biology, John Wiley & Sons (1987) Section 6.1-6.4), isoforms and allelic variants of a phospholipase, and the like can be obtained from cDNA libraries and genome libraries of animals such as human, mouse, rat, rabbit, hamster, chicken, pig, bovine, goat, sheep, and the like, using primers designed based on the base sequences of SEQ ID NO: 1, 3, or 5.

The base sequence of a polynucleotide can be confirmed by sequencing using a conventional method. For example, confirmation can be made using the dideoxynucleotide chain termination method (Sanger et al. (1977), Proc. Natl. Acad. Sci. USA 74: 5463) and the like. In addition, the sequence can be also analyzed using an appropriate DNA sequencer.

The polynucleotide encoding GPR40 used in the present invention can be, for example, natural occurring or completely synthetic. Furthermore, the polynucleotide can be synthesized from a part of a natural polynucleotide. Typical methods to obtain a polynucleotide encoding GPR40 of the present invention include, for example, a method to screen from commercially available libraries or cDNA libraries using conventionally used genetic engineering techniques, such as using an appropriate DNA probe prepared based on the information of the sequence represented by a partial polynucleotide (for example, the base sequence of SEQ ID NO: 1).

The polynucleotide encoding GPR40 used in the present invention is preferably a "polynucleotide comprising the base sequence of SEQ ID NO: 1". The base sequence of SEQ ID NO: 1 has an open reading frame which starts with ATG at positions 1 to 3 and ends with TAA at positions 901 to 903. In addition, a polynucleotide comprising the base sequence of SEQ ID NOs: 3 and 5 can be mentioned.

Plasmids

The plasmid used for the transformation is not specifically limited so far as it has the polynucleotide encoding GPR40 as described above, and plasmids prepared by inserting the polynucleotide into a publicly known expression vector appropriately selected depending on the host cell to be used can be mentioned.

Transformants

The above described transformant is not specifically limited so far as it contains the polynucleotide encoding GPR40 as described above, and for example, it can be a transformant in which the polynucleotide of interest is incorporated into chromosome of a host cell, a transformant comprising a plasmid in which the polynucleotide is incorporated, or a transformant which is not expressing GPR40. The transformant can be prepared, for example, by transforming a desired host cell with the plasmid or the polynucleotide itself.

The host cells can include, for example, publicly known microorganisms commonly used such as *Escherichia coli* (for example, *Escherichia coli* JM109), or yeast (for example, *Saccharomyces cerevisiae* W303), or publicly known cultured cells such as animal cells (for example, CHO cells, HEK-293 cells, or COS cells) or insect cells (for example, BmN4 cells, Sf-9 cells).

In addition, the publicly known vectors include, for example, pUC, pTV, pGEX, pKK, or pTrcHis for *Escherichia coli;* pEMBLY or pYES2 for yeast; pcDNA3, pMAMneo, or pBabe-puro for CHO cells, HEK-293 cells, and COS cells; vectors having polyhedrin promoter of Bombix mori nuclear polyhedrosis virus (BmNPV) (for example, pBK283) for BmN4 cells.

Cells containing GPR40 are not specifically limited so far as GPR40 is expressed on the surface of cell membrane, and for example, can be obtained by culturing the transformants (namely, cells transformed by plasmids incorporated with the polynucleotide encoding GPR40) under conditions that enable cells to express GPR40, or by injecting RNA encoding GPR40 into appropriate cells and culturing the cells under conditions that enable cells to express GPR40.

Cell Membrane Fragments

In addition, the cell membrane fragments containing GPR40 used in the present invention can be obtained, for example, by disrupting cells that express GPR40 and separating fractions that are rich in cell membrane. Examples of methods to disrupt cells include a method to smash cells using a homogenizer (for example, Potter-Elvehiem homogenizer), grinding cells with a Waring blender or Polytron (Kinematica Co., Ltd.), disrupting cells using a sonicator, or to eject cells through a narrow nozzle by pressurizing using a French press, or the like. Moreover, methods to fractionate membranes can be, for example, methods for fractionation using centrifugal force such as centrifugal fractionation, or density gradient centrifugation.

Screening Methods

As mentioned above, the present invention provides a method to screen for a substance that alters GPR40 mediated cell stimulating activity, characterized by using a biomembrane containing GPR40 or a cell containing the biomembrane and a phospholipase or a salt thereof. This method comprises making a contact between a biomembrane containing GPR40 or a cell containing the biomembrane and a phospholipase or a salt thereof in the presence and absence of a substance of interest, then measuring cell stimulating activity, and comparing the results of measurement obtained in the presence and absence of a substance of interest.

According to a more preferred aspect of the invention, the method further comprises the step of determining that the substance of interest is a candidate of a substance that alters GPR40 mediated cell stimulating activity when there is a difference between the results obtained in the presence and absence of the substance of interest.

According to this screening method, a substance of interest (test compound) can be screed for a stimulating activity or an inhibitory activity distinctively on GPR40 functions. Namely, this screening method enables screening for a substance that alters the GPR40 mediated cell stimulating activity of phospholipase, specifically, screening for a compound which affects activation of GPR40, more specifically, screening for a substance (agonist) that stimulates GPR40 function, or for a substance that inhibits GPR40 function (an antagonist).

Accordingly, when the cell stimulating activity in the presence of a substance of interest is higher than the cell stimulating activity in the absence of the substance of interest, the substance of interest can be determined as a stimulating substance of GPR40 function (a GPR40 agonist). When the cell stimulating activity in the presence of a substance of interest is lower than the cell stimulating activity in the absence of the substance of interest, the substance of interest can be determined as an inhibitory substance of GPR40 function (a GPR40 antagonist).

According to a preferred aspect of the present invention, the cell stimulating activity can be measured by a reporter assay system that detects changes in translation and transcription of a reporter gene due to production of a signaling substance, or by measuring a parameter selected from the group consisting of release of an intracellular calcium ion, activation of adenylate cyclase, production of intracellular cAMP, production of intracellular cGMP, release of arachidonic acid, release of acetylcholine, production of inositol phosphate, change in cell membrane potential, phosphorylation or activation of an intracellular protein, pH-changing activity, phosphorylation or activation of MAP kinase, activation of c-fos, glycerol-generating activity, lipolytic activity, insulin-secreting activity, and cell-proliferative activity. More preferably, a reporter assay system is used or an increase of intracellular calcium ion concentration can be measured.

In the present invention, for example, a GRP40 mediated increase in intracellular calcium ion concentration or an increase in transcription of a reporter gene can be measured by a publicly known method, and compounds can be screened for a stimulating activity or an inhibitory activity distinctively on GPR40 mediated functions. This aspect uses an increase in intracellular signal transduction caused by the effect of a phospholipase on GPR40, for example, an elevation of intracellular calcium concentration.

For example, when a phospholipase acts on cells derived from mammals (for example, HEK-293 cells or CHO cells) expressing GPR40 on the cell membrane (preferably, overexpressing by introduction of an expression vector containing GPR40), an intracellular $Ca^{2+}$ concentration increases.

When compounds are screened for a stimulating activity on GPR40 functions, a substance of interest alone, instead of a substance capable of activating GPR40 mediated cell stimulation (for example, a phospholipase), may be brought into contact with cells in this screening system to select a compound that elevates intracellular $Ca^{2+}$ concentration.

When compounds are screened for an inhibitory activity on GPR40 functions, a phospholipase or a salt thereof and a substance of interest may be added to the cells for screening. Although an intracellular calcium concentration increases by the effect of the phospholipase, when a substance of interest antagonizes the activity of the phospholipase, elevation of intracellular calcium concentration is suppressed. In this case, the substance of interest can be selected as an inhibitory compound of GPR40 function. In addition, as reported in several articles (Kalindjian S. B. et al., Journal of Medicinal Chemistry, vol. 44 (8), 1125-1133, 2001, Sharma S. K. et al., Journal of Medicinal Chemistry, vol. 44, 2073-2079, 2001, and the like), compounds that were found as an antagonist can be converted into agonists by converting their structural formulae, synthetic development, or the like.

Intracellular calcium concentration can be measured, for example, using a calcium fluorescent probe (for example, Fura-2, and Fluo-3). In addition, commercially available calcium measurement kits can be used.

In the present invention, compounds can also be screened for a stimulating activity or an inhibitory activity distinctively on GPR40 functions using cells expressing GPR40 on the cell membrane (preferably, over-expressing by introduction of an expression vector containing GPR40), and further containing a reporter gene with a cAMP responsive element (CRE) located 5'-upstream (for example, alkaline phosphatase gene, luciferase gene, β-lactamase gene, nitroreductase gene, chloramphenicol acetyltransferase gene, β-galactosidase gene, and the like, or fluorescent protein genes such as green fluorescent protein (GFP) gene)(sometimes referred to as "cells for screening" hereinafter). In this case, activation of transcription of a reporter gene with CRE in the promoter region introduced into the cells for screening caused by intracellular transduction of various signals is utilized.

In the following, procedures to screen compounds for a stimulating activity or an inhibitory activity distinctively on GPR40 functions are described in more detail.

In the above described cells introduced with a reporter gene having CRE in the promoter region, the expression level of the reporter gene increases, for example, when intracellular cAMP concentrations increase or intracellular $Ca^{2+}$ concentrations increase. In addition, activity can be measured while basic cellular cAMP levels are elevated by addition of an adenylate cyclase activation agent (for example, forskolin and the like). Expression levels of a reporter gene product can be measured by measuring luminescence derived from the amount of a luminescent substance produced from a substrate reacted with a reporter gene product which is contained in the cell culture supernatant or in the cell extract, or measuring fluorescence derived from a fluorescent protein produced as a reporter gene.

Moreover, when a phospholipase or a salt thereof is added, intracellular signal transduction is activated (for example, an intracellular $Ca^{2+}$ concentration increases), and as a result, an expression level of a reporter gene product is elevated. Thus, when compounds are screened for a stimulating activity on GPR40 functions, a substance of interest alone, instead of a substance capable of activating GPR40 mediated cell stimulation, may be brought into contact with cells in this screening system to select a compound that elevates an expression level of a reporter gene product.

When compounds are screened for an inhibitory activity on GPR40 functions, a phospholipase or a salt thereof and a substance of interest may be added to cells for screening. In addition, activity can be measured while basic cellular cAMP levels are elevated by an adenylate cyclase activating agent (for example, forskolin and the like). Although an expression level of a reporter gene product increases in the culture supernatant or in the cell by the action of the phospholipase, when a substance of interest antagonizes the action of the phospholipase, an expression of a reporter gene product is suppressed. In this case, the substance of interest can be selected as a compound that inhibits GPR40 functions. In addition, as reported in several articles (Kalindjian S. B. et al., Journal of Medicinal Chemistry, vol. 44 (8), 1125-1133, 2001; Sharma S. K. et al., Journal of Medicinal Chemistry, vol. 44, 2073-2079, 2001; and the like), compounds that were found as an antagonist can be converted into agonists by converting their structural formulae, synthetic development, or the like.

It can be easily confirmed whether an effect of a substance of interest is mediated via GPR40 or not. For example, in parallel with the test using cells for screening (namely, cells expressing GPR40 on the cell membrane and having a reporter gene with CRE located 5'-upstream), a similar test using control cells (for example, cells having a reporter gene with CRE located 5'-upstream but not expressing GPR40 on the cell membrane) is carried out. As a result, when an effect of the substance of interest is not mediated by its binding to GPR40, the same phenomenon in terms of expression levels of the reporter gene product are observed in the cells for screening and the control cells, while when an action of the above described substance of interest is mediated by its binding to GPR40, different phenomena in terms of expression levels of a reporter gene product are observed in the cells for screening and the control cells.

In another aspect of the present invention, a substance that alters binding of a phospholipase to GPR40 can be screened as a substance that alters the GPR40 mediated cell stimulating activity. In this case, the screening method of the present invention comprises the following steps: making contact between a biomembrane containing GPR40 or a cells containing the biomembrane and a phospholipase or a salt thereof in the presence and absence of a substance of interest, measuring an amount of binding of the phospholipase or a salt thereof to the biomembrane containing GPR40 or the cell containing the biomembrane, and comparing the amounts of binding obtained in the presence and absence of the substance of interest. According to this screening method, compounds can be screened for a stimulating activity or an inhibitory activity indistinctively. That is, when the method of this aspect can be applied, screening for a substance that alters the GPR40 mediated cell stimulating activity, specifically, screening for a compound that alters the binding ability of a phospholipase to GPR40, and more specifically, screening for a compound which is capable of stimulating or inhibiting GPR40 function can be carried out.

Specifically, a screening of compounds can be carried out without distinguishing the ability to stimulate or inhibit GPR40 function by making contact between GPR40 and a labeled phospholipase in the presence and absence of a substance of interest, and comparing the amounts of specific binding of the phospholipase to GRP40 under the above conditions. That is, the amount of specific binding of the phospholipase to GPR40 in the presence of a substance of interest decreases as compared to the amount of specific binding of the phospholipase to GPR40 in the absence of the substance of interest, the substance of interest can be determined as a substance that alters the GPR40 mediated cell stimulating activity, specifically, as a compound that alters the binding ability of a phospholipase to GPR40, more specifically, as a GPR40 agonist or a GPR40 antagonist.

When an amount of binding is measured, a phospholipase or its salts can be labeled. The labeling substances include, for example, radio-isotopes, enzymes, fluorescent substances, and luminescent substances. For radio-isotopes, for example, $[^3H]$, $[^{14}C]$, $[^{125}I]$, and $[^{35}S]$ can be used. For the enzymes, for example, β-galactosidase, alkaline phosphatase, peroxidase, and the like can be used. For the fluorescent substances, for example, fluorescent isothiocyanate, BODIPY, and the like can be used. For the luminescent substances, for example, luciferin, lucigenin, and the like can be used. In addition, a chimeric protein between a phospholipase and a marker protein (for example, GFP and the like) can be prepared using genetic engineering methods.

Moreover, since involvement of GPR40 in insulin secretion has been suggested, a compound obtained by the screening method of the present invention can be administered in human or organisms other than human [for example, non-human mammals (for example, bovine, monkey, bird, feline, mouse, rat, hamster, pig, dog, and the like), birds, reptiles, amphibians, fishes, insects and the like] and analysis is conducted using insulin secretion from the pancreatic islet as an index or blood insulin level, a blood glucose level, or the like is measured after administration so that it is possible to confirm and determine whether or not the compound is effective for type I diabetes (insulin dependent diabetes), type II diabetes (non-insulin dependent diabetes), diabetic complications and degenerative diseases (for example, diabetic neuropathy, diabetic nephropathy, diabetic retinopathy, and the like), hyperglycemia, polyuria, ketonemia, acidosis, insulin resistance, impaired glucose tolerance, neurodegenerative diseases, insulinoma, cancers, hyperinsulinemia, hyperglyceridemia, fatty liver, hypoglycemia due to insulin hypersecretion, arteriosclerosis, hyperlipidemia, cerebral stroke, obesity, various diseases induced by diabetes or obesity, and the like. It is also effective to perform tests for measurement of, for example, insulin secretion, blood glucose level, and blood lipid level as an index for screening. The number of administrations of a substance of interest can be once or several times per day, and an administration period of a substance of interest or an observation period can be from one day to several weeks.

The substance of interest used in the present invention can be any kind of compounds and include, for example, expression products of gene libraries, synthetic small molecule libraries, nucleic acids (oligo DNA, oligo RNA), synthetic peptide libraries, antibodies, bacterial secreted substances, cell extracts (microorganisms, plant cells, animal cells), cell culture supernatants (microorganisms, plant cells, animal cells), purified or partially purified polypeptides, extracts derived from marine organisms, plants or animals, soil, and random phage peptide display libraries.

Screening Kit

A screening kit according to the present invention contains at least a biomembrane containing GPR40 or a cell containing the biomembrane and a phospholipase or a salt thereof. Preferably, this kit is for screening a substance that alters GPR40 mediated cell stimulating activity. The screening kit may further contain, if desired, various reagents to implement the screening method of the present invention, for example, buffer solutions for binding reaction, buffer solutions for washing, instructions and/or apparatuses, and the like.

The screening kit according to another aspect of the present invention contains at least a phospholipase or a salt thereof and a cell expressing GPR40 on the cell membrane (preferably, over-expressing by introduction of an expression vector containing GPR40) and containing a reporter gene with cAMP responsive element (CRE) located 5' upstream (for example, alkaline phosphatase gene, luciferase gene, and the like). The screening kit can further contain, if desired, various reagents such as, for example, substrates for reporter gene products (for example, alkaline phosphatase or luciferase, or the like), adenylate cyclase activation agents (for example, forskolin), buffer solutions for binding reaction, buffer solutions for washing, instructions and/or apparatuses. In addition, the screening kit may contain a cell having a reporter gene with CRE located 5'-upstream but not expressing GPR40 on the cell membrane as a control.

The screening kit according to another aspect of the present invention contains at least a phospholipase or a salt thereof and a cell expressing GPR40 on the cell membrane (preferably, over-expressing by introduction of an expression vector containing GPR40). The screening kit can further contain, if desired, various reagents such as, for example, calcium fluorescent probes (for example, Fura-2 and the like), buffer solutions for reaction, buffer solutions for washing, instructions, and/or apparatuses. In addition, the screening kit may contain a cell not expressing GPR40 on the cell membrane as a control.

Medicament Comprising a Compound Obtained by the Screening Method of the Present Invention GPR40 has been reported to be highly expressed in pancreatic β cells and its involvement in an effect of promoting insulin secretion from the mouse pancreatic β cell-derived cell strain MIN6 and primary culture cells of the pancreas has been reported (International Publication WO2003/068959 pamphlet; Ito Y et al., Nature, 422 (6928): 173-6, 2003). Insulin has effects of regulation of blood glucose level, storage of triglyceride, regulation of blood fatty acid level, and the like. In addition, GPR40 has been reported to be involved in proliferation of breast cancer (Hardy S et al., The Journal of Biological Chemistry, 280 (14): 13285-91, 2005). Further, it has been reported that hyperinsulinemia, fatty liver, hyperglyceridemia, and the like caused by obesity are alleviated in mice with a reduced expression of GPR40 (Steneberg P et al., Cell Metabolism, 1 (4): 245-58, 2005). Based on these findings, it is expected that GPR40 is involved in type I diabetes (insulin dependent diabetes), type II diabetes (non insulin dependent diabetes), diabetic complications and degenerative diseases (for example, diabetic neuropathy, diabetic nephropathy, diabetic retinopathy, and the like), hyperglycemia, polyuria, ketonemia, acidosis, insulin resistance, impaired glucose tolerance, neurodegenerative diseases, insulinoma, cancers, hyperinsulinemia, hyperglyceridemia, fatty liver, hypoglycemia due to insulin hypersecretion, arteriosclerosis, hyperlipidemia, cerebral stroke, obesity, various diseases induced by diabetes or obesity, and the like.

Accordingly, a compound obtained by the screening method according to the present invention can be used as a medicament for the treatment of type I diabetes (insulin dependent diabetes), type II diabetes (non insulin dependent diabetes), diabetic complications and degenerative diseases (for example, diabetic neuropathy, diabetic nephropathy, diabetic retinopathy, and the like), hyperglycemia, polyuria, ketonemia, acidosis, insulin resistance, impaired glucose tolerance, neurodegenerative diseases, insulinoma, cancers, hyperinsulinemia, hyperglyceridemia, fatty liver, hypoglycemia due to insulin hypersecretion, arteriosclerosis, hyperlipidemia, cerebral stroke, obesity, various diseases induced by diabetes or obesity, and the like.

The compound of interest may form a salt thereof, and the compounds or a salt thereof may form a solvate (for example, hydrates, alcohol hydrates and ether hydrates). Here, the "salt" refers to pharmacologically acceptable salts and is not specifically limited so long as it can be formed as a pharmacologically acceptable salt with a compound obtained by the screening method of the present invention. Specifically, the salts include, preferably, hydrohalide salts (for example, hydrofluoride, hydrochloride, hydrobromide, hydroiodide, and the like), inorganic acid salts (for example, sulfates, nitrates, perchlorates, phosphates, carbonates, bicarbonates, and the like), organic carboxylates (for example, acetates, oxalates, maleates, tartrates, fumarates, citrates, and the like), organic sulfonates (for example, methanesulfonates, trifluoromethanesulfonates, ethanesulfonates, benzenesulfonates, toluenesulfonates, camphorsulfonates, and the like), amino acid salts (for example, aspartates, glutamates and the like), quaternary amine salts, alkaline metal salts (for example, sodium salts, potassium salts, and the like), and alkaline earth metal salts (for example, magnesium salts, calcium salts, and the like).

Although the compound obtained by the screening method of the present invention can be used alone, the compound can be used as pharmaceutical compositions by combining with pharmacologically acceptable carriers. Here, the ratio of an active ingredient to carriers may vary from 1 to 90 wt %. The pharmaceutical composition can be administered to human or organisms other than human [for example, non-human mammals (for example, bovine, monkey, bird, cat mouse, rat, hamster, pig, dog and the like), birds, reptiles, amphibians, fishes, insects and the like] in a variety of dosage forms by either oral or parenteral (for example, intravenous injection, intramuscular injection, subcutaneous administration, rectal administration, transdermal administration). Accordingly, the pharmaceutical composition containing a compound obtained by the screening method of the present invention can be formulated into appropriate dosage forms depending on its administration route, and the dosage forms include, specifically, oral forms such as tablets, capsules, granules, powders and syrups, or parenteral forms such as injections, drip injections, liposomes, or suppositories. These formulations can use commonly used excipients, binders, disintegrators, lubricants, coloring agents, flavoring agents, and, if necessary, stabilizers, emulsifiers, absorption stimulators, surfactants, pH adjusters, antiseptics, antioxidants, extenders, wetting agents, surfactants, dispersing agents, buffering agents, preservatives, dissolution aids, soothing agents, and the like, and can be formulated by combining with ingredients generally used for pharmaceutical formulations using a conventional method. These usable and non-toxic ingredients include, for example, plant and animal oils such as soybean oil, beef tallow, synthetic glycerides, and the like; hydrocarbons, for example, liquid paraffin, squalane, solid paraffin, and the like; ester oils, for example, octyl decyl myristate, isopropyl myristate, and the like; higher alcohols, for example, cetostearyl alcohol, behenyl alcohol, and the like; silicone resins; silicone oils; surfactants, for example, polyoxyethylene fatty acid esters, sorbitan fatty acid esters, glycerin fatty acid esters, polyoxyethylene sorbitan fatty acid esters, polyoxyethylene cured castor oil, polyoxyethylene/polyoxypropylene block polymers, and the like; water soluble polymers, for example, hydroxyethyl cellulose, polyacrylic acid, carboxyvinyl polymer, polyethylene glycol, polyvinylpyrrolidone, methyl cellulose and the like; lower alcohols, for example, ethanol, isopropylalcohol and the like;

polyvalent alcohols (polyols, for example, glycerin, propyleneglycol, dipropyleneglycol, sorbitol, polyethyleneglycol, and the like; saccharides, for example, glucose, sucrose, and the like; inorganic powders, for example, silicic anhydride, aluminum magnesium silicate, aluminum silicate, and the like; inorganic salts, for example, sodium chloride, sodium phosphate, and the like; and purified water and the like using a conventional method. The above described usable and non-toxic excipients include, for example, lactose, fructose, corn starch, sucrose, glucose, mannitol, sorbit, crystalline cellulose, silicone dioxide, and the like. The binders include, for example, polyvinyl alcohol, polyvinyl ether, methylcellulose, ethylcellulose, gum Arabic, tragacanth, gelatin, shellac, hydroxypropylmethylcellulose, hydroxypropylcellulose, polyvinylpyrrolidone, polypropylene glycol/polyoxyethylene block polymer, meglumine, and the like. The disintegrators include, for example, starch, agar, gelatin powder, crystalline cellulose, calcium carbonate, sodium bicarbonate, calcium citrate, dextrin, pectin, carboxymethylcellulose calcium, and the like. The lubricants include, for example, magnesium stearate, talc, polyethylene glycol, silica, cured plant oils, and the like. The coloring agents include additives approved for pharmaceutical use. The flavoring agents include cocoa powder, menthol, empasm, peppermint oil, borneol, cinnamon powder, and the like. The ingredients listed above can be salts thereof or hydrates thereof.

Dosage forms and/or a required dosage range thereof depend on a selection of a compound obtained by the screening method of the present invention, a subject to be administered, administration route, properties of a formulation, patient's conditions and physician's judgment. However, the range of appropriate dose is, for example, about 1.0 to 1,500 μg per kg body weight of a patient, preferably, about 10 to 500 μg per kg body weight of a patient. Considering that efficiency differs depending on administration route, doses required are predicted to vary in a wide range. For example, a higher dosage will be required for oral administration than for intravenous injection. These variations in dose can be adjusted using standard empirical optimization procedures well appreciated in the art.

"Treatment" used in the present specification generally means that a desired pharmacological effect and/or physiological effect is obtained. The effect is preventive in terms that disease and/or symptom is completely or partially prevented and therapeutic in terms that adverse influence of a disease and/or symptom is partially or completely cured. "Treatment" used in the present specification includes arbitrary treatments of a disease of mammals, especially human and includes, for example, (1A) prevention of the onset of a disease or symptom in a patient who may have predisposition of the disease or symptom but who has not been diagnosed to have the predisposition;

(1B) inhibition of disease symptoms, that is, suppression or retardation of the progress thereof;

(1C) alleviation of disease symptoms, that is, regression of a disease or symptoms, or reversion of the progress of symptom, and the like.

EXAMPLES

The present invention will be described in detail in the following with examples which are not intended to limit the invention.

Example 1

Preparation of a Polynucleotide Encoding GPR40

In order to isolate a polynucleotide encoding human GPR40 (optionally referred simply to as GPR40 or hGPR40 hereinafter), PCR primers, a 5'-primer (5'-ttgatatcgccgccaccatggacctgccccccgcagct-3') (SEQ ID NO: 19) and a 3'-primer (5'-ttacttctgggacttgccccctt-3') (SEQ ID NO: 20), were designed based on the 903 by nucleic acid sequence of SEQ ID NO: 1 according to an ordinary method. PCR was carried out at 94° C. for 5 min followed by repeating 35 cycles of reaction at 94° C. for 1 min, at 58° C. for 2 min, and at 72° C. for 1 min, with a final elongation reaction at 72° C. for 7 min using Human Pancreas QUICK-Clone™ cDNA (Clontech Company) as a template, the PCR primers consisting of SEQ ID NO: 19 and SEQ ID NO: 20, and Expand High Fidelity PCR System (Roche Diagnostics K.K.). The amplified PCR product was inserted into pCR2.1 (Invitrogen Corporation) and the sequence was confirmed using the ABI prism DNA sequencing kit (Perkin-Elmer Applied Biosystems, Co.). As a result, the 903 base pair sequence inserted into pCR2.1 was identical to the sequence of positions 1 to 903 of SEQ ID NO: 1 and thus GPR40-pCR2.1 could be obtained.

Example 2

Preparation of a Retrovirus Vector Plasmid

The SV40 promoter-puro(r) region was removed by cleaving pBabe Puro (Morgenstern, J. P. and Land, H. Nucleic Acid Res. 18(12):3587-96, 1990) (SEQ ID NO: 21) with SalI and ClaI, and the terminals were then blunted using Klenow fragment (Takara Shuzo, Co., Ltd.). Into this site, the IRES-hyg(r) region excised from pIREShyg (Clontech Company) by cleavage with NsiI and XbaI and blunted with T4 polymerase (Takara Shuzo, Co., Ltd.) was inserted to obtain pBabeXIH.

This pBabeXIH was cleaved with SspI and BamHI and the 5'-LTR-packaging signal was removed. Into this site, the 5'-LTR-CMV promoter-packaging signal excised from pCLXSN (IMGENEX, Co.) by cleavage with SspI and BamHI was inserted to obtain pBabeCLXIH.

Example 3

Preparation of a Retrovirus Vector Plasmid for Introduction of Gpr40 Gene

The retrovirus expression plasmid obtained in Example 2, pBabeCLXIH, was cleaved with a restriction enzyme, HpaI. Into this site, cDNA encoding GPR40 excised from the GPR40-pCR2.1 obtained in Example 1 by cleavage with EcoRV was inserted to obtain pBabeCL(GPR40)IH (FIG. 1).

Example 4

Preparation of a Retrovirus Vector for Introduction of GPR40 Gene $2 \times 10^6$ 293-EBNA cells (Invitrogen Corporation) were cultured with 10 mL of DMEM medium (Sigma Corporation) (containing 10% fetal bovine serum (FBS), penicillin 100 units/mL, and streptomycin 100 µg/mL) (referred to as "EBNA medium" hereinafter) in a collagen coated dish of a 10 cm diameter (Asahi Technoglass Co., Ltd.). On the following day, 3.3 µg each of pV-gp (prepared by cleaving pVpack-GP (Stratagene, Co.) with NsiI and XbaI to remove IRES-hisD and blunting with T4 polymerase followed by auto-cyclization), pVPack-VSV-G (Stratagene, Co.), and the retrovirus-vector plasmid for introduction of a gene obtained in Example 3 (pBabeCL(GPR40)IH) was transfected to 293-EBNA cells using a lipofection reagent, FuGENE 6 Transfection Reagent (Roche Diagnostics K.K.). Culture media were collected 24 hours after transfection and centrifuged at 1,200×g for 10 min. The supernatant was filtered through a 0.45 µm filter (Millipore Co., Ltd.) to obtain a retrovirus vector for introduction of GPR40 gene.

Example 5

Construction of SE302 Cells Introduced with a Reporter Gene Containing a Cyclic AMP Responsive Element (1) Preparation of a Reporter DNA Containing a Cyclic AMP Responsive Element According to the method by Durocher, Y. et al., (Anal. Biochem., 284(2):316-26, 2000), a unit responsive to cyclic AMP (cAMP) for transcription was constructed as follows. To prepare a unit containing cAMP responsive element (CRE), the oligo DNAs of SEQ ID NO: 22 (5'-cccaagct- tgatatcgaattcgacgtcacagtatgacggcca tgggaattcgacgtcacagtat-gacggccatggggatcccg-3') and of SEQ ID NO: 23 (5'-cgggatc-cccatggccgtcatactgtgacgtcgaattcccatggccgtcatactgtga cgtcgaattcgatatcaagcttggg-3') for CREx2hb, and of SEQ ID NO: 24 (5'-tgcactgcaggaattcccatggccgt-catactgtgacgtcgaattcccatggccgtca to ctgtgacgtcggatcccg-3') and of SEQ ID NO: 25 (5'-cgggatccgacgtcacagtatgacggc-catgggaattcgacgtcacagtatgacgg ccatgggaattcctgcagtgca-3') for CREx2bp were prepared according to a conventional method. Each pair of the oligo DNAs was heat treated at 95° C. and left to form double-stranded DNA molecules (CRE2xhb and CREx2bp) by gradually lowering the temperature to room temperature. CRE2xhb was digested with HindIII and BamHI and CREx2bp was digested with BamHI and PstI, while pBluescriptIISK(+) (Stratagene, Co.) was digested with HindIII and PstI. The digested DNA molecules were purified by electrophoresis to isolate DNA molecules with restriction enzyme sites at both terminals, then these 3 DNA molecules (CRE2xhb, CREx2bp, and pBluescriptSK(+)) were ligated together. The sequence of the plasmid obtained was analyzed and CRE4/pBluescriptIISK(+) was prepared.

Figure 2:
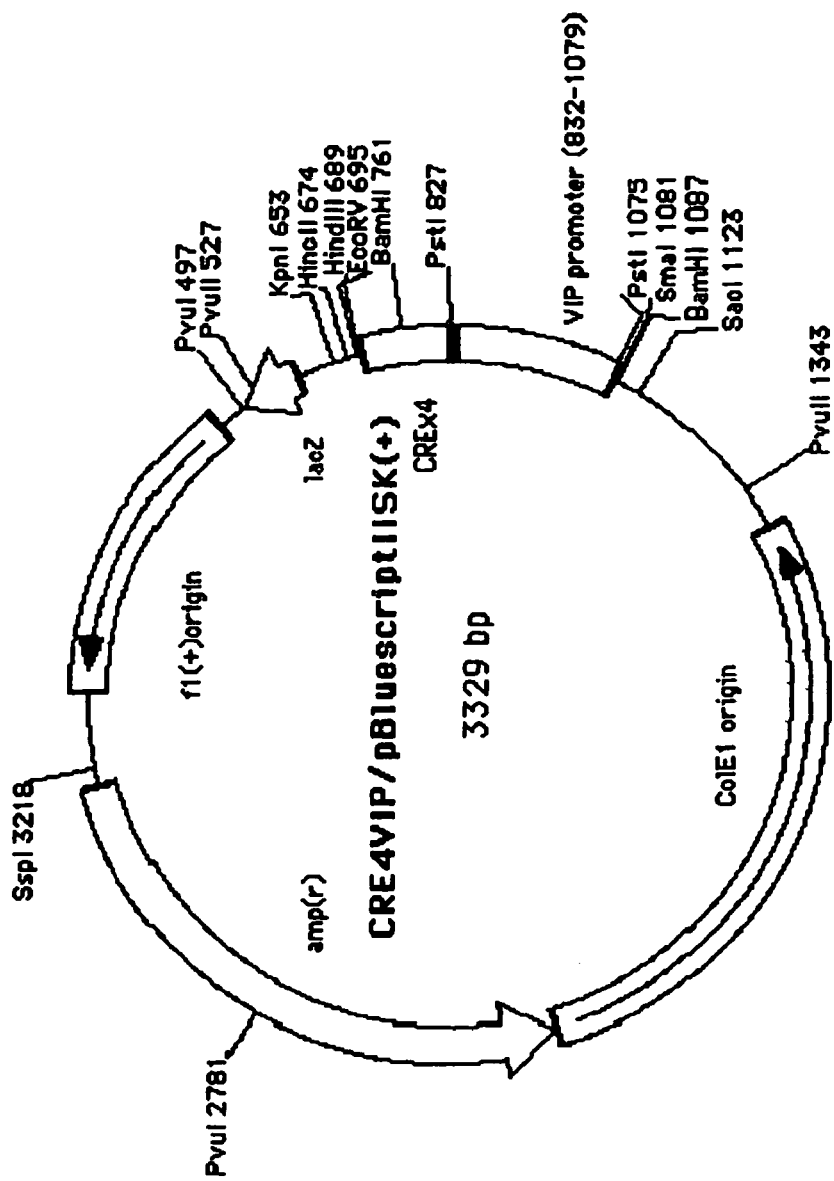
FIG. 2 shows the construction of CRE4VIP/pBluescriptI-ISK (+).

Next, to obtain DNA containing a VIP (vasoactive intestinal peptide) promoter, PCR primers, a 5'-primer (5'-tcgactg-cagcccatggccgtcatactgtg-3') (SEQ ID NO: 26) and a 3'-primer (5'-tgcactgcaggtcggagctgactgttctgg-3') (SEQ ID NO: 27), were prepared according to a conventional method. PCR was carried out by repeating 35 cycles of reaction at 94° C. for 30 sec, at 55° C. for 30 sec, and at 72° C. for 1 min using human genome DNA (Roche Diagnostics K.K.) as a template, and the PCR primer combination of SEQ ID NOs: 26 and 27, and recombinant Taq polymerase (Takara Co.) to obtain a 264 bp (SEQ ID NO: 28) DNA. This 264 bp DNA was digested with PstI and inserted into CRE4/pBluescriptI-ISK(+) at PstI site. The sequence of the plasmid obtained was confirmed and CRE4VIP/pBluescriptIISK(+) was prepared (FIG. 2). This CRE4VIP/pBluescriptIISK(+) was digested with HindIII and SmaI and the terminals of the CRE4VIP promoter fragment obtained were blunted.

Figure 3:
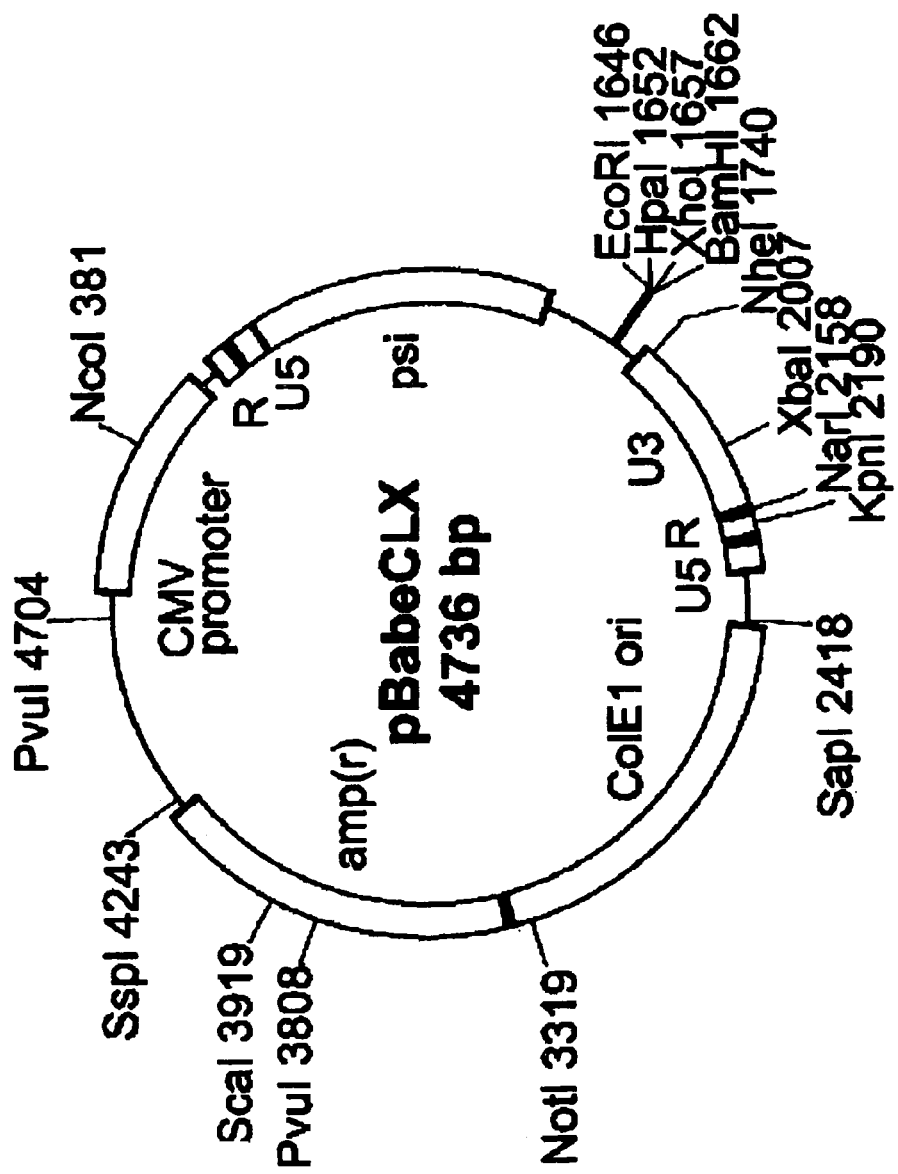
FIG. 3 shows the construction of pBabeCLX.
Figure 4:
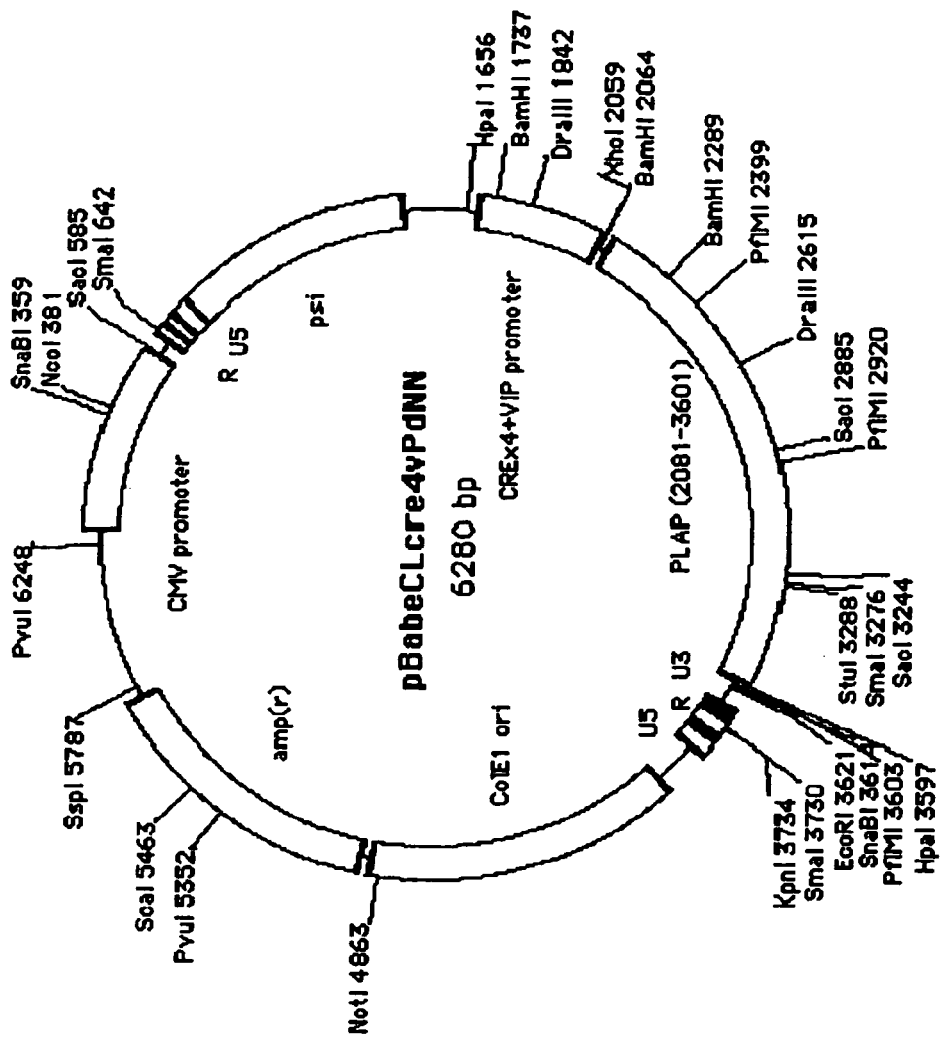
FIG. 4 shows the construction of pBabeCLcre4vPdNN.

The IRES-hyg(r) region was removed from the pBabe-CLXIH obtained in Example 2 to prepare pBabeCLX (FIG. 3). A retrovirus vector plasmid for introduction of an exogenous promoter obtained by removing the NheI-NarI region in the enhancer activity (LTR) originated from retrovirus from PBabeCLX was introduced with the above described blunted CRE4VIP promoter fragment and placental alkaline phosphatase (PLAP)(Goto, M. et al., Mol. Pharmacol. 49(5): 860-73, 1996), a reporter gene, to obtain pBabeCLcre4vPdNN (FIG. 4).

(2) Establishment of SE302 Cells Introduced with a Reporter Gene Containing a Cyclic AMP Responsive Element A retrovirus vector was prepared using a retrovirus vector plasmid pBabeCLcre4vPdNN capable of inducing a reporter gene PLAP by a cyclic AMP responsive element according to the method described in Example 4. The retrovirus vector prepared was introduced into HEK293 cells and the cells were cloned by a limiting dilution method. The clone that showed the best response in PLAP induction (referred to as "SE302" hereinafter) was used for the following experiments.

Example 6

Preparation of GPR40-Introduced SE302 Cells

The SE302 cells constructed in Example 5 were seeded onto a collagen coated 6-well plate (Asahi Technoglass Co., Ltd.) at 1.2×10⁵ cells per well. DMEM medium (Sigma Corporation) (containing 10% FBS, penicillin 100 units/mL, and streptomycin 100 µg/mL) was used as a medium. On the following day, solutions of the virus vector containing GPR40 obtained in Example 4 and polybrene (also called hexadimethrine bromide, Sigma Corporation) at a final concentration of 8 µg/mL were added to SE302 cells. The cells were cultured with the medium containing 350 µg/mL of hygromycin (Invitrogen Corporation) and cells grown under this condition were used for experiments as SE302 cells introduced with GPR40 gene (referred to as "GPR40-SE302 cells" hereinafter).

Example 7

Preparation of GPR43 Gene-Introduced SE302 Cells

In order to isolate a polynucleotide encoding human GPR43 (human GPR43 may be optionally referred simply to as GPR43), PCR primers, a 5'-primer (5'-ttaagcttgccgccac-catgctgccggactggaagagct-3') (SEQ ID NO: 30) and a 3'-primer (5'-ctactctgtagtgaagtccgaa-3') (SEQ ID NO: 31), were designed based on the 993 by nucleic acid sequence of SEQ ID NO: 29, referring to GenBank accession number NM005306 according to an ordinary method. PCR was carried out at 94° C. for 5 min followed by repeating 35 cycles of reaction at 94° C. for 1 min, at 58° C. for 2 min, and at 72° C. for 1 min, with a final elongation reaction at 72° C. for 7 min using Human Lung QUICK-Clone™ cDNA (Clontech Company) as a template, the PCR primers of SEQ ID NO: 30 and SEQ ID NO: 31 in combination, and Expand High Fidelity PCR System (Roche Diagnostics K.K.). The amplified PCR product was inserted into pCR2.1 (Invitrogen Corporation) and the sequence was confirmed using the ABI prism DNA sequencing kit (Perkin-Elmer Applied Biosystems). As a result, the 903 base pair sequence inserted into pCR2.1 was the same as the sequence of positions 1 to 993 of SEQ ID NO: 29 and thus GPR43-pCR2.1 could be obtained.
(2) Preparation of a Retrovirus Vector Plasmid for Introduction of GPR43 Gene The plasmid pBabeCLXIH for expression of a retrovirus obtained in Example 2 was cleaved by a restriction enzyme HpaI. To this, GPR43 excised from the GPR43-pCR2.1 obtained in the above (1) by cleavage with HindIII and BamHI was inserted to obtain pBabeCL (GPR43)IH.
(3) Preparation of GPR43 Gene-Introduced SE302 Cells pBabeCL (GPR43)IH plasmid obtained in (2) above was transfected, together with pV-gp, and pVPack-VSV-G (Stratagene), into 293-EBNA cells (Invitrogen Corporation) in accordance with the method described in Example 4. 24 hours later, culture supernatant was collected, and the obtained retrovirus vector solution for introduction of GPR43 gene was infected with SE302 cells by a method similar to that described in Example 6. The resultant was cultured with medium containing 350 µg/mL hygromycin (Invitrogen Corporation), and the cells grown under this condition were used for experiments as SE302 cells introduced with GPR43 gene (referred to as "GPR43-SE302 cells" hereinafter).

Example 8

Measurement of Transcription Activity in SE302 Cells Introduced with Genes

The GPR40-SE302 cells and GPR43-SE302 cells constructed in Examples 6 and 7 described above were suspended in a culture medium for measurement of transcription activity (DMEM containing FBS, which was heat-treated at 65° C. for 30 min, at a final concentration of 10%) and seeded onto a 96 well plate (Becton Dickinson, Co.) at 1×10⁴ cells/well. In addition, as control cells, SE302 cells expressing green fluorescent protein (GFP, Invitrogen Corporation) (referred to as "GFP-SE302 cells" hereinafter) were used. Specifically, GFP-302 cells were prepared by obtaining a virus for expressing GFP using the method shown in Example 3 and 4, and transfecting SE302 cells with the virus using the method shown in Example 6. Cells were cultured for 24 hours after seeding, and forskolin prepared at a final concentration of 0.3 µM and a sample were added. Cells were cultured for another 24 hours, and 5 µL of the cell supernatant was recovered and transferred to a polypropylene 384-well white plate (Nalge Nunc International, Co.). Then, 20 µL of the assay buffer (280 mmol/L Na₂CO₃—NaHCO₃, 8 mmol/L MgSO₄, pH 10) and 25 µL of Lumiphos530 (Lumigen, Co.) were added. Following a 2-hour reaction at room temperature, chemiluminescence in each well was measured using a Fusion plate reader (Perkin Elmer, Co.) and was defined as the transcription activity. Based on these measured levels, stimulation/inhibition of transcription activity was calculated using the equation (I) shown below and described as [% of control]. Activities of the group with a sample added were calculated using the level of a control placed on each plate.

$$[\% \text{ of control}] = (X-C)/(F-C) \times 100 \tag{I}$$

wherein,

X: PLAP transcription activity in the group added with a sample,

F: Mean level of transcription activity in 2 wells of a positive control (no sample added, stimulated with forskolin), and C: Mean level of transcription activity in 2 wells of a negative control (no sample added, not stimulated with forskolin).

Example 9

Measurement of PLAP Activity in GPR40-SE302 Cells Using a Commercially Available Porcine Pancreatic sPLA2

Figure 5:
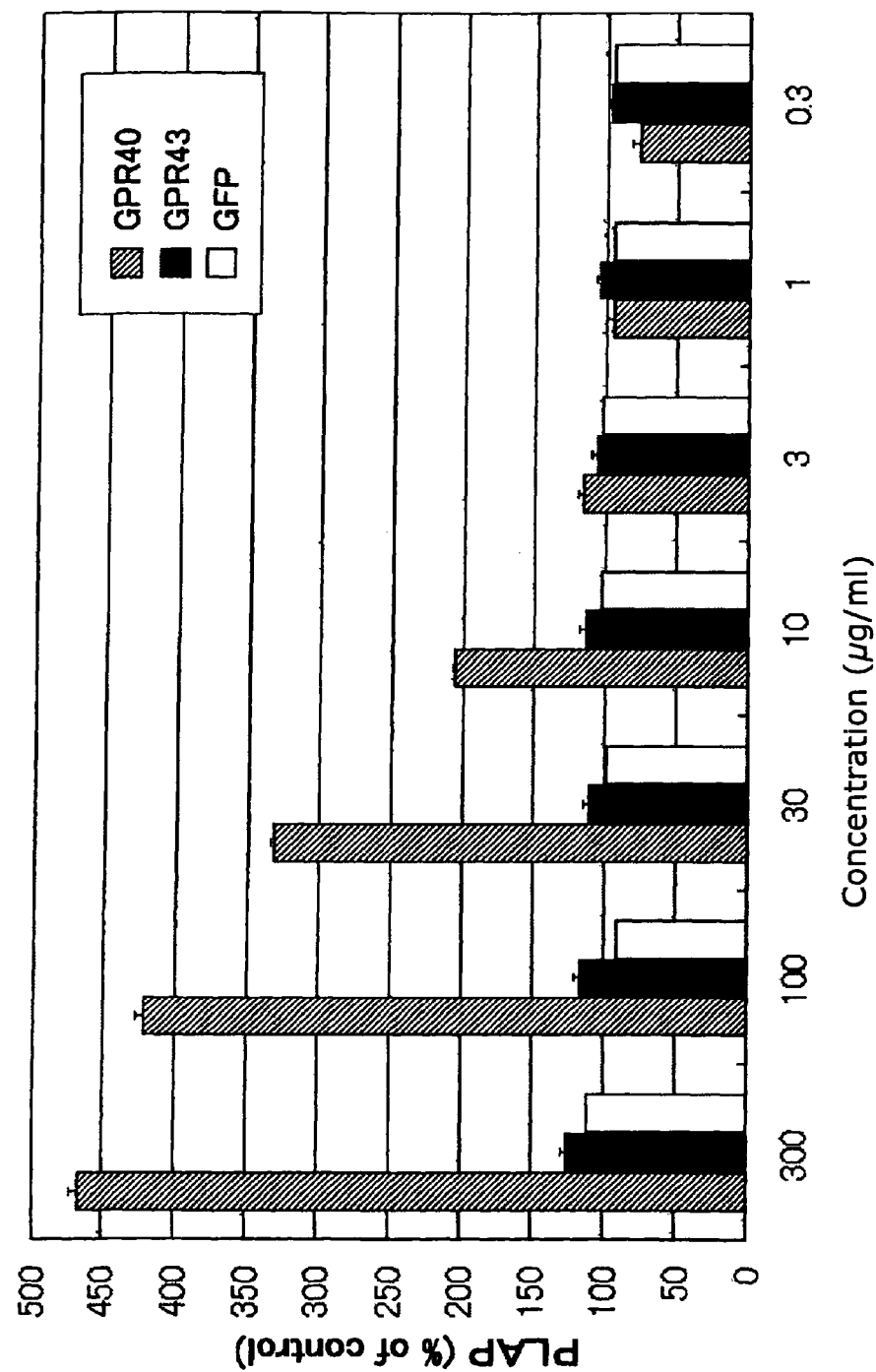
FIG. 5 shows the result of comparison of PLAP activity in GPR40-SE302 cells and those in GPR43-SE302 cells and in GFP-SE302 cells using a commercially available porcine pancreatic sPLA2.

A porcine pancreatic sPLA2 (Phospholipase A2 from porcine pancreas (ammonium sulfate suspension using soybean L-α-phosphatidylcholine) 600 units/mg protein, Sigma Corporation) was centrifuged and the pellet was dissolved in water. PLAP activity was measured according to the method described in Example 8. As shown in FIG. 5, a concentration dependent elevation of PLAP activity in GPR40-SE302 cells was detected, but no elevation of PLAP activity was detected in GPR43-SE302 cells or GFP-SE302 cells. Since this porcine pancreatic sPLA2 is confirmed to be primarily Group IB secretory phospholipase A2 (GIB-sPLA2) (Swiss Prot accession number P00592) (Ta-min Chang et al., 3. Biol. Chem. 274 (16): 10758-10764, 1999), it was shown that GPR40 could be activated by GIB-sPLA2.

Example 10

Cloning of Human and Mouse cDNA Encoding a Precursor Form of GX-sPLA2

Cloning of cDNA encoding a precursor form of human and mouse Group X secretory phospholipase A2 (GX-sPLA2) was carried out by the following method.

(1) Cloning of cDNA Encoding a Precursor Form of Human GX-sPLA2 (hGX-sPLA2)

Isolation of a polynucleotide encoding a precursor form of hGX-sPLA2 was carried out by PCR using Human Lung QUICK-Clone cDNA (Clontech, Co.) as a template, and primers, (a 5'-primer (5'-atggggccgctacctgtgtgcctgcc-3') (SEQ ID NO: 32) and a 3'-primer (5'-tcagtcacacttgggcgagtc-cggc-3') (SEQ ID NO: 33)), designed for the sequence of positions 441 to 938 of the coding region of hGX-sPLA2 based on the nucleic acid sequence of SEQ ID NO: 13 (GenBank accession number NM_003561). The reaction was carried out first at 94° C. for 5 min and followed by repeating 35 cycles of reaction at 94° C. for 1 min, at 61° C. for 1 min, and at 72° C. for 3 min with a final elongation reaction at 72° C. for 7 min using FastStart High Fidelity PCR System (Roche Diagnostics K.K.). The PCR product was inserted into pCR2.1 (Invitrogen Corporation) and the sequence was confirmed. As a result, the 498 base pair sequence inserted was identical to the sequence of positions 441 to 938 of SEQ ID NO: 13 and hGX-sPLA2-pCR2.1 could be obtained.

(2) Cloning of cDNA Encoding Mouse GX-sPLA2 (mGX-sPLA2)

Isolation of the polynucleotide encoding mGX-sPLA2 was carried out by designing 5'-primer (5'-atgctgctgctactgctgctgt-tgc-3') (SEQ ID NO: 34) and a 3'-primer (5'-tcaattgcacttgg-gagagtccttc-3') (SEQ ID NO: 35) for the positions 175 to 630 in the coding region of mGX-sPLA2 based on the nucleic acid sequence of SEQ ID NO: 14 (GenBank accession number NM_011987). A template cDNA was prepared by reverse transcription of the RNA extracted from the large intestine isolated from a C57BL/6NCrj mouse (Charles River Laboratories Japan, Inc.) using an RNeasy Mini kit (QIAGEN), using TaqMan Reverse Transcription Reagents (Applied Biosystems) at 25° C. for 10 min, 48° C. for 60 min, and 95° C. for 10 min. The reaction was carried out first at 94° C. for 5 min and followed by repeating 35 cycles of the reaction at 94° C. for 1 min, at 58° C. for 1 min, and at 72° C. for 3 min, with a final elongation reaction at 72° C. for 7 min, using FastStart High Fidelity PCR System (Roche Diagnostics K.K.). The PCR product was inserted into pCR2.1 (Invitrogen Corporation) and the sequence was confirmed. As a result, the 456 base pair sequence inserted was identical to the sequence of positions 175 to 630 of SEQ ID NO: 14 and thus mGX-sPLA2-pCR2.1 was obtained.

Example 11

Cloning of a Gene for C-terminal His Tagged GX-sPLA2 (GX-sPLA2-His6)

For preparation of a gene for C-terminal His tagged GX-sPLA2 (hGX-sPLA2-His6), PCR was carried out using hGX-sPLA2-pCR2.1 obtained in Example 10 as a template, and a 5'-primer (5'-gatatcgccgccaccatggggccgctacctgtg-3') (SEQ ID NO: 36) and a 3'-primer (5'-gatatctcaatggtgatggtgatgatg-gtcacacttgggcgagtc-3') (SEQ ID NO: 37). Similarly, C-terminal His tagged mouse GX-sPLA2 (mGX-sPLA2-His6) was prepared by PCR using mGX-sPLA2-pCR2.1 obtained in Example 10 as a template, and a 5'-primer (5'-gatatcgccgc-caccatgctgctgctactgctg-3') (SEQ ID NO: 38) and a 3'-primer (5'-gatatctcaatggtgatggtgatga tgattgcacttgggagagtc-3') (SEQ ID NO: 39). PCR was carried out using FastStart High Fidelity PCR System (Roche Diagnostics Co.) first at 94° C. for 5 min followed by repeating 15 cycles at 94° C. for 1 min and at 61° C. for 1 min (for hGX-sPLA2) or at 58° C. for 1 min and at 72° C. for 3 min (for mGX-sPLA2), and finally at 72° C. for 7 min for elongation reaction. The PCR products obtained each was inserted again into pCR2.1 (Invitrogen Corporation) to obtain hGX-sPLA2-His6-pCR2.1 and mGX-sPLA2-His6-pCR2.1.

Example 12

Preparation of Baculovirus for Introduction of a Gene for C-Terminal His-Tagged GX-sPLA2

Baculovirus for introduction of a gene for C-terminal His-tagged GX-sPLA2 was prepared using BAC-TO-BAC Baculovirus Expression Systems (Invitrogen Corporation) according to the manual included in the kit. Specifically, hGX-sPLA2-His6-pCR2.1 and mGX-sPLA2-His6-pCR2.1 obtained in Example 11 were cleaved with restriction enzymes, XbaI and HindIII, and inserted into pFASTBAC1 plasmid previously cleaved with XbaI and HindIII as well to prepare hGX-sPLA2-His6-pFASTBAC and mGX-sPLA2-His6-pFASTBAC, respectively. Bacmid DNA was recovered by transposition of these plasmids in DH10BAC competent cells provided with the kit. Sf9 cells cultured with SF900II SFM (Invitrogen Corporation) were transfected with the bacmid DNA using Cellfectin (Invitrogen Corporation) and the culture supernatant were recovered 3 days later to obtain baculovirus for introduction of a gene for human or mouse C-terminal His-tagged GX-sPLA2.

Example 13

Purification of C-Terminal His-Tagged GX-sPLA2

The baculovirus for introduction of a gene for human or mouse C-terminal His-tagged GX-sPLA2 obtained in Example 12 was infected to Sf9 cells, respectively, and cultured in an Erlenmeyer flask with shaking. The culture media were centrifuged 60 hours later and culture supernatants were obtained. Imidazol (Sigma Corporation) was added to the culture supernatants to make a final concentration of 10 mM and loaded onto a Ni Sepharose 6 Fast Flow column (Amersham Biosciences K.K.). The column was washed with a 5 fold column volume of Binding Buffer (10 mM imidazol, 500 mM NaCl, 20 mM $NaH_2PO_4$, pH 7.4) and eluted with Elution Buffer (500 mM imidazol, 500 mM NaCl, 20 mM $NaH_2PO_4$, 50 mM Tris-HCl, pH 7.4). Eluates were diluted 5 folds with 0.1% TFA and loaded onto a HF MEGA BOND ELUTE C18 column (Varian, Inc.). The column was eluted with 50% acetonitrile containing 0.1% TFA and the eluates were lyophilized to obtain purified human and mouse C-terminal His-tagged GX-sPLA2 (hGX-sPLA2-His and mGX-sPLA2-His, respectively).

Example 14

Measurement of PLAP Activity in GPR40-302 Cells Using C-Terminal His-Tagged mouse GX-sPLA2

Figure 6A:
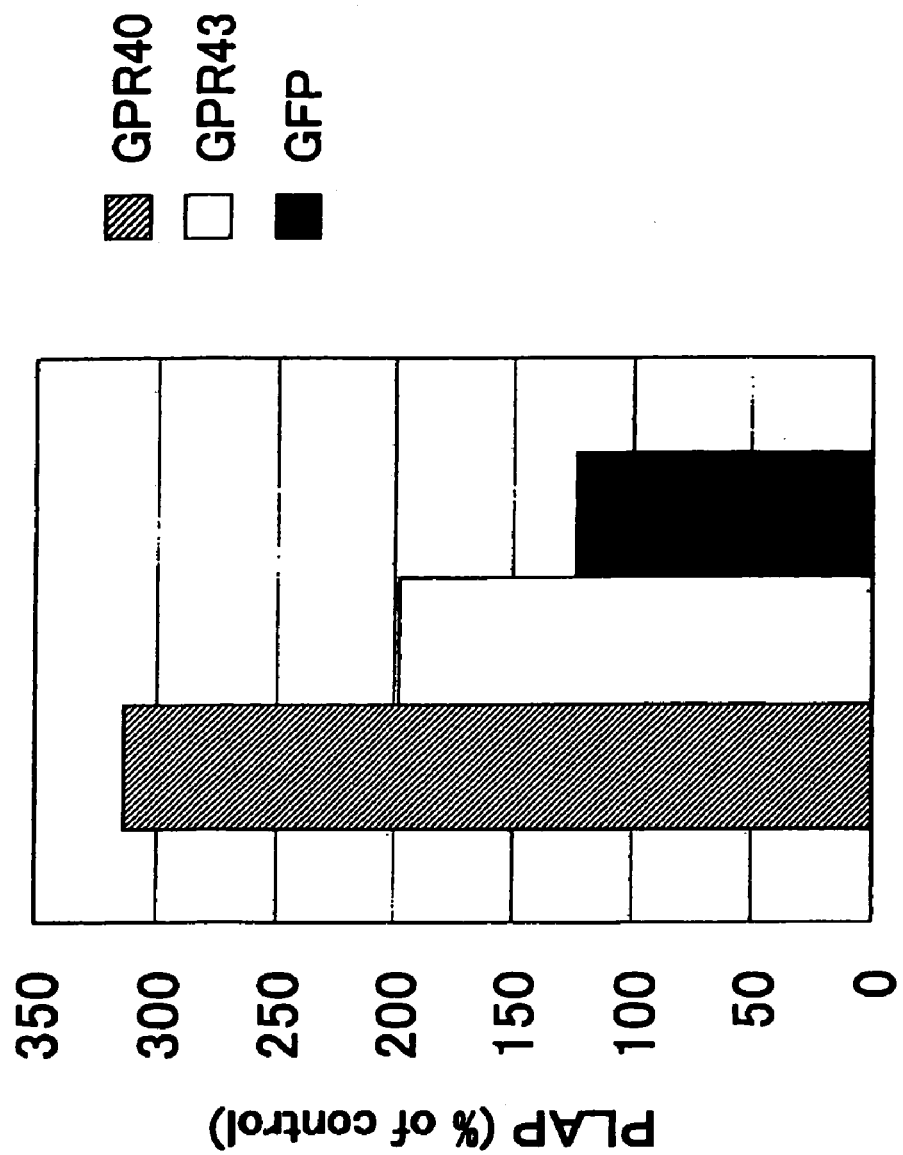
FIG. 6A shows the result of comparison of PLAP activity in GPR40-SE302 cells and those in GPR43-SE302 cells and in GFP-SE302 cells using C-terminal His tagged GX-sPLA2 purified by nickel-column.
Figure 6B:
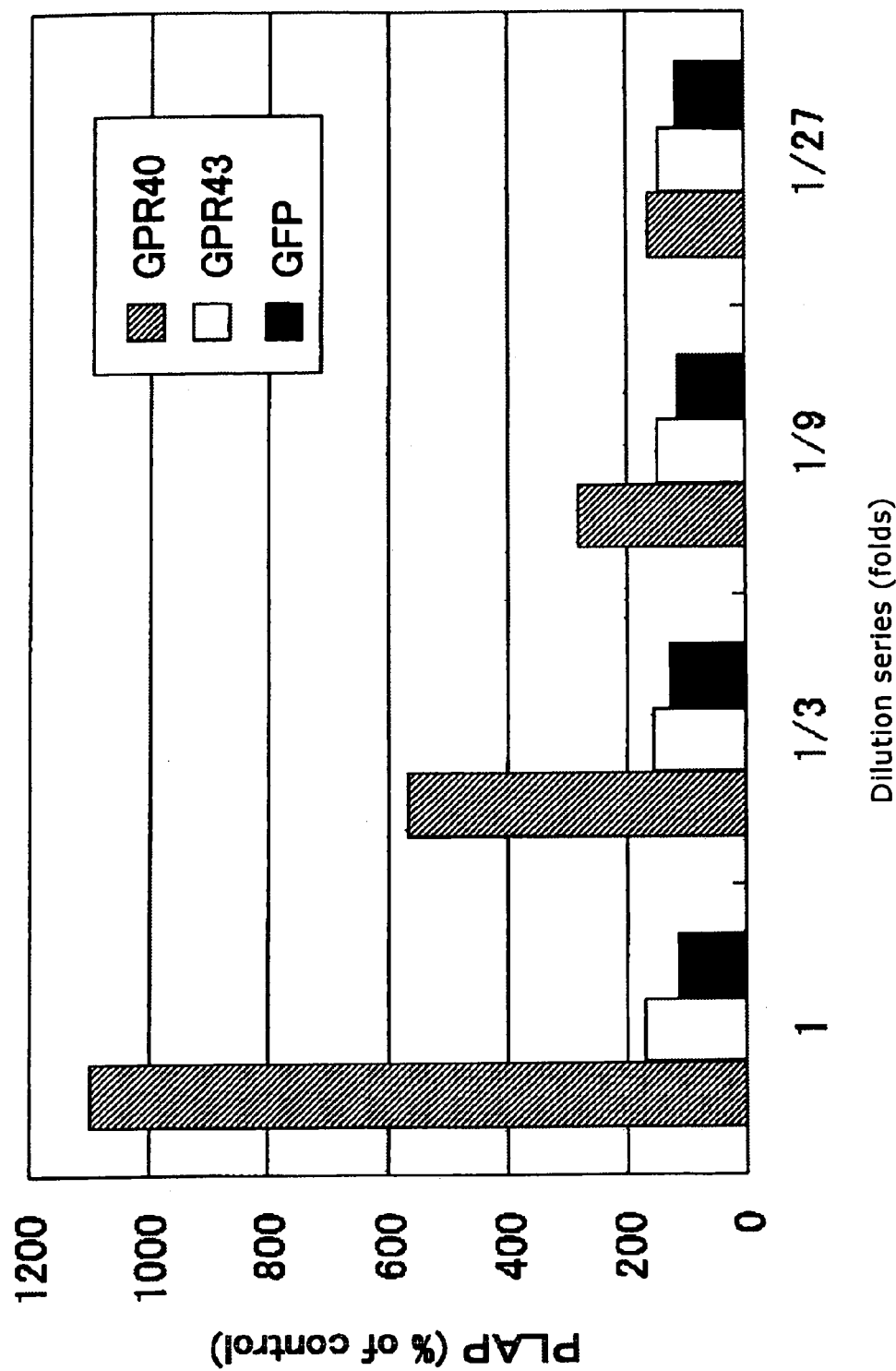
FIG. 6B shows the result of comparison of PLAP activity in GPR40-SE302 cells and those in GPR43-SE302 cells and in GFP-SE302 cells using C-terminal His tagged GX-sPLA2 purified by nickel column.

The lyophilized powders of hGX-sPLA2-His and mGX-sPLA2-His obtained in Example 13 were dissolved in an appropriate amount of 0.1% TFA solution. Using these, PLAP activity in GPR40-SE302 cells was measured according to the method described in Example 8. As shown in FIG. 6, concentration dependent elevations of PLAP activity in GPR40-SE302 cells of hGX-sPLA2-His (FIG. 6-A) and mGX-sPLA2-His (FIG. 6-B) were observed, but no specific elevation of PLAP activity was observed in GFP-SE302 cells.

The result clearly shows that GPR40 was activated by the human and mouse GX-sPLA2.

Example 15

Measurement of PLAP Activity in GPR40-SE302 Cells Using a Commercially Available Honey Bee Venom PLA2

Figure 7:
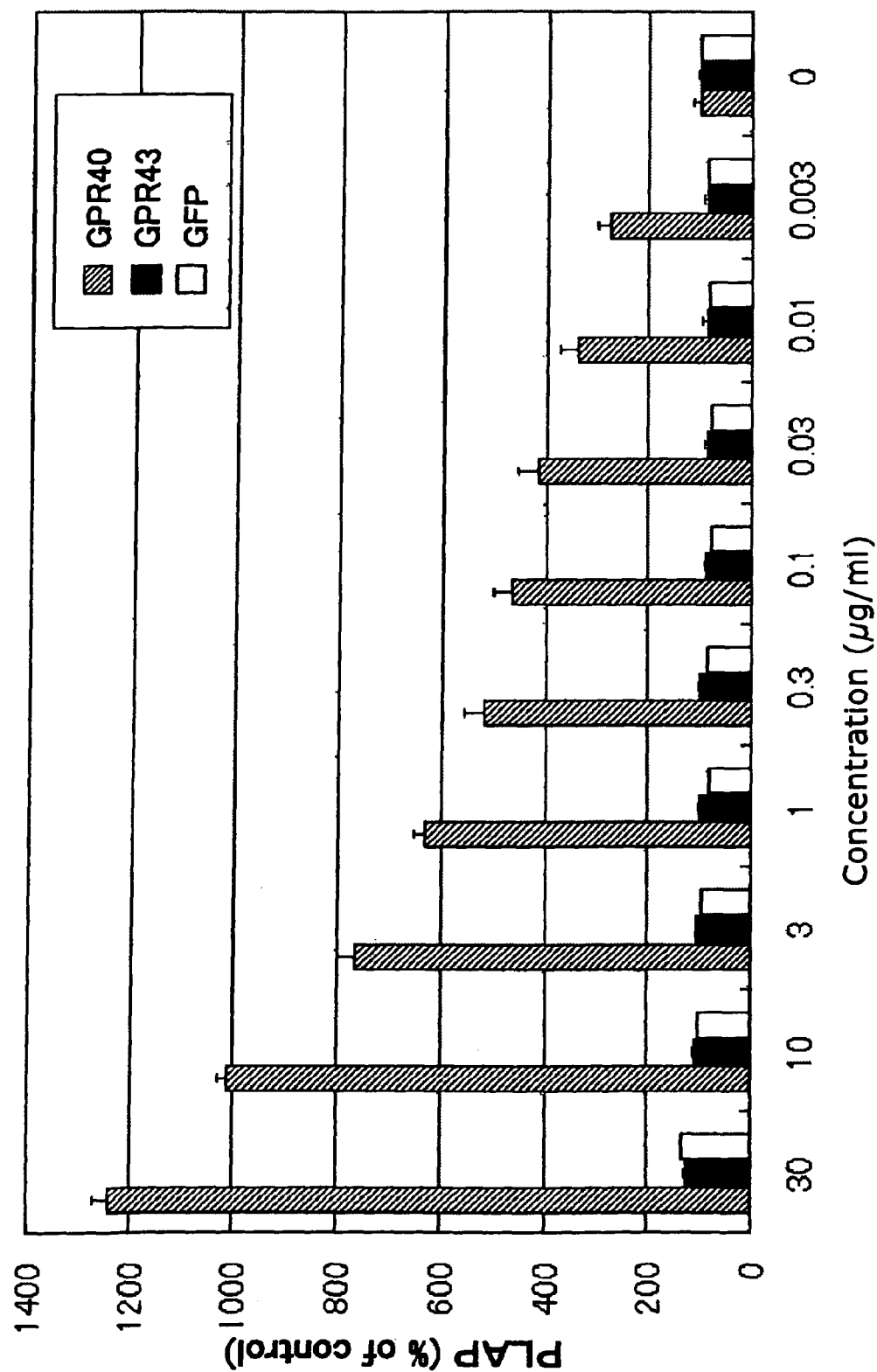
FIG. 7 shows the result of comparison of PLAP activity in GPR40-SE302 cells, in GPR43-SE302 cells and in GFP-SE302 cells using a commercially available honey bee venom PLA2.

A honey bee venom PLA2 (bvPLA2) (Phospholipase A2 from honey bee venom (salt free, lyophilized powder 600 to 1800 units/mg protein, Sigma Corporation) was dissolved in water and PLAP activity was measured in GPR40-SE302 cells according to the method described in Example 8. As shown in FIG. 7, in GPR40-SE302 cells, a concentration dependent elevation of PLAP activity was detected, but no elevation of PLAP activity was detected in GFP-SE302 cells or GPR43-SE302 cells. From these results, it was shown that not only secretary PLA2 such as GIB-sPLA2 and GX-sPLA2 but also honey bee venom derived PLA2 activated GPR40.

Example 16

Measurement of PLAP Activity in GPR40-SE302 Cells Using a Commercially Available Snake Venom PLA2

Figure 8:
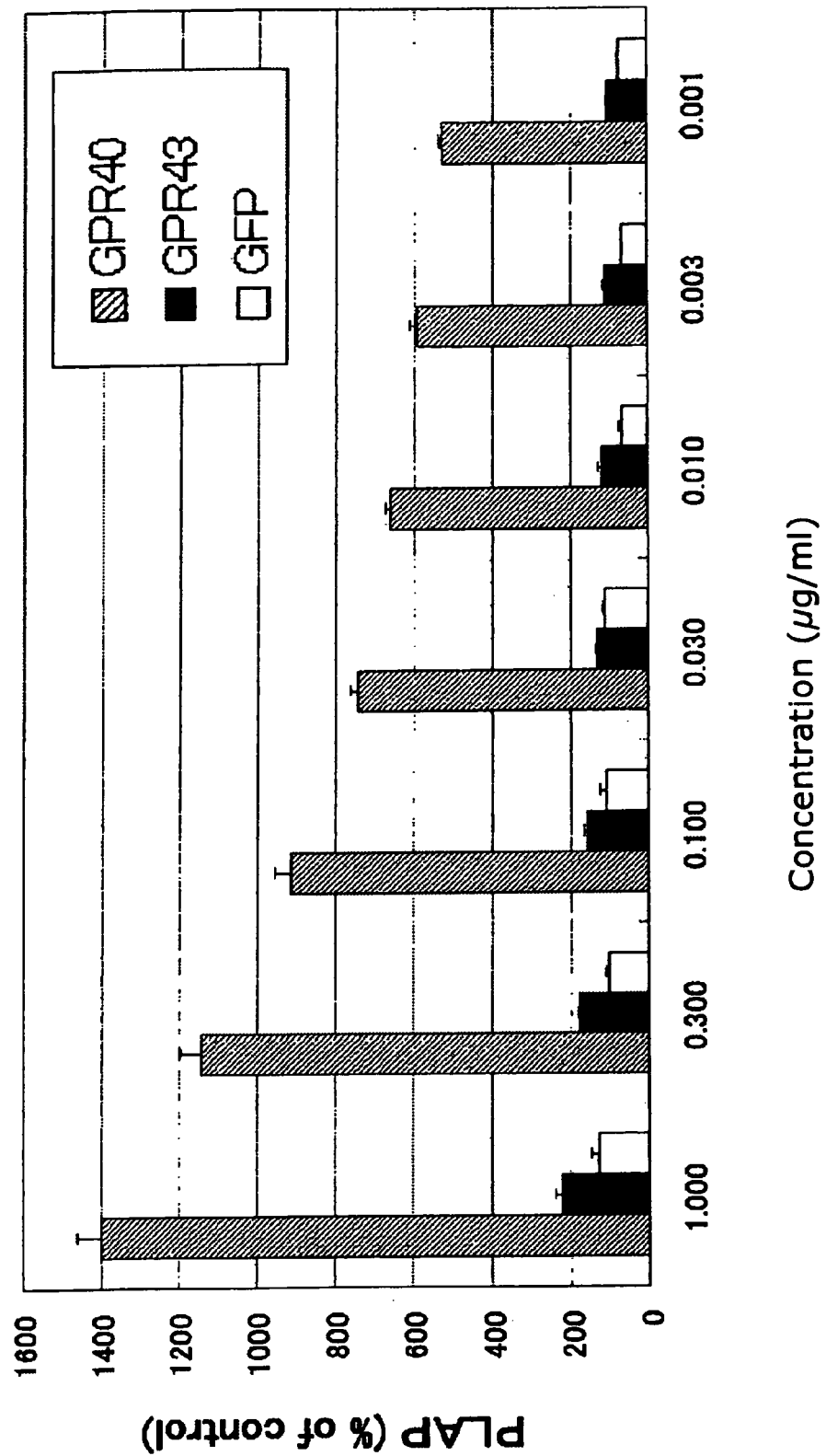
FIG. 8 shows the result of comparison of PLAP activity in GPR40-SE302 cells, in GPR43-SE302 cells and in GFP-SE302 cells using a commercially available honey bee venom PLA2.

A snake venom PLA2 (Phospholipase A2 from Naja mossambica mossambica, lyophilized powder, about 1.500 units/mg protein, pH 8.9, 25° C. using soybean L-α-phosphatidylcholine Sigma Corporation) was dissolved in water and PLAP activity was measured in GPR40-SE302 cells according to the method described in Example 8. As shown in FIG. 8, in GPR40-SE302 cells, a concentration dependent elevation of PLAP activity was detected as compared with GFP-SE302 cells and GPR43-SE302 cells. From these results, it was shown that snake venom derived PLA2 also activated GPR40.

Example 17

Measurement of Changes in Intracellular Calcium Concentration in GPR40-SE302 Cells Using a Commercially Available Honey Bee Venom PLA2

Figure 9:
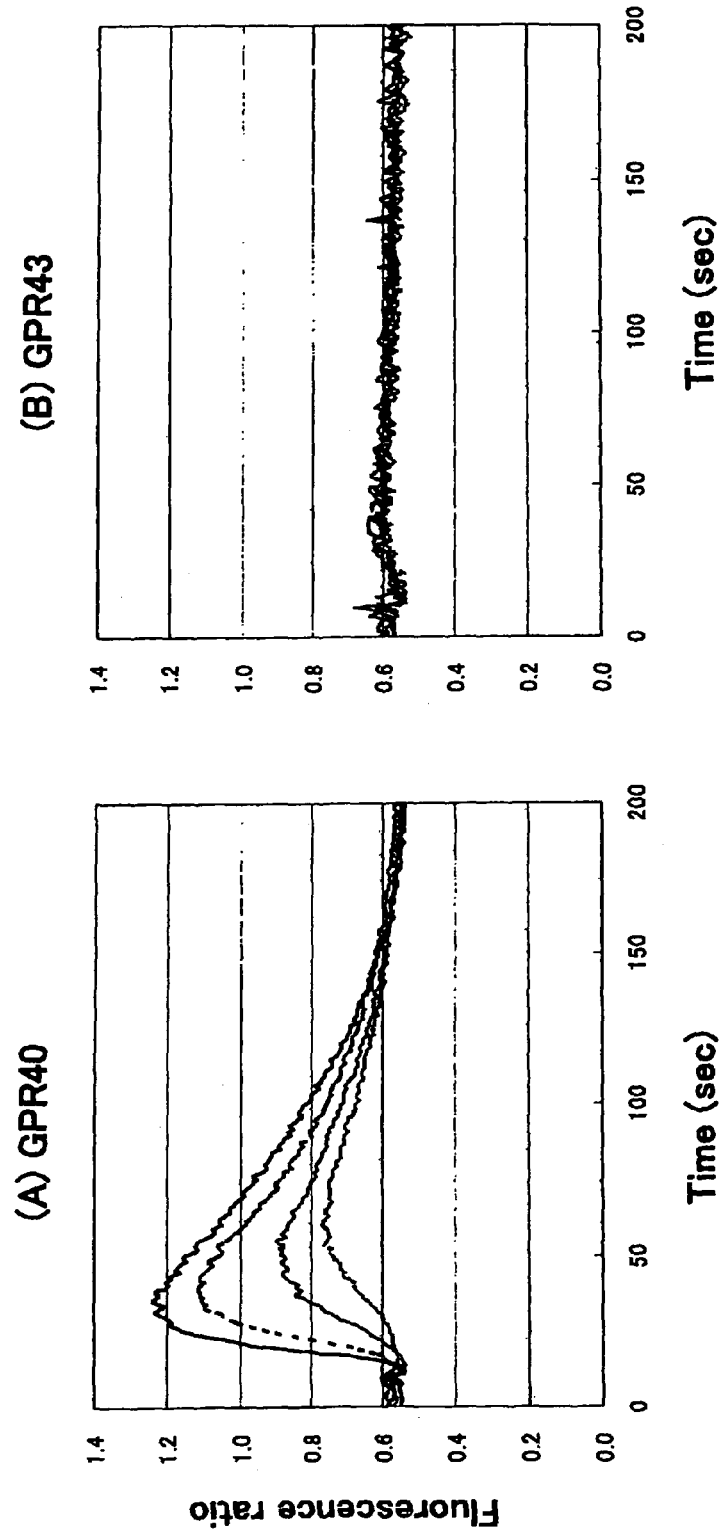
FIG. 9 shows the changes in intracellular calcium concentration in GPR40-SE302 cells (A) and the changes in intracellular calcium concentration in GPR43-SE302 cells (B) following addition of a commercially available honey bee venom PLA2.

20 μl of 1 mM Fura2-AM (Dojin) was diluted with 5 mL of an assay buffer (Hanks liquid added with 10 mM HEPES (pH 7.4), 0.05% glucose, and 2.5 mM probenecid). About $5 \times 10^7$ GPR40-SE302 cells were treated with trypsine, centrifuged, and then suspended in the above-described assay buffer containing Fura-2, and cultured with shaking at room temperature for 2 hours. After that, cells were collected by centrifugation and suspended in the assay buffer to contain $8 \times 10^5$ cells/100 μl, and dispensed in a black walled 96-well plate with half area (Corning Incorporated) at 50 μl/well. The honey bee venom PLA2 (bvPLA2) (Phospholipase $A_2$ from honey bee venom, Sigma) solution used in Example 15 was dispensed in a different 96-well plastic plate (Falcon Co., Ltd.) and the plate was set to FDSS-6000 (Hamamatsu Photonics K.K.). Program was set so that a ligand was added 10 seconds after starting the reading of fluorescence by the FDSS-6000, and the time course of changes in fluorescence were observed. Since changes in fluorescence were observed after adding honey bee venom PLA2 in the cells expressing GPR40 as shown in FIG. 9 (A), it was suggested that the intracellular calcium concentration changed. In addition, the fluorescence of GPR40 concentration-dependently changed by 0.1, 0.3, 1.0, and 3.0 μg/mL of honey bee venom PLA2 (FIG. 9 (A)). On the other hand, even when honey bee venom PLA2 was present in any of the concentrations of 0.1, 0.3, 1.0, and 3.0 μg/mL, no change in fluorescence was observed in the cells expressing GPR43 (FIG. 9 (B)), it was suggested that honey bee venom PLA2 changes the intracellular calcium concentration in a GPR40 specific manner.

Example 18

Cloning of a cDNA Encoding C-Terminal FLAG Tagged GX-sPLA2

C-terminal FLAG-tagged human GX-sPLA2 (hGX-sPLA2-FLAG)(SEQ ID NO: 41) was obtained by PCR using hGX-sPLA2-pCR2.1 obtained in Example 10 as a template, and a 5'-primer of SEQ ID NO: 36 and a 3'-primer (5'-gatatct-cacttgtcatcgtcgtccttgtagtcgtcacacttgggcga-3')(SEQ ID NO: 40). Similarly, C-terminal FLAG-tagged mouse GX-sPLA2 (mGX-sPLA2-FLAG)(SEQ ID NO: 43) was obtained by PCR using mGX-sPLA2-pCR2.1 obtained in Example 10 as a template, and a 5'-primer of SEQ ID NO: 38 and a 3'-primer (5'-gatatctcacttgtcatcgtcgtccttgtagtcattgcacttgggaga-3') (SEQ ID NO: 42). The PCR product obtained was inserted into pCR2.1 (Invitrogen Corporation) again and hGX-sPLA2-FLAG-pCR2.1 and mGX-sPLA2-FLAG-pCR2.1 were obtained, respectively.

Example 19

Measurement of PLAP Activity in GPR40-SE302 Cells Using C-Terminal FLAG-Tagged Recombinant hGX-sPLA2 hGX-sPLA2-FLAG-pCR2.1 obtained Example 18 was digested by the restriction enzyme EcoRV, and the excised fragment was subcloned to the EcoRV site of pYNGvector (Katakura Industries Co., Ltd.). The protein production service (Superworm™ system) (Katakura Industries Co., Ltd.) was assigned to obtain silkworm pupa extract. The silkworm pupa extract was loaded onto ANTI-FLAG™ M2 Agarose (Sigma Corporation) and purified in accordance with the attached manual. sPLA2 enzyme activity was measured using the sPLA2 assay kit (Cayman Chemical Company) in accordance with the attached manual. The active fractions were loaded onto VYDAC™ Protein & Peptide C18 column (#218TP54, VYDAC) and eluted with concentration gradient from 24% to 42% acetonitrile containing 0.1% TFA. A single peak having the highest specific activity among the obtained peaks was used in PLAP assay as a recombinant hGX-sPLA2. Here, the protein concentration of the recombinant was measured using the Dc protein assay (BioRad Laboratories Inc.). The obtained recombinant hGX-sPLA2 was dissolved in 0.1% TFA and PLAP activity in GPR40-SE302 cells was measured in accordance with the method described in Example 8.

Figure 10:
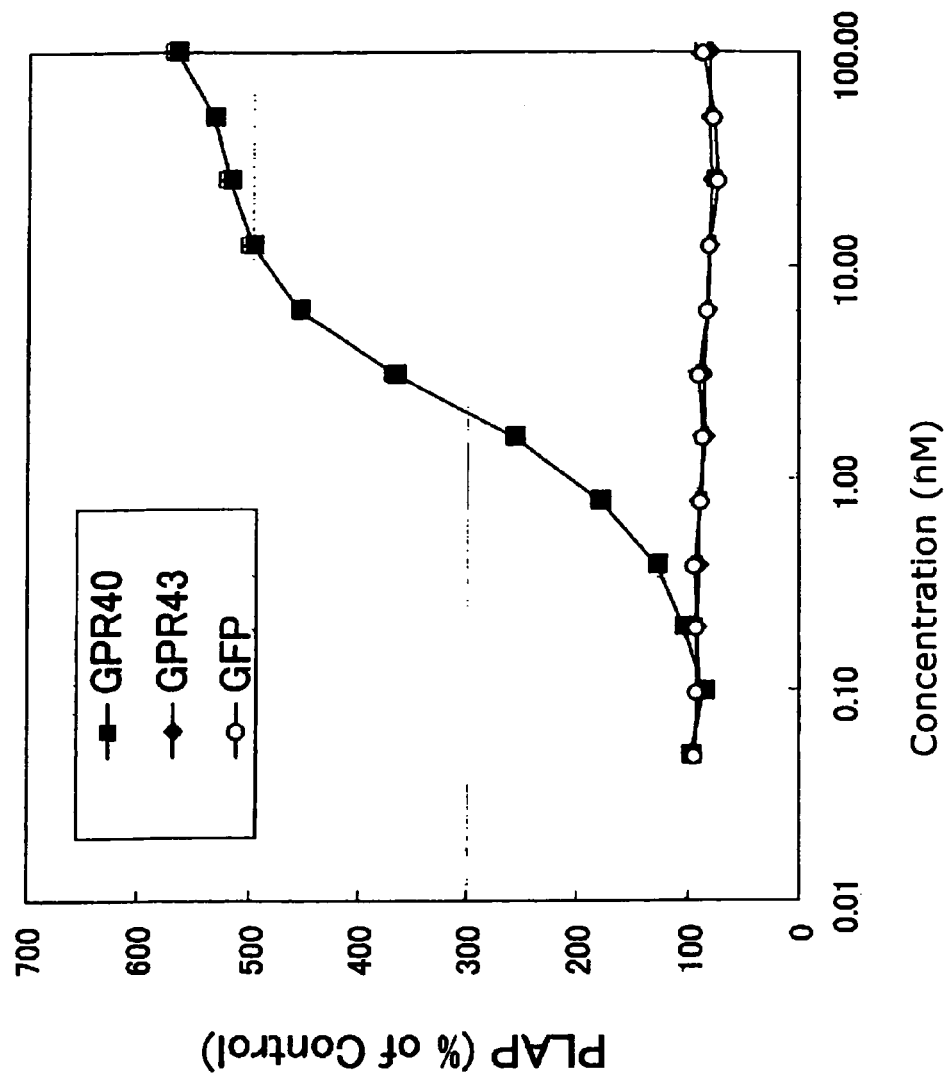
FIG. 10 shows the result of comparison of PLAP activity in GPR40-SE302 cells and those in GPR43-SE302 cells and in GFP-SE302 cells using C-terminal FLAG tagged recombinant hGX-sPLA2.

As shown in FIG. 10, a concentration-dependent elevation of PLAP activity was detected in GPR40-SE302 cells, while no elevation of PLAP activity was detected in GPR43-SE302 or GFP-SE302. The result shows that the C-terminal FLAG tagged hGX-sPLA2 also activates GPR40.

Example 20

Measurement of PLAP Activity in GPR40-SE302 Cells Using C-Terminal FLAG-Tagged Recombinant mGX-sPLA2 mGX-sPLA2-FLAG-pCR2.1 obtained in Example 18 was digested by the restriction enzymes BamHI and XbaI, and the excised fragment was subcloned to the BamHI and XbaI sites of pFastBac (Invitrogen Corporation) to obtain mGX-sPLA2-FLAG-pFAST Bac. The Bac-to-Bac™ baculovirus expression system (Bac-to-Bac Baculovirus Expression System) (Invitrogen Corporation) was used to obtain baculovirus, and then the baculovirus was infected to Sf-9 insect cells. The Sf-9 cells were cultured with Sf-900II (Invitrogen Corporation) (penicillin/streptomycin, 2.5% FCS). The culture supernatant of the Sf-9 cells infected with baculovirus was loaded onto ANTI-FLAGR M2 Agarose (Sigma Corporation) and purified in accordance with the attached manual. sPLA2 enzyme activity was measured using sPLA2 assay kit (Cayman Chemical Company) and in accordance with the attached manual. The active fractions were loaded onto a VYDAC™ Protein & Peptide C18 column (#218TP54, VYDAC) and eluted by a concentration gradient of 24% to 54% acetonitrile containing 0.1% TFA. A single peak having the highest specific activity among the obtained peaks was used as a recombinant hGX-sPLA2 in PLAP assay. Protein concentrations of the recombinant were measured using Dc protein assay (BioRad Laboratories Inc.). The obtained recombinant mGX-sPLA2 was dissolved in 0.05% TFA and 1% BSA (Fatty Acid Free, Sigma Corporation) and PLAP activity in GPR40-SE302 cells was measured in accordance with the method described in Example 8.

Figure 11:
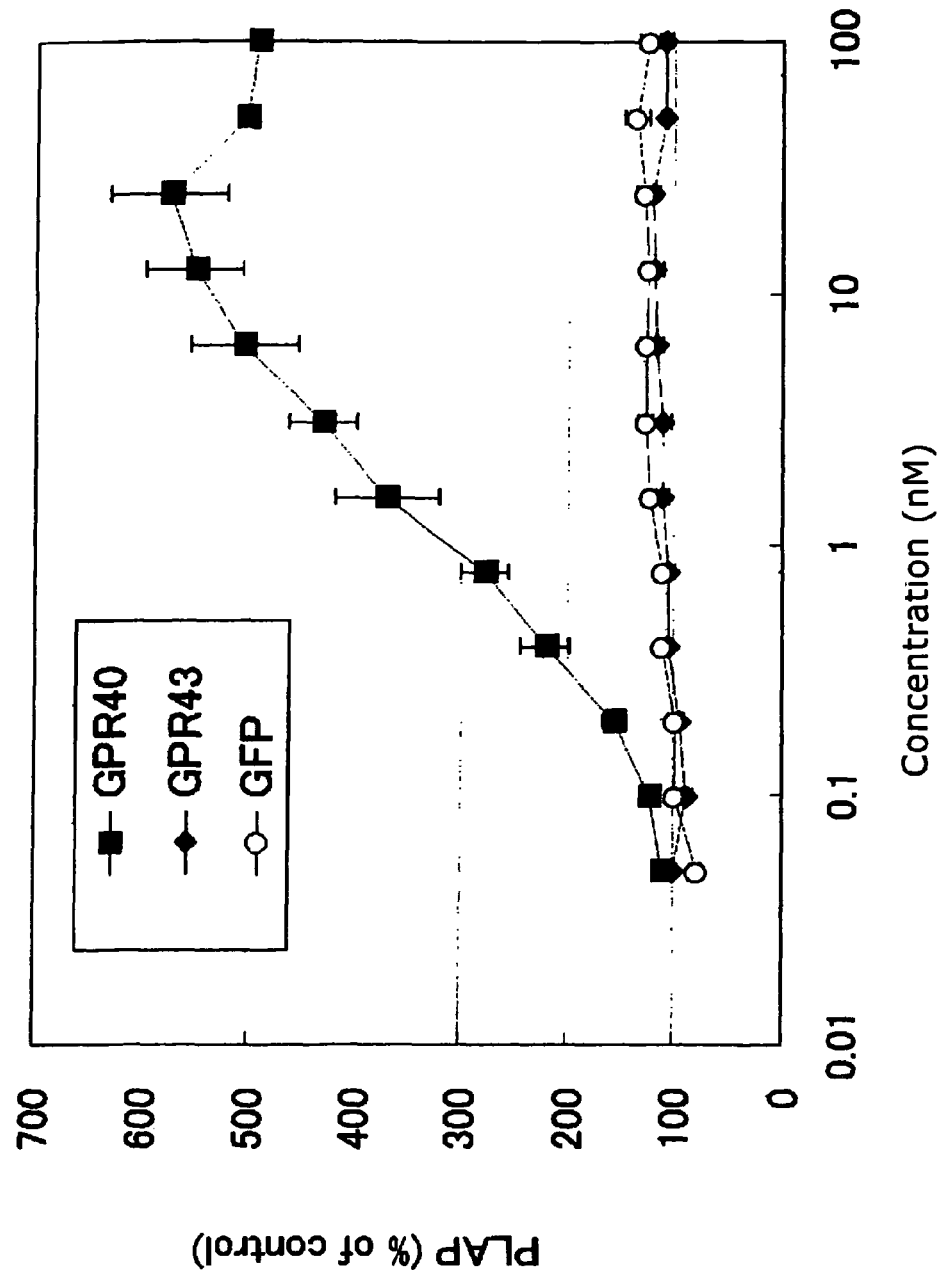
FIG. 11 shows the result of comparison of PLAP activity in GPR40-SE302 cells and those in GPR43-SE302 cells and in GFP-SE302 cells using C-terminal FLAG tagged recombinant mGX-sPLA2.

As shown in FIG. 11, a concentration-dependent elevation of PLAP activity was observed in GPR40-SE302 cells, while no elevation of PLAP activity was observed in GPR43-SE302 or GFP-SE302. The result shows that the C-terminal FLAG tagged mGX-sPLA2 also activates GPR40.

The invention claimed is:

1. A screening method for determining whether a substance of interest is a substance which alters G protein-coupled receptor 40 (GPR40)-mediated cell stimulating activities, comprising the steps of:
contacting cells containing a biomembrane containing GPR40 with secretory phospholipase A2 (sPLA2) or a salt thereof in the presence and absence of the substance of interest, wherein said GPR40 comprises (a) a polypeptide comprising the amino acid sequence of SEQ ID NO: 2; (b) a polypeptide consisting of an amino acid sequence having 95% or higher identity to the amino acid sequence of SEQ ID NO: 2; or (c) a polypeptide encoded by a polynucleotide consisting of a nucleotide sequence having 95% or higher identity to the nucleotide sequence of SEQ ID NO: 1, said GPR40 is activated in response to sPLA2;
measuring cell stimulating activities by using a reporter-assay system that detects a change in an amount of translation/transcription of a reporter gene; and
comparing a result measured in the presence of the substance of interest with a result measured in the absence of the substance of interest, wherein detection of a difference between results measured in the presence and absence of the substance of interest determines that the substance of interest is a candidate substance that alters GPR40-mediated cell stimulating activities.

2. The method according to claim 1, wherein the secretory phospholipase A2 is selected from the group consisting of Group IB secretory phospholipase A2, Group IIA secretory phospholipase A2, Group IIC secretory phospholipase A2, Group IID secretory phospholipase A2, Group IIE secretory phospholipase A2, Group IIF secretory phospholipase A2, Group III secretory phospholipase A2, Group V secretory phospholipase A2, Group X secretory phospholipase A2, Group XIIA secretory phospholipase A2, a honey bee venom phospholipase A2, a snake venom phospholipase A2, and a mixture thereof.

3. The method according to claim 1, wherein the secretory phospholipase A2 is selected from the group consisting of Group IB secretory phospholipase A2, Group X secretory phospholipase A2, a honey bee venom phospholipase A2, a snake venom phospholipase A2, and a mixture thereof.

4. The method according to claim 1, wherein detection of cell stimulating activity that is much elevated in the presence of the substance of interest compared with the absence of the substance of interest indicates identification of a GPR40 agonist.

5. The method according to claim 1, wherein detection of cell stimulating activity that is much suppressed in the presence of the substance of interest compared with the absence of the substance of interest indicates identification of a GPR40 antagonist.

6. The method according to any one of claim 1, 4, or 5, wherein the measurement of the cell stimulating activity is performed by using a reporter-assay system that detects a change in an amount of translation/transcription of a reporter gene by generation of a signaling substance, or by measuring a parameter selected from the group consisting of an intracellular calcium ion release, an activation of adenylate cyclase, an intracellular cAMP production, an intracellular cGMP production, a release of arachidonic acid, a release of acetylcholine, an inositol phosphate production, a change in cell membrane potential, a phosphorylation or activation of intracellular proteins, a pH-changing activity, a phosphorylation or activation of MAP kinase, an activation of c-fos, a glycerol-generating activity, a lipolysis activity, and an insulin-secreting activity.

7. The method of claim 1, wherein said contacting of said cells containing a biomembrane containing GPR40 with sPLA2 or a salt thereof is carried out by addition of said sPLA2 or salt thereof to said cells.

* * * * *

SEQUENCE LISTING

<160> NUMBER OF SEQ ID NOS: 43

<210> SEQ ID NO 1
<211> LENGTH: 903
<212> TYPE: DNA
<213> ORGANISM: Homo sapiens

<400> SEQUENCE: 1

```
atggacctgc ccccgcagct ctccttcggc ctctatgtgg ccgcctttgc gctgggcttc      60
ccgctcaacg tcctggccat ccgaggcgcg acggcccacg cccggctccg tctcaccccct    120 agcctggtct acgccctgaa cctgggctgc tccgacctgc tgctgacagt ctctctgccc     180
ctgaaggcgg tggaggcgct agcctccggg gcctggcctc tgccggcctc gctgtgcccc    240
gtcttcgcgg tggcccactt cttcccactc tatgccggcg ggggcttcct ggccgccctg    300
agtgcaggcc gctacctggg agcagccttc cccttgggct accaagcctt ccggaggccg    360
tgctattcct ggggggtgtg cgcggccatc tgggccctcg tcctgtgtca cctgggtctg    420
gtctttgggt tggaggctcc aggaggctgg ctggaccaca gcaacacctc cctgggcatc    480
aacacaccgg tcaacggctc tccggtctgc ctggaggcct gggacccggc ctctgccggc    540
ccggcccgct cagcctctc tctcctgctc ttttttctgc ccttggccat cacagccttc    600
tgctacgtgg gctgcctccg ggcactggcc cgctccggcc tgacgcacag gcggaagctg    660
cgggccgcct gggtggccgg cggggccctc ctcacgctgc tgctctgcgt aggacccac   720 aacgcctcca acgtggccag cttcctgtac cccaatctag gaggctcctg gcggaagctg    780
gggctcatca cgggtgcctg gagtgtggtg cttaatccgc tggtgaccgg ttacttggga    840
aggggtcctg gcctgaagac agtgtgtgcg gcaagaacgc aaggggggcaa gtcccagaag   900 taa                                                                  903
```

<210> SEQ ID NO 2
<211> LENGTH: 300
<212> TYPE: PRT
<213> ORGANISM: Homo sapiens

<400> SEQUENCE: 2

Met Asp Leu Pro Pro Gln Leu Ser Phe Gly Leu Tyr Val Ala Ala Phe
1               5                   10                  15

Ala Leu Gly Phe Pro Leu Asn Val Leu Ala Ile Arg Gly Ala Thr Ala
            20                  25                  30

His Ala Arg Leu Arg Leu Thr Pro Ser Leu Val Tyr Ala Leu Asn Leu
        35                  40                  45

Gly Cys Ser Asp Leu Leu Leu Thr Val Ser Leu Pro Leu Lys Ala Val
    50                  55                  60

Glu Ala Leu Ala Ser Gly Ala Trp Pro Leu Pro Ala Ser Leu Cys Pro
65                  70                  75                  80

Val Phe Ala Val Ala His Phe Phe Pro Leu Tyr Ala Gly Gly Gly Phe
                85                  90                  95

Leu Ala Ala Leu Ser Ala Gly Arg Tyr Leu Gly Ala Phe Pro Leu
            100                 105                 110

Gly Tyr Gln Ala Phe Arg Arg Pro Cys Tyr Ser Trp Gly Val Cys Ala
            115                 120                 125

Ala Ile Trp Ala Leu Val Leu Cys His Leu Gly Leu Val Phe Gly Leu
        130                 135                 140

Glu Ala Pro Gly Gly Trp Leu Asp His Ser Asn Thr Ser Leu Gly Ile
145                 150                 155                 160

Asn Thr Pro Val Asn Gly Ser Pro Val Cys Leu Glu Ala Trp Asp Pro
                165                 170                 175

Ala Ser Ala Gly Pro Ala Arg Phe Ser Leu Ser Leu Leu Phe Phe
            180                 185                 190

Leu Pro Leu Ala Ile Thr Ala Phe Cys Tyr Val Gly Cys Leu Arg Ala
            195                 200                 205

Leu Ala Arg Ser Gly Leu Thr His Arg Arg Lys Leu Arg Ala Ala Trp
        210                 215                 220

Val Ala Gly Gly Ala Leu Leu Thr Leu Leu Cys Val Gly Pro Tyr
225                 230                 235                 240

Asn Ala Ser Asn Val Ala Ser Phe Leu Tyr Pro Asn Leu Gly Ser
                245                 250                 255

Trp Arg Lys Leu Gly Leu Ile Thr Gly Ala Trp Ser Val Leu Asn
            260                 265                 270

Pro Leu Val Thr Gly Tyr Leu Gly Arg Gly Pro Gly Leu Lys Thr Val
            275                 280                 285

Cys Ala Ala Arg Thr Gln Gly Gly Lys Ser Gln Lys
        290                 295                 300

<210> SEQ ID NO 3
<211> LENGTH: 903
<212> TYPE: DNA
<213> ORGANISM: Mus musculus

<400> SEQUENCE: 3
atggacctgc ccccacagtt ctccttcgct ctctatgtat ctgcctttgc gctgggcttt      60
ccattgaact tgttagccat ccgaggcgca gtgtcccacg ctaaactgcg actcactccc     120
agcttggtct acactctcca tctgggctgc tctgatctcc tactggccat cactctgccc     180
ctgaaggctg tggaggccct ggcttctgga gcctggcccc tgccgctccc cttctgccca     240
gtctttgcct ggcccacttt gctcccctc tacgcaggcg aggcttcct agctgctctc      300 agcgctggcc gctacctggg gctgccttc cccttcgggt accaagccat ccggaggccc      360
cgctattcct ggggtgtgtg tgtggctata tgggcccttg tcctctgcca ctggggctg      420 gcccttggct tggagacttc cggaagctgc tggacaaca gtaccagttc cctgggcatc      480 aacataccg tgaatggctc cccggtctgc ctggaagcct gggatccga ctctgcccgc      540 cctgcccgtc tcagtttctc cattctgctc ttctttctgc ccttggtcat cactgccttc      600
tgctatgtgg gctgcctccg ggccctggtg cgctcaggcc tgagccacaa acggaagctc      660
agggcagctt gggtggccgg aggcgctctc ctcacactcc tgctctgcct ggggccctat      720

```
aatgcctcca atgtggctag tttcataaac ccggacctag gaggctcctg gaggaagttg    780
ggactcatca caggggcctg gagtgtggta ctcaacccac tggtcactgg ctacttggga    840
acaggtcctg gacggggaac aatatgtgtg acgaggactc aaagaggaac aattcagaag    900
tag                                                                  903
```

```
<210> SEQ ID NO 4
<211> LENGTH: 300
<212> TYPE: PRT
<213> ORGANISM: Mus musculus

<400> SEQUENCE: 4
```

```
Met Asp Leu Pro Pro Gln Phe Ser Phe Ala Leu Tyr Val Ser Ala Phe
1               5                   10                  15

Ala Leu Gly Phe Pro Leu Asn Leu Leu Ala Ile Arg Gly Ala Val Ser
            20                  25                  30

His Ala Lys Leu Arg Leu Thr Pro Ser Leu Val Tyr Thr Leu His Leu
        35                  40                  45

Gly Cys Ser Asp Leu Leu Leu Ala Ile Thr Leu Pro Leu Lys Ala Val
    50                  55                  60

Glu Ala Leu Ala Ser Gly Ala Trp Pro Leu Pro Leu Pro Phe Cys Pro
65                  70                  75                  80

Val Phe Ala Leu Ala His Phe Ala Pro Leu Tyr Ala Gly Gly Gly Phe
                85                  90                  95

Leu Ala Ala Leu Ser Ala Gly Arg Tyr Leu Gly Ala Ala Phe Pro Phe
            100                 105                 110

Gly Tyr Gln Ala Ile Arg Arg Pro Arg Tyr Ser Trp Gly Val Cys Val
        115                 120                 125

Ala Ile Trp Ala Leu Val Leu Cys His Leu Gly Leu Ala Leu Gly Leu
    130                 135                 140

Glu Thr Ser Gly Ser Trp Leu Asp Asn Ser Thr Ser Ser Leu Gly Ile
145                 150                 155                 160

Asn Ile Pro Val Asn Gly Ser Pro Val Cys Leu Glu Ala Trp Asp Pro
                165                 170                 175

Asp Ser Ala Arg Pro Ala Arg Leu Ser Phe Ser Ile Leu Leu Phe Phe
            180                 185                 190

Leu Pro Leu Val Ile Thr Ala Phe Cys Tyr Val Gly Cys Leu Arg Ala
        195                 200                 205

Leu Val Arg Ser Gly Leu Ser His Lys Arg Lys Leu Arg Ala Ala Trp
    210                 215                 220

Val Ala Gly Gly Ala Leu Leu Thr Leu Leu Leu Cys Leu Gly Pro Tyr
225                 230                 235                 240

Asn Ala Ser Asn Val Ala Ser Phe Ile Asn Pro Asp Leu Gly Gly Ser
                245                 250                 255

Trp Arg Lys Leu Gly Leu Ile Thr Gly Ala Trp Ser Val Val Leu Asn
            260                 265                 270

Pro Leu Val Thr Gly Tyr Leu Gly Thr Gly Pro Gly Arg Gly Thr Ile
        275                 280                 285

Cys Val Thr Arg Thr Gln Arg Gly Thr Ile Gln Lys
    290                 295                 300
```

```
<210> SEQ ID NO 5
<211> LENGTH: 903
<212> TYPE: DNA
<213> ORGANISM: Rattus norvegicus
```

<400> SEQUENCE: 5

```
atggacctgc ccccacagct ctccttcgct ctctatgtat cagcctttgc actaggcttt      60
ccattgaact tgttagccat ccgaggtgca gtgtcccacg cgaaactgcg actcaccccc     120
agcttggtct acactctcca tttggcctgc tctgacctcc tactggccat caccctgccc     180
ctgaaggctg tggaggccct ggcttctggg gtctggcccc tgccactccc cttctgccca     240
gtctttgcct tggcccactt tgcgcccctc tatgcaggtg aggcttcct ggctgctctc      300
agtgctggcc gctacctggg agctgccttc cccttggat accaagccat ccggaggccc      360
tgctattcct ggggtgtgtg tgtggctata tgggcccttg tcctttgcca cctgggactg     420
gctcttggct tggaggctcc cagaggctgg gtggataaca ccaccagttc cctgggcatc     480
aacatacccg tgaatggctc cccggtctgc ctggaagcgt gggatcctga ctctgcccgc     540
cctgcccgac tcagtttctc gattctgctc ttctttctgc ccttggttat cactgctttc     600
tgctatgtgg gctgcctccg ggccctggtg cactcgggcc tgagccacaa acggaagctc     660
agggcagctt gggtggctgg aggagcactt ctcacactcc tgctctgcct ggggccctat     720
aatgcttcca atgtgctag tttcataaac ccggacttag aaggctcctg aggaagttg      780
gggctcatca caggagcctg gagtgtggtg ctcaacccac tggtcactgg ctacttggga     840
acaggtcctg gacaggggac aatatgtgtg accaggactc caagagggac aattcagaag     900
tag                                                                    903
```

<210> SEQ ID NO 6
<211> LENGTH: 300
<212> TYPE: PRT
<213> ORGANISM: Rattus norvegicus

<400> SEQUENCE: 6

```
Met Asp Leu Pro Pro Gln Leu Ser Phe Ala Leu Tyr Val Ser Ala Phe
1               5                   10                  15

Ala Leu Gly Phe Pro Leu Asn Leu Leu Ala Ile Arg Gly Ala Val Ser
            20                  25                  30

His Ala Lys Leu Arg Leu Thr Pro Ser Leu Val Tyr Thr Leu His Leu
        35                  40                  45

Ala Cys Ser Asp Leu Leu Leu Ala Ile Thr Leu Pro Leu Lys Ala Val
    50                  55                  60

Glu Ala Leu Ala Ser Gly Val Trp Pro Leu Pro Leu Pro Phe Cys Pro
65                  70                  75                  80

Val Phe Ala Leu Ala His Phe Ala Pro Leu Tyr Ala Gly Gly Gly Phe
                85                  90                  95

Leu Ala Ala Leu Ser Ala Gly Arg Tyr Leu Gly Ala Ala Phe Pro Phe
            100                 105                 110

Gly Tyr Gln Ala Ile Arg Arg Pro Cys Tyr Ser Trp Gly Val Cys Val
        115                 120                 125

Ala Ile Trp Ala Leu Val Leu Cys His Leu Gly Leu Ala Leu Gly Leu
    130                 135                 140

Glu Ala Pro Arg Gly Trp Val Asp Asn Thr Thr Ser Ser Leu Gly Ile
145                 150                 155                 160

Asn Ile Pro Val Asn Gly Ser Pro Val Cys Leu Glu Ala Trp Asp Pro
                165                 170                 175

Asp Ser Ala Arg Pro Ala Arg Leu Ser Phe Ser Ile Leu Leu Phe Phe
            180                 185                 190

Leu Pro Leu Val Ile Thr Ala Phe Cys Tyr Val Gly Cys Leu Arg Ala
        195                 200                 205
```

```
Leu Val His Ser Gly Leu Ser His Lys Arg Lys Leu Arg Ala Ala Trp
    210                 215                 220
Val Ala Gly Gly Ala Leu Leu Thr Leu Leu Leu Cys Leu Gly Pro Tyr
225                 230                 235                 240
Asn Ala Ser Asn Val Ala Ser Phe Ile Asn Pro Asp Leu Glu Gly Ser
                245                 250                 255
Trp Arg Lys Leu Gly Leu Ile Thr Gly Ala Trp Ser Val Val Leu Asn
        260                 265                 270
Pro Leu Val Thr Gly Tyr Leu Gly Thr Gly Pro Gly Gln Gly Thr Ile
            275                 280                 285
Cys Val Thr Arg Thr Pro Arg Gly Thr Ile Gln Lys
    290                 295                 300
```

<210> SEQ ID NO 7
<211> LENGTH: 123
<212> TYPE: PRT
<213> ORGANISM: Homo sapiens

<400> SEQUENCE: 7

```
Gly Ile Leu Glu Leu Ala Gly Thr Val Gly Cys Val Gly Pro Arg Thr
1               5                   10                  15
Pro Ile Ala Tyr Met Lys Tyr Gly Cys Phe Cys Gly Leu Gly Gly His
            20                  25                  30
Gly Gln Pro Arg Asp Ala Ile Asp Trp Cys Cys His Gly His Asp Cys
        35                  40                  45
Cys Tyr Thr Arg Ala Glu Glu Ala Gly Cys Ser Pro Lys Thr Glu Arg
    50                  55                  60
Tyr Ser Trp Gln Cys Val Asn Gln Ser Val Leu Cys Gly Pro Ala Glu
65                  70                  75                  80
Asn Lys Cys Gln Glu Leu Leu Cys Lys Cys Asp Gln Glu Ile Ala Asn
                85                  90                  95
Cys Leu Ala Gln Thr Glu Tyr Asn Leu Lys Tyr Leu Phe Tyr Pro Gln
            100                 105                 110
Phe Leu Cys Glu Pro Asp Ser Pro Lys Cys Asp
        115                 120
```

<210> SEQ ID NO 8
<211> LENGTH: 123
<212> TYPE: PRT
<213> ORGANISM: Mus musculus

<400> SEQUENCE: 8

```
Gly Leu Leu Glu Leu Ala Gly Thr Leu Asp Cys Val Gly Pro Arg Ser
1               5                   10                  15
Pro Met Ala Tyr Met Asn Tyr Gly Cys Tyr Cys Gly Leu Gly Gly His
            20                  25                  30
Gly Glu Pro Arg Asp Ala Ile Asp Trp Cys Cys Tyr His His Asp Cys
        35                  40                  45
Cys Tyr Ser Arg Ala Gln Asp Ala Gly Cys Ser Pro Lys Leu Asp Arg
    50                  55                  60
Tyr Pro Trp Lys Cys Met Asp His His Ile Leu Cys Gly Pro Ala Glu
65                  70                  75                  80
Asn Lys Cys Gln Glu Leu Leu Cys Arg Cys Asp Glu Glu Leu Ala Tyr
                85                  90                  95
Cys Leu Ala Gly Thr Glu Tyr His Leu Lys Tyr Leu Phe Phe Pro Ser
            100                 105                 110
```

```
Ile Leu Cys Glu Lys Asp Ser Pro Lys Cys Asn
        115                 120
```

<210> SEQ ID NO 9
<211> LENGTH: 123
<212> TYPE: PRT
<213> ORGANISM: Rattus norvegicus

<400> SEQUENCE: 9

```
Gly Leu Leu Glu Leu Ala Gly Thr Leu Asp Cys Val Gly Pro Arg Ser
1               5                   10                  15

Pro Met Ala Tyr Met Asn Tyr Gly Cys Tyr Cys Gly Leu Gly Gly His
            20                  25                  30

Gly Glu Pro Arg Asp Ala Ile Asp Trp Cys Cys Tyr Tyr His Asp Cys
        35                  40                  45

Cys Tyr Ser Gln Ala Gln Asp Ala Gly Cys Ser Pro Lys Leu Tyr Arg
    50                  55                  60

Tyr Pro Trp Lys Cys Met Asp His Arg Ile Leu Cys Gly Pro Ala Glu
65                  70                  75                  80

Asn Lys Cys Gln Glu Leu Leu Cys Arg Cys Asp Glu Thr Leu Ala Tyr
                85                  90                  95

Cys Leu Ala Asp Thr Glu Tyr His Leu Lys Tyr Leu Phe Phe Pro Ser
            100                 105                 110

Val Leu Cys Glu Lys Asp Ser Pro Lys Cys Asn
        115                 120
```

<210> SEQ ID NO 10
<211> LENGTH: 124
<212> TYPE: PRT
<213> ORGANISM: Sus scrofa

<400> SEQUENCE: 10

```
Ala Leu Trp Gln Phe Arg Ser Met Ile Lys Cys Ala Ile Pro Gly Ser
1               5                   10                  15

His Pro Leu Met Asp Phe Asn Asn Tyr Gly Cys Tyr Cys Gly Leu Gly
            20                  25                  30

Gly Ser Gly Thr Pro Val Asp Glu Leu Asp Arg Cys Cys Glu Thr His
        35                  40                  45

Asp Asn Cys Tyr Arg Asp Ala Lys Asn Leu Asp Ser Cys Lys Phe Leu
    50                  55                  60

Val Asp Asn Pro Tyr Thr Glu Ser Tyr Ser Tyr Ser Cys Ser Asn Thr
65                  70                  75                  80

Glu Ile Thr Cys Asn Ser Lys Asn Asn Ala Cys Glu Ala Phe Ile Cys
                85                  90                  95

Asn Cys Asp Arg Asn Ala Ala Ile Cys Phe Ser Lys Ala Pro Tyr Asn
            100                 105                 110

Lys Glu His Lys Asn Leu Asp Thr Lys Lys Tyr Cys
        115                 120
```

<210> SEQ ID NO 11
<211> LENGTH: 134
<212> TYPE: PRT
<213> ORGANISM: Apis mellifera

<400> SEQUENCE: 11

```
Ile Ile Tyr Pro Gly Thr Leu Trp Cys Gly His Gly Asn Lys Ser Ser
1               5                   10                  15

Gly Pro Asn Glu Leu Gly Arg Phe Lys His Thr Asp Ala Cys Cys Arg
            20                  25                  30
```

```
Thr His Asp Met Cys Pro Asp Val Met Ser Ala Gly Glu Ser Lys His
         35                  40                  45
Gly Leu Thr Asn Thr Ala Ser His Thr Arg Leu Ser Cys Asp Cys Asp
 50                  55                  60
Asp Lys Phe Tyr Asp Cys Leu Lys Asn Ser Ala Asp Thr Ile Ser Ser
 65                  70                  75                  80
Tyr Phe Val Gly Lys Met Tyr Phe Asn Leu Ile Asp Thr Lys Cys Tyr
                 85                  90                  95
Lys Leu Glu His Pro Val Thr Gly Cys Gly Glu Arg Thr Glu Gly Arg
                100                 105                 110
Cys Leu His Tyr Thr Val Asp Lys Ser Lys Pro Lys Val Tyr Gln Trp
            115                 120                 125
Phe Asp Leu Arg Lys Tyr
        130
```

<210> SEQ ID NO 12
<211> LENGTH: 118
<212> TYPE: PRT
<213> ORGANISM: Naja mossambica

<400> SEQUENCE: 12

```
Asn Leu Tyr Gln Phe Lys Asn Met Ile His Cys Thr Val Pro Ser Arg
 1               5                  10                  15
Pro Trp Trp His Phe Ala Asp Tyr Gly Cys Tyr Cys Gly Arg Gly Gly
                 20                  25                  30
Lys Gly Thr Ala Val Asp Asp Leu Asp Arg Cys Cys Gln Val His Asp
         35                  40                  45
Asn Cys Tyr Gly Glu Ala Glu Lys Leu Gly Cys Trp Pro Tyr Leu Thr
 50                  55                  60
Leu Tyr Lys Tyr Glu Cys Ser Gln Gly Lys Leu Thr Cys Ser Gly Gly
 65                  70                  75                  80
Asn Asn Lys Cys Glu Ala Ala Val Cys Asn Cys Asp Leu Val Ala Ala
                 85                  90                  95
Asn Cys Phe Ala Gly Ala Pro Tyr Ile Asp Ala Asn Tyr Asn Val Asn
                100                 105                 110
Leu Lys Glu Arg Cys Gln
        115
```

<210> SEQ ID NO 13
<211> LENGTH: 1020
<212> TYPE: DNA
<213> ORGANISM: Homo sapiens

<400> SEQUENCE: 13

```
ggccttccaa agtgctggga ttacaggcgt gagtcaccgc gcccggccaa ataaaataaa    60
atgttaaagc aaattcagga ctaccctcc tccaagtctt ctgttccctt tgggcgccca   120
ggtgagcggg ggaggggctg ggggagtaat aacatcaaaa gagcgccttt tcctccctta   180
ttccgaggag acttccctgg gcctgactcc cggtcctgtc cccagcgccc cgcggcctct   240
ggagccccttt cagtgaccaa gatacagaga tcaggacgcc tttgcgccgc cccaggtgcc   300
cgcccctagc tggctctgct tgggccgcga gggaaggtga ggtcggggc ggagccgggg   360
cgtgacagcc ggggtgtgtg tccgccgggc ttggtgcctc cggtggccct gcagcaccgt   420
cccacctctg ccaccctccg atggggccgc tacctgtgtg cctgccaatc atgctgctcc   480
tgctactgcc gtcgctgctg ctgctgctgc ttctacctgg ccccgggtcc ggcgaggcct   540
```

```
ccaggatatt acgtgtgcac cggcgtggga tcctggaact ggcaggaact gtgggttgtg    600
ttggtccccg aacccccatc gcctatatga aatatggttg cttttgtggc ttgggaggcc    660
atggccagcc ccgcgatgcc attgactggt gctgccatgg ccacgactgt tgttacactc    720
gagctgagga ggccggctgc agccccaaga cagagcgcta ctcctggcag tgcgtcaatc    780
agagcgtcct gtgcggaccg gcagagaaca aatgccaaga actgttgtgc aagtgtgacc    840
aggagattgc taactgctta gcccaaactg agtacaactt aaagtacctc ttctacccccc   900 agttcctatg tgagccggac tcgcccaagt gtgactgact accttgactt gaaatgctct    960
tttgcacaag gaaataaagc gtcctctcag taatgaaaaa aaaaaaaaaa aaaaaaaaa    1020
```

<210> SEQ ID NO 14
<211> LENGTH: 1040
<212> TYPE: DNA
<213> ORGANISM: Mus musculus

<400> SEQUENCE: 14

```
ctcctcaagg ctccaggtga ccactcctgc ttgactccgc cccacggaaa gaaggtgagg     60 taggggggcgg ggctggtggt gggggtcggc aggattggtg agtatactgg cccttctggt   120
cagtcctaca cctgtcactc tcctatgtgt gggccacctc tgtgacgggc aataatgctg    180
ctgctactgc tgctgttgct gctgggacct ggacccggat tcagcgaagc aaccaggagg    240
tcacatgtat acaagcgtgg actcctggag ctggcaggga ccttggattg tgttgggcct    300
cgatctccga tggcttacat gaactatggc tgttattgtg gccttggtgg ccatggagag    360
ccacgtgacg ccattgactg gtgctgctac caccacgact gctgctactc tcgggctcag    420
gacgctggct gcagcctaa gttagaccgc tacccatgga agtgcatgga ccatcacatc    480
ctgtgtggac cagcagagaa caaatgccaa gaacttttgt gcaggtgtga cgaggagctg    540
gcttactgcc tggcagggac cgagtaccac ctgaaatacc tcttcttccc ctccattttta   600 tgtgagaagg actctcccaa gtgcaattga caggctcaca tgtccctttg cacatggaaa    660
cgcacttcac tttcagtgat caccaacagc atgcaatttg tgcaggagag tcaccggagt    720
ccaagtgcta aagccacctg cgtttgcttt ctccttccat tcaggaactc acaactatga    780
gcctgtggag ttgccagtct gatgaaggtt caaagtcctg gcctgttttt atacaaatag    840
cgctgtgttg ggcgtggtat acttttttgaa attcagcctt tatgagaagc tgtactatct    900
tgtacctgct gcagggctgc tggtcagatg tgggtgaaca cctgcttagg cttggctgtg    960
gtaataacat tgccacatga tacatctaag aattgtaact gtaataaaaa aatgttccct  1020
aaaaaaaaaa aaaaaaaaaa                                                1040
```

<210> SEQ ID NO 15
<211> LENGTH: 456
<212> TYPE: DNA
<213> ORGANISM: Rattus norvegicus

<400> SEQUENCE: 15

```
atgctgctgc tactgctgct gttgctactg ggacctggat cctgtctcag cgaagcaacc     60
aggaggtcac atgtgtacaa gcgtggactc ctggaactgg cagggacctt ggattgtgtt    120
ggtcctcgat cgccgatggc ttacatgaac tatggttgtt attgtggcct tggtggccac    180
ggagagccac gtgatgccat tgactggtgc tgctactacc atgactgctg ctactctcag    240
gctcaggatg ccggctgcag ccccaagcta taccgatacc cgtggaagtg catggaccat    300
cgcatcctgt gtggaccggc agagaacaaa tgccaagaac tcctatgcag gtgtgatgag    360
```

| | |
|---|---|
| acgctcgcat actgcctggc agacacagag taccacctga aatacctctt cttcccctcg | 420 |
| gttttatgtg agaaggactc acccaagtgc aactaa | 456 |

<210> SEQ ID NO 16
<211> LENGTH: 441
<212> TYPE: DNA
<213> ORGANISM: Sus scrofa

<400> SEQUENCE: 16

| | |
|---|---|
| atgaaattcc tcgtgttggc tgttctgctc acagtgggcg ctgcccagga aggcatcagc | 60 |
| tcaagggcat tatggcagtt tcgtagcatg attaagtgcg caatcccggg cagtcacccc | 120 |
| ttgatggatt tcaacaacta tggctgctac tgtggcctag gtggatcagg gaccectgtg | 180 |
| gatgaactgg acaggtgctg cgagacacac gacaactgct acagagatgc caagaacctg | 240 |
| gacagctgta aattcctcgt ggacaatccc tacaccgaaa gctactccta ctcatgttct | 300 |
| aacactgaga tcacctgcaa cagcaaaaac aatgcttgtg aggccttcat ctgtaactgt | 360 |
| gaccgaaatg ctgccatttg cttctcaaag gccccataca acaaggagca caagaacctg | 420 |
| gacaccaaga gtactgtta g | 441 |

<210> SEQ ID NO 17
<211> LENGTH: 504
<212> TYPE: DNA
<213> ORGANISM: Apis mellifera

<400> SEQUENCE: 17

| | |
|---|---|
| atgcaagtcg ttctcggatc cttgttcctt ctcctcctct ctacctctca cggatggcaa | 60 |
| atcagggata ggatcgggga taacgagttg gaggaacgga taatatatcc aggaacgtta | 120 |
| tggtgcgggc atggtaacaa gtcgtccggc ccgaacgagc taggtcggtt caagcacacg | 180 |
| gatgcatgct gtcgaaccca cgacatgtgc ccggacgtga tgtcagctgg tgaatcgaag | 240 |
| cacggcctga ccaacacggc ctcccacacc aggttgtcgt gcgactgcga cgacaagttc | 300 |
| tatgattgtc ttaaaaattc ggcggacacg attagctcgt atttcgtagg gaagatgtac | 360 |
| ttcaatctga tagacacgaa gtgttacaaa ctggagcatc ctgtcaccgg gtgcggtgag | 420 |
| agaaccgagg tcgttgtctt tcactacacc gtggacaaaa gcaaaccgaa agtgtaccaa | 480 |
| tggttcgatc ttcgcaagta ttga | 504 |

<210> SEQ ID NO 18
<211> LENGTH: 441
<212> TYPE: DNA
<213> ORGANISM: Naja mossambica

<400> SEQUENCE: 18

| | |
|---|---|
| atgaatcctg ctcaccttct gatcctggca gcagtttgtg tctcccccctt aggagcctcc | 60 |
| tctaatcgtc ccatgcctct caacctctat cagttcaaaa acatgattca atgtactgtc | 120 |
| cccaatcgat cttggtggca ttttgcggac tacggttgct actgcggacg cggaggtagc | 180 |
| gggacaccag tagacgactt ggataggtgc tgccagattc atgacaactg ctataatgaa | 240 |
| gctgaaaaaa tttccagatg ctggcectac ttcaagacct attcatacga gtgttctcaa | 300 |
| ggcacactca cctgcaaagg tggcaacaat gcgtgtgcag ctgctgtctg tgattgtgac | 360 |
| cgcttggcag ccatctgctt cgccggagcc ccttacaacg ataacaacta caatatcgac | 420 |
| ctcaaggcac gttgccaatg a | 441 |

<210> SEQ ID NO 19

```
<211> LENGTH: 37
<212> TYPE: DNA
<213> ORGANISM: Artificial
<220> FEATURE:
<223> OTHER INFORMATION: primer

<400> SEQUENCE: 19
ttgatatcgc cgccaccatg gacctgcccc cgcagct                              37

<210> SEQ ID NO 20
<211> LENGTH: 23
<212> TYPE: DNA
<213> ORGANISM: Artificial
<220> FEATURE:
<223> OTHER INFORMATION: primer

<400> SEQUENCE: 20
ttacttctgg gacttgcccc ctt                                            23

<210> SEQ ID NO 21
<211> LENGTH: 5020
<212> TYPE: DNA
<213> ORGANISM: Artificial
<220> FEATURE:
<223> OTHER INFORMATION: probe

<400> SEQUENCE: 21
ctgcagcctg aatatgggcc aaacaggata tctgtggtaa gcagttcctg ccccggctca      60
gggccaagaa cagatggaac agctgaatat gggccaaaca ggatatcgt ggtaagcagt     120 tcctgccccg gctcagggcc aagaacagat ggtccccaga tgcggtccag ccctcagcag    180
tttctagaga accatcagat gtttccaggg tgccccaagg acctgaaatg accctgtgcc    240
ttatttgaac taaccaatca gttcgcttct cgcttctgtt cgcgcgcttc tgctccccga    300
gctcaataaa agagcccaca acccctcact cggggcgcca gtcctccgat tgactgagtc    360
gcccgggtac ccgtgtatcc aataaaccct cttgcagttg catccgactt gtggtctcgc    420
tgttccttgg gagggtctcc tctgagtgat tgactacccg tcagcggggg tctttcattt    480
gggggctcgt ccgggatcgg gagacccctg cccaggacc accgacccac caccgggagg    540
taagctggcc agcaacttat ctgtgtctgt ccgattgtct agtgtctatg actgattta     600 tgcgcctgcg tcggtactag ttagctaact agctctgtat ctggcggacc cgtggtggaa    660
ctgacgagtt ctgaacaccc ggccgcaacc ctgggagacg tcccagggac tttgggggcc    720
gttttttgtg g cccgacctga ggaagggagt cgatgtggaa tccgacccccg tcaggatatg    780 tggttctggt aggagacgag aacctaaaac agttcccgcc tccgtctgaa ttttttgcttt    840 cggtttggaa ccgaagccgc gcgtcttgtc tgctgcagca tcgttctgtg ttgtctctgt    900
ctgactgtgt ttctgtattt gtctgaaaat tagggccaga ctgttaccac tcccttaagt    960
ttgaccttag atcactggaa agatgtcgag cggctcgctc acaaccagtc ggtagatgtc   1020
aagaagagac gttgggttac cttctgctct gcagaatggc caacctttaa cgtcggatgg   1080
ccgcgagacg gcacctttaa ccgagaccctc atcacccagg ttaagatcaa ggtcttttca   1140
cctggcccgc atggacaccc agaccaggtc cctacatcg tgacctggga agccttggct   1200
tttgaccccc ctccctgggt caagcccttt gtacaccta agcctccgcc tcctcttctt   1260
ccatccgcgc cgtctctccc ccttgaacct cctctttcga cccccgcctca atcctccctt   1320 tatccagccc tcactccttc tctaggcgcc ggcggatcc cagtgtggtg gtacgtagga   1380
attcgccagc acagtggtcg acctgtggaa tgtgtgtcag ttagggtgtg gaaagtcccc   1440
```

```
aggctcccca gcaggcagaa gtatgcaaag catgcatctc aattagtcag caaccaggtg   1500
tggaaagtcc ccaggctccc cagcaggcag aagtatgcaa agcatgcatc tcaattagtc   1560
agcaaccata gtcccgcccc taactccgcc catcccgccc ctaactccgc ccagttccgc   1620
ccattctccg ccccatggct gactaatttt ttttatttat gcagaggccg aggccgcctc   1680
ggcctctgag ctattccaga agtagtgagg aggcttttt ggaggcctag gcttttgcaa   1740
acgctgcttg aggctgaagg tgcgttgctg gcgttttcc ataggctccg ccccctgac    1800 gagcatcaca aaaatcgacg ctcaagtcag aggtggcgaa acccgacagg actataaaga   1860
taccaggcgt ttccccctgg aagctccctc gtgcgctctc ctgttccgac cctgccgctt   1920
accggatacc tgtccgcctt tctcccttcg ggaagcgtgg cgctttctca tagctcacgc   1980
tgtaggtatc tcagttcggt gtaggtcgtt cgctccaagc tgggctgtgt gcacgaaccc   2040
cccgttcagc ccgaccgctg cgccttatcc ggtaactatc gtcttgagtc caacccggta   2100
agacacgact tatcgccact ggcagcagcc actggtaaca ggattagcag agcgaggtat   2160
gtaggcggtg ctacagagtt cttgaagtgg tggcctaact acggctacac tagaaggaca   2220
gtatttggta tctgcgctct gctgaagcca gttaccttcg gaaaaagagt tggtagctct   2280
tgatccggca aacaaccac cgctggtagc ggtggttttt ttgtttgcaa gcagcagatt   2340
acgatcgata aataaaaga ttttatttag tctccagaaa aaggggggaa tgaaagaccc   2400
cacctgtagg tttggcaagc tagcttaagt aacgccattt tgcaaggcat ggaaaatac    2460 ataactgaga atagagaagt tcagatcaag gtcaggaaca gatggaacag ctgaatatgg   2520
gccaaacagg atatctgtgg taagcagttc ctgccccggc tcagggccaa gaacagatgg   2580
aacagctgaa tatgggccaa acaggatatc tgtggtaagc agttcctgcc ccggctcagg   2640
gccaagaaca gatggtcccc agatgcggtc cagccctcag cagtttctag agaaccatca   2700
gatgtttcca gggtgcccca aggacctgaa atgaccctgt gccttatttg aactaaccaa   2760
tcagttcgct tctcgcttct gttcgcgcgc ttctgctccc cgagctcaat aaaagagccc   2820 acaaccctc actcggggcg ccagtcctcc gattgactga gtcgcccggg tacccgtgta   2880
tccaataaac cctcttgcag ttgcatccga cttgtggtct cgctgttcct gggagggtc    2940 tcctctgagt gattgactac ccgtcagcgg gggtctttca catgcagcat gtatcaaaat   3000
taatttggtt ttttttctta agtatttaca ttaaatggcc atagttgcat taatgaatcg   3060
gccaacgcgc ggggagaggc ggtttgcgta ttgggcgctc ttccgcttcc tcgctcactg   3120
actcgctgcg ctcggtcgtt cggctgcggc gagcggtatc agctcactca aaggcggtaa   3180
tacggttatc cacagaatca ggggataacg caggaaagaa catgtgagca aaaggccagc   3240
aaaaggccag gaaccgtaaa aaggccgcgt tgctggcgtt tttccatagg ctccgccccc   3300
ctgacgagca tcacaaaaat cgacgctcaa gtcagaggtg gcgaaacccg acaggactat   3360
aaagatacca ggcgtttccc cctggaagct ccctcgtgcg ctctcctgtt ccgaccctgc   3420
cgcttaccgg atacctgtcc gcctttctcc cttcgggaag cgtggcgctt tctcatagct   3480
cacgctgtag gtatctcagt tcggtgtagg tcgttcgctc caagctgggc tgtgtgcacg   3540
aaccccccgt tcagcccgac cgctgcgcct tatccggtaa ctatcgtctt gagtccaacc   3600
cggtaagaca cgacttatcg ccactggcag cagccactgg taacaggatt agcagagcga   3660
ggtatgtagg cggtgctaca gagttcttga agtggtggcc taactacggc tacactagaa   3720
ggacagtatt tggtatctgc gctctgctga agccagttac cttcggaaaa agagttggta   3780
gctcttgatc cggcaaacaa accaccgctg gtagcggtgg tttttttgtt tgcaagcagc   3840
```

```
agattacgcg cagaaaaaaa ggatctcaag aagatccttt gatcttttct acggggtctg    3900
acgctcagtg gaacgaaaac tcacgttaag ggattttggt catgagatta tcaaaaagga    3960
tcttcaccta gatcctttta aattaaaaat gaagtttgcg gccgcaaatc aatctaaagt    4020
atatatgagt aaacttggtc tgacagttac caatgcttaa tcagtgaggc acctatctca    4080
gcgatctgtc tatttcgttc atccatagtt gcctgactcc ccgtcgtgta gataactacg    4140
atacgggagg gcttaccatc tggccccagt gctgcaatga taccgcgaga cccacgctca    4200
ccggctccag atttatcagc aataaaccag ccagccggaa gggccgagcg cagaagtggt    4260
cctgcaactt tatccgcctc catccagtct attaattgtt gccgggaagc tagagtaagt    4320
agttcgccag ttaatagttt gcgcaacgtt gttgccattg ctacaggcat cgtggtgtca    4380
cgctcgtcgt ttggtatggc ttcattcagc tccggttccc aacgatcaag gcgagttaca    4440
tgatccccca tgttgtgcaa aaaagcggtt agctccttcg gtcctccgat cgttgtcaga    4500
agtaagttgg ccgcagtgtt atcactcatg gttatggcag cactgcataa ttctcttact    4560
gtcatgccat ccgtaagatg cttttctgtg actggtgagt actcaaccaa gtcattctga    4620
gaatagtgta tgcggcgacc gagttgctct tgcccggcgt caacacggga taataccgcg    4680
ccacatagca gaactttaaa agtgctcatc attggaaaac gttcttcggg gcgaaaactc    4740
tcaaggatct taccgctgtt gagatccagt tcgatgtaac ccactcgtgc acccaactga    4800
tcttcagcat cttttacttt caccagcgtt tctgggtgag caaaaacagg aaggcaaaat    4860
gccgcaaaaa agggaataag ggcgacacgg aaatgttgaa tactcatact cttccttttt    4920
caatattatt gaagcattta tcagggttat tgtctcatga gcggatacat atttgaatgt    4980
atttagaaaa ataaacaaat aggggttccg cgcacatttc                          5020

<210> SEQ ID NO 22
<211> LENGTH: 83
<212> TYPE: DNA
<213> ORGANISM: Artificial
<220> FEATURE:
<223> OTHER INFORMATION: primer

<400> SEQUENCE: 22
cccaagcttg atatcgaatt cgacgtcaca gtatgacggc catgggaatt cgacgtcaca    60
gtatgacggc catggggatc ccg                                            83

<210> SEQ ID NO 23
<211> LENGTH: 83
<212> TYPE: DNA
<213> ORGANISM: Artificial
<220> FEATURE:
<223> OTHER INFORMATION: primer

<400> SEQUENCE: 23
cgggatcccc atggccgtca tactgtgacg tcgaattccc atggccgtca tactgtgacg    60
tcgaattcga tatcaagctt ggg                                            83

<210> SEQ ID NO 24
<211> LENGTH: 78
<212> TYPE: DNA
<213> ORGANISM: Artificial
<220> FEATURE:
<223> OTHER INFORMATION: primer

<400> SEQUENCE: 24
tgcactgcag gaattcccat ggccgtcata ctgtgacgtc gaattcccat ggccgtcata    60
```

```
ctgtgacgtc ggatcccg                                                  78

<210> SEQ ID NO 25
<211> LENGTH: 78
<212> TYPE: DNA
<213> ORGANISM: Artificial
<220> FEATURE:
<223> OTHER INFORMATION: primer

<400> SEQUENCE: 25
cgggatccga cgtcacagta tgacggccat gggaattcga cgtcacagta tgacggccat   60
gggaattcct gcagtgca                                                 78

<210> SEQ ID NO 26
<211> LENGTH: 30
<212> TYPE: DNA
<213> ORGANISM: Artificial
<220> FEATURE:
<223> OTHER INFORMATION: primer

<400> SEQUENCE: 26
tcgactgcag cccatggccg tcatactgtg                                    30

<210> SEQ ID NO 27
<211> LENGTH: 30
<212> TYPE: DNA
<213> ORGANISM: Artificial
<220> FEATURE:
<223> OTHER INFORMATION: primer

<400> SEQUENCE: 27
tgcactgcag gtcggagctg actgttctgg                                    30

<210> SEQ ID NO 28
<211> LENGTH: 264
<212> TYPE: DNA
<213> ORGANISM: Artificial
<220> FEATURE:
<223> OTHER INFORMATION: promoter

<400> SEQUENCE: 28
tcgactgcag cccatggccg tcatactgtg tgacgtcttt cagagcactt tgtgattgct   60
cagtcctaag tataagccct ataaaatgat gggctttgaa atgctggtca gggtagagtg  120
agaagcacca gcaggcagta acagccaacc cttagccatt gctaagggca gagaactggt  180
ggagcctttc tcttactccc aggacttcag cacctaagac agctccaaaa caaaccagaa  240
cagtcagctc cgacctgcag tgca                                         264

<210> SEQ ID NO 29
<211> LENGTH: 993
<212> TYPE: DNA
<213> ORGANISM: Homo sapiens

<400> SEQUENCE: 29
atgctgccgg actggaagag ctccttgatc tcatggcttt acatcatcat cttcctcact   60
ggcctccctg ccaacctcct ggccctgcgg gcctttgtgg ggcggatccg ccagcccag   120 cctgcacctg tgcacatcct cctgctgagc ctgacgctgg ccgacctcct cctgctgctg  180
ctgctgccct tcaagatcat cgaggctgcg tcgaacttcc gctggtacct gcccaaggtc  240
gtctgcgccc tcacgagttt tggcttctac agcagcatct actgcagcac gtggctcctg  300
gcgggcatca gcatcgagcg ctacctggga gtggctttcc ccgtgcagta caagctctcc  360
```

```
cgccggcctc tgtatggagt gattgcagct ctggtggcct gggttatgtc ctttggtcac      420
tgcaccatcg tgatcatcgt tcaatacttg aacacgactg agcaggtcag aagtggcaat      480
gaaattacct gctacgagaa cttcaccgat aaccagttgg acgtggtgct gcccgtgcgg      540
ctggagctgt gcctggtgct cttcttcatc cccatggcag tcaccatctt ctgctactgg      600
cgttttgtgt ggatcatgct ctcccagccc cttgtggggg cccagaggcg gcgccgagcc      660
gtggggctgg ctgtggtgac gctgctcaat ttcctggtgt gcttcggacc ttacaacgtg      720
tcccacctgg tggggtatca ccagagaaaa agccctggt ggcggtcaat agccgtggtg       780
ttcagttcac tcaacgccag tctggacccc ctgctcttct atttctcttc ttcagtggtg      840
cgcagggcat ttgggagagg gctgcaggtg ctgcggaatc agggctcctc cctgttggga      900
cgcagaggca aagacacagc agaggggaca aatgaggaca ggggtgtggg tcaaggagaa      960
gggatgccaa gttcggactt cactacagag tag                                   993

<210> SEQ ID NO 30
<211> LENGTH: 39
<212> TYPE: DNA
<213> ORGANISM: Artificial
<220> FEATURE:
<223> OTHER INFORMATION: primer

<400> SEQUENCE: 30
ttaagcttgc cgccaccatg ctgccggact ggaagagct                              39

<210> SEQ ID NO 31
<211> LENGTH: 22
<212> TYPE: DNA
<213> ORGANISM: Artificial
<220> FEATURE:
<223> OTHER INFORMATION: primer

<400> SEQUENCE: 31
ctactctgta gtgaagtccg aa                                                22

<210> SEQ ID NO 32
<211> LENGTH: 26
<212> TYPE: DNA
<213> ORGANISM: Artificial
<220> FEATURE:
<223> OTHER INFORMATION: primer

<400> SEQUENCE: 32
atggggccgc tacctgtgtg cctgcc                                            26

<210> SEQ ID NO 33
<211> LENGTH: 25
<212> TYPE: DNA
<213> ORGANISM: Artificial
<220> FEATURE:
<223> OTHER INFORMATION: primer

<400> SEQUENCE: 33
tcagtcacac ttgggcgagt ccggc                                             25

<210> SEQ ID NO 34
<211> LENGTH: 25
<212> TYPE: DNA
<213> ORGANISM: Artificial
<220> FEATURE:
<223> OTHER INFORMATION: primer

<400> SEQUENCE: 34
```
atgctgctgc tactgctgct gttgc                                          25

<210> SEQ ID NO 35
<211> LENGTH: 25
<212> TYPE: DNA
<213> ORGANISM: Artificial
<220> FEATURE:
<223> OTHER INFORMATION: primer

<400> SEQUENCE: 35
tcaattgcac ttgggagagt ccttc                                          25

<210> SEQ ID NO 36
<211> LENGTH: 33
<212> TYPE: DNA
<213> ORGANISM: Artificial
<220> FEATURE:
<223> OTHER INFORMATION: primer

<400> SEQUENCE: 36
gatatcgccg ccaccatggg gccgctacct gtg                                 33

<210> SEQ ID NO 37
<211> LENGTH: 45
<212> TYPE: DNA
<213> ORGANISM: Artificial
<220> FEATURE:
<223> OTHER INFORMATION: primer

<400> SEQUENCE: 37
gatatctcaa tggtgatggt gatgatggtc acacttgggc gagtc                    45

<210> SEQ ID NO 38
<211> LENGTH: 33
<212> TYPE: DNA
<213> ORGANISM: Artificial
<220> FEATURE:
<223> OTHER INFORMATION: primer

<400> SEQUENCE: 38
gatatcgccg ccaccatgct gctgctactg ctg                                 33

<210> SEQ ID NO 39
<211> LENGTH: 45
<212> TYPE: DNA
<213> ORGANISM: Artificial
<220> FEATURE:
<223> OTHER INFORMATION: primer

<400> SEQUENCE: 39
gatatctcaa tggtgatggt gatgatgatt gcacttggga gagtc                    45

<210> SEQ ID NO 40
<211> LENGTH: 48
<212> TYPE: DNA
<213> ORGANISM: Artificial
<220> FEATURE:
<223> OTHER INFORMATION: primer

<400> SEQUENCE: 40
gatatctcac ttgtcatcgt cgtccttgta gtcgtcacac ttgggcga                 48

<210> SEQ ID NO 41
<211> LENGTH: 522
<212> TYPE: DNA
<213> ORGANISM: Homo sapiens

```
<400> SEQUENCE: 41
atggggccgc tacctgtgtg cctgccaatc atgctgctcc tgctactgcc gtcgctgctg      60
ctgctgctgc ttctacctgg ccccgggtcc ggcgaggcct ccaggatatt acgtgtgcac     120
cggcgtggga tcctggaact ggcaggaact gtgggttgtg ttggtccccg aaccccatc     180 gcctatatga aatatggttg cttttgtggc ttgggaggcc atggccagcc ccgcgatgcc     240
attgactggt gctgccatgg ccacgactgt tgttacactc gagctgagga ggccggctgc     300
agccccaaga cagagcgcta ctcctggcag tgcgtcaatc agagcgtcct gtgcggaccg     360
gcagagaaca aatgccaaga actgttgtgc aagtgtgacc aggagattgc taactgctta     420
gcccaaactg agtacaactt aaagtacctc ttctacccc agttcctatg tgagccggac     480
tcgcccaagt gtgacgacta caaggacgac gatgacaagt ga                       522

<210> SEQ ID NO 42
<211> LENGTH: 48
<212> TYPE: DNA
<213> ORGANISM: Artificial
<220> FEATURE:
<223> OTHER INFORMATION: primer

<400> SEQUENCE: 42
gatatctcac ttgtcatcgt cgtccttgta gtcattgcac ttgggaga                  48

<210> SEQ ID NO 43
<211> LENGTH: 480
<212> TYPE: DNA
<213> ORGANISM: Mus musculus

<400> SEQUENCE: 43
atgctgctgc tactgctgct gttgctgctg ggacctggac ccggattcag cgaagcaacc      60
aggaggtcac atgtatacaa gcgtggactc ctggagctgg cagggaccit ggattgtgtt     120 gggcctcgat ctccgatggc ttacatgaac tatggctgtt attgtggcct tggtggccat     180
ggagagccac gtgacgccat tgactggtgc tgctaccacc acgactgctg ctactctcgg     240
gctcaggacg ctggctgcag ccctaagtta gaccgctacc catggaagtg catggaccat     300
cacatcctgt gtggaccagc agagaacaaa tgccaagaac ttttgtgcag gtgtgacgag     360
gagctggctt actgcctggc agggaccgag taccacctga aatacctctt cttcccctcc     420
attttatgtg agaaggactc tcccaagtgc aatgactaca aggacgacga tgacaagtga     480
```